US011446141B2

(12) United States Patent
Dvorsky et al.

(10) Patent No.: US 11,446,141 B2
(45) Date of Patent: Sep. 20, 2022

(54) PROSTHETIC HEART VALVE HAVING NON-CYLINDRICAL FRAME

(71) Applicant: Edwards Lifesciences Corporation, Irvine, CA (US)

(72) Inventors: Anatoly Dvorsky, Haifa (IL); Tamir S. Levi, Zikhron Yaakov (IL); Yair A. Neumann, Moshav Sede Varburg (IL); Noa Axelrod Manela, Herzeliya (IL); Eitan Atias, Tel Aviv (IL); Oren Cohen, Kadima (IL); Elazar Levi Schwarcz, Netanya (IL); Ofir Witzman, Kfar Saba (IL); Noam Miller, Givatayim (IL); Boaz Manash, Givat Ada (IL); Danny M. Garmahi, Hadera (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/788,090

(22) Filed: Feb. 11, 2020

(65) Prior Publication Data
US 2020/0188099 A1 Jun. 18, 2020

Related U.S. Application Data

(63) Continuation of application No. PCT/US2019/056865, filed on Oct. 18, 2019.
(Continued)

(51) Int. Cl.
*A61F 2/24* (2006.01)
*A61F 2/95* (2013.01)

(52) U.S. Cl.
CPC .......... *A61F 2/2418* (2013.01); *A61F 2/9522* (2020.05); *A61F 2210/0014* (2013.01);
(Continued)

(58) Field of Classification Search
CPC .. A61F 2/2418; A61F 2/24; A61F 2/82; A61F 2/88; A61F 2230/0076; A61F 2230/0078
See application file for complete search history.

(56) References Cited

U.S. PATENT DOCUMENTS 3,409,013 A 11/1968 Berry
3,548,417 A 12/1970 Kisher
(Continued)

FOREIGN PATENT DOCUMENTS

DE 0144167 C 9/1903
DE 2246526 A1 3/1973
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Jennifer Dieterle
*Assistant Examiner* — Amanda M Barkan
(74) *Attorney, Agent, or Firm* — Klarquist Sparkman, LLP; Sean Seung Kyu Kim

(57) ABSTRACT

An implantable prosthetic device can include a frame that is radially expandable and compressible between a radially compressed configuration and a radially expanded configuration. The frame can have a first set of a plurality of struts extending in a first direction, and a second set of a plurality of struts extending in a second direction, and each strut of the first set of struts can be pivotably connected to at least one strut of the second set of struts. Each strut can be curved helically with respect to a first, longitudinal axis of the
(Continued)

frame, and each strut can be curved with respect to a second axis that is perpendicular to the first, longitudinal axis of the frame.

17 Claims, 29 Drawing Sheets

Related U.S. Application Data

(60) Provisional application No. 62/799,678, filed on Jan. 31, 2019, provisional application No. 62/748,284, filed on Oct. 19, 2018.

(52) U.S. Cl.
CPC ............... *A61F 2230/0008* (2013.01); *A61F 2230/0078* (2013.01); *A61F 2250/001* (2013.01)

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| RE30,912 E | 4/1982 | Hancock |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goicoechea et al. |
| 6,338,740 B1 | 1/2002 | Carpenter |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz et al. |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |

(56) References Cited

U.S. PATENT DOCUMENTS

| | | |
|---|---|---|
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,316,710 B1 | 1/2008 | Cheng et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,665 B2 | 6/2011 | Pienknagura |
| 7,959,672 B2 | 6/2011 | Salahieh et al. |
| 7,993,394 B2 | 8/2011 | Hariton et al. |
| 8,029,556 B2 | 10/2011 | Rowe |
| 8,075,611 B2 | 12/2011 | Millwee et al. |
| 8,128,686 B2 | 3/2012 | Paul, Jr. et al. |
| 8,167,932 B2 | 5/2012 | Bourang et al. |
| 8,291,570 B2 | 10/2012 | Eidenschink et al. |
| 8,308,798 B2* | 11/2012 | Pintor ............... A61F 2/243 623/2.18 |
| 8,348,998 B2 | 1/2013 | Pintor et al. |
| 8,449,606 B2 | 5/2013 | Eliasen et al. |
| 8,454,685 B2 | 6/2013 | Hariton et al. |
| 8,652,203 B2 | 2/2014 | Quadri et al. |
| 8,747,463 B2 | 6/2014 | Fogarty et al. |
| 8,845,720 B2* | 9/2014 | Conklin ............... A61F 2/2418 623/2.14 |
| 9,078,781 B2 | 7/2015 | Ryan et al. |
| 9,700,442 B2* | 7/2017 | White ............... A61F 2/2418 |
| 10,729,530 B2* | 8/2020 | Opie ............... A61B 5/6862 |
| 2001/0021872 A1 | 9/2001 | Bailey et al. |
| 2002/0026094 A1 | 2/2002 | Roth |
| 2002/0032481 A1 | 3/2002 | Gabbay |
| 2002/0138135 A1 | 9/2002 | Duerig et al. |
| 2002/0143390 A1 | 10/2002 | Ishii |
| 2002/0173842 A1 | 11/2002 | Buchanan |
| 2003/0014105 A1 | 1/2003 | Cao |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0024452 A1 | 2/2004 | Kruse et al. |
| 2004/0039436 A1 | 2/2004 | Spenser et al. |
| 2004/0078074 A1 | 4/2004 | Anderson et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0010285 A1 | 1/2005 | Lambrecht et al. |
| 2005/0075725 A1 | 4/2005 | Rowe |
| 2005/0075728 A1 | 4/2005 | Nguyen et al. |
| 2005/0096736 A1 | 5/2005 | Osse et al. |
| 2005/0096738 A1 | 5/2005 | Cali et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0004469 A1 | 1/2006 | Sokel |
| 2006/0025857 A1 | 2/2006 | Bergheim et al. |
| 2006/0058872 A1 | 3/2006 | Salahieh et al. |
| 2006/0074484 A1 | 4/2006 | Huber |
| 2006/0108090 A1 | 5/2006 | Ederer et al. |
| 2006/0149350 A1 | 7/2006 | Patel et al. |
| 2006/0183383 A1 | 8/2006 | Asmus et al. |
| 2006/0229719 A1 | 10/2006 | Marquez et al. |
| 2006/0259136 A1 | 11/2006 | Nguyen et al. |
| 2006/0259137 A1 | 11/2006 | Artof et al. |
| 2006/0287717 A1 | 12/2006 | Rowe et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0233228 A1 | 10/2007 | Eberhardt et al. |
| 2007/0260305 A1 | 11/2007 | Drews et al. |
| 2007/0265700 A1 | 11/2007 | Eliasen et al. |
| 2008/0021546 A1 | 1/2008 | Patz et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0183271 A1 | 7/2008 | Frawley et al. |
| 2008/0208327 A1 | 8/2008 | Rowe |
| 2008/0243245 A1 | 10/2008 | Thambar et al. |
| 2008/0255660 A1 | 10/2008 | Guyenot et al. |
| 2008/0275537 A1 | 11/2008 | Limon |
| 2008/0294248 A1 | 11/2008 | Yang et al. |
| 2009/0118826 A1 | 5/2009 | Khaghani |
| 2009/0125118 A1 | 5/2009 | Gong |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0299452 A1 | 12/2009 | Eidenschink et al. |
| 2009/0319037 A1 | 12/2009 | Rowe et al. |
| 2010/0004735 A1 | 1/2010 | Yang et al. |
| 2010/0049313 A1 | 2/2010 | Alon et al. |
| 2010/0082094 A1 | 4/2010 | Quadri et al. |
| 2010/0168844 A1 | 7/2010 | Toomes et al. |
| 2010/0185277 A1 | 7/2010 | Braido et al. |
| 2010/0198347 A1 | 8/2010 | Zakay et al. |
| 2010/0204781 A1 | 8/2010 | Alkhatib |
| 2011/0015729 A1 | 1/2011 | Jimenez et al. |
| 2011/0022157 A1 | 1/2011 | Essinger et al. |
| 2011/0066224 A1 | 3/2011 | White |
| 2011/0137397 A1 | 6/2011 | Chau et al. |
| 2011/0218619 A1 | 9/2011 | Benichou et al. |
| 2011/0319991 A1 | 12/2011 | Hariton et al. |
| 2012/0089223 A1 | 4/2012 | Nguyen et al. |
| 2012/0101571 A1 | 4/2012 | Thambar et al. |
| 2012/0123529 A1 | 5/2012 | Levi et al. |
| 2012/0259409 A1 | 10/2012 | Nguyen et al. |
| 2013/0023985 A1 | 1/2013 | Khairkhahan et al. |
| 2013/0046373 A1 | 2/2013 | Cartledge et al. |
| 2013/0150956 A1 | 6/2013 | Yohanan et al. |
| 2013/0166017 A1 | 6/2013 | Cartledge et al. |
| 2013/0190857 A1 | 7/2013 | Mitra et al. |
| 2013/0274873 A1 | 10/2013 | Delaloye et al. |
| 2013/0310926 A1 | 11/2013 | Hariton |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0209238 A1 | 7/2014 | Bonyuet et al. |
| 2014/0222136 A1 | 8/2014 | Geist et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0277563 A1 | 9/2014 | White |
| 2014/0296962 A1 | 10/2014 | Cartledge et al. |
| 2014/0330372 A1 | 11/2014 | Weston et al. |
| 2014/0343670 A1 | 11/2014 | Bakis et al. |
| 2014/0343671 A1 | 11/2014 | Yohanan et al. |
| 2014/0350667 A1 | 11/2014 | Braido et al. |
| 2015/0073545 A1 | 3/2015 | Braido |

(56) References Cited

U.S. PATENT DOCUMENTS

| | | |
|---|---|---|
| 2015/0073546 A1 | 3/2015 | Braido |
| 2015/0135506 A1 | 5/2015 | White |
| 2015/0157455 A1 | 6/2015 | Hoang et al. |
| 2016/0374802 A1 | 12/2016 | Levi et al. |
| 2017/0014229 A1 | 1/2017 | Nguyen-Thien-Nhon et al. |
| 2018/0028310 A1 | 2/2018 | Gurovich et al. |
| 2018/0153689 A1 | 6/2018 | Maimon et al. |
| 2018/0325665 A1 | 11/2018 | Gurovich et al. |
| 2018/0344456 A1 | 12/2018 | Barash et al. |
| 2019/0159894 A1 | 5/2019 | Levi et al. |
| 2019/0192288 A1 | 6/2019 | Levi et al. |
| 2019/0192289 A1 | 6/2019 | Levi et al. |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 A1 | 3/1984 |
| EP | 0850607 A1 | 7/1998 |
| EP | 1057460 A1 | 12/2000 |
| EP | 1088529 A2 | 4/2001 |
| EP | 1570809 A1 | 9/2005 |
| FR | 2788217 A1 | 7/2000 |
| FR | 2815844 A1 | 5/2002 |
| GB | 2056023 A | 3/1981 |
| SU | 1271508 A1 | 11/1986 |
| WO | 9117720 A1 | 11/1991 |
| WO | 9217118 A1 | 10/1992 |
| WO | 9301768 A1 | 2/1993 |
| WO | 9724080 A1 | 7/1997 |
| WO | 9829057 A1 | 7/1998 |
| WO | 9930646 A1 | 6/1999 |
| WO | 9933414 A1 | 7/1999 |
| WO | 9940964 A1 | 8/1999 |
| WO | 9947075 A1 | 9/1999 |
| WO | 0018333 A1 | 4/2000 |
| WO | 0041652 A1 | 7/2000 |
| WO | 0047139 A1 | 8/2000 |
| WO | 0135878 A2 | 5/2001 |
| WO | 0149213 A2 | 7/2001 |
| WO | 0154624 A1 | 8/2001 |
| WO | 0154625 A1 | 8/2001 |
| WO | 0162189 A1 | 8/2001 |
| WO | 0164137 A1 | 9/2001 |
| WO | 0176510 A2 | 10/2001 |
| WO | 0222054 A1 | 3/2002 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 0249540 A2 | 6/2002 |
| WO | 03047468 A1 | 6/2003 |
| WO | 2005034812 | 4/2005 |
| WO | 2005055883 A1 | 6/2005 |
| WO | 2005084595 A1 | 9/2005 |
| WO | 2006014233 A2 | 2/2006 |
| WO | 2006032051 A2 | 3/2006 |
| WO | 2006034008 A2 | 3/2006 |
| WO | 2006111391 A1 | 10/2006 |
| WO | 2006127089 A1 | 11/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008035337 A2 | 3/2008 |
| WO | 2008091515 A2 | 7/2008 |
| WO | 2008147964 A1 | 12/2008 |
| WO | 2008150529 A1 | 12/2008 |
| WO | 2009033469 A1 | 3/2009 |
| WO | 2009053497 A1 | 4/2009 |
| WO | 2009061389 A2 | 5/2009 |
| WO | 2009094188 A2 | 7/2009 |
| WO | 2009116041 | 9/2009 |
| WO | 2009149462 A2 | 12/2009 |
| WO | 2010011699 A2 | 1/2010 |
| WO | 2010121076 A2 | 10/2010 |
| WO | 2012087842 A1 | 6/2012 |
| WO | 2013106585 A1 | 7/2013 |
| WO | 2015085218 A1 | 6/2015 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1 pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Patrick W. Serruys, Nicolo Piazza, Alain Cribier, John Webb, Jean-Claude Laborde, Peter de Jaegere, "Transcatheter Aortic Valve Implantation: Tips and Tricks to Avoid Failure"; we file the table of contents and pp. 18 to 39 (Chapter 2) and pp. 102-114 (Chapter 8); the publication date according to the "Library of Congress Cataloging-in-Publication Data" is Nov. 24, 2009.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

\* cited by examiner

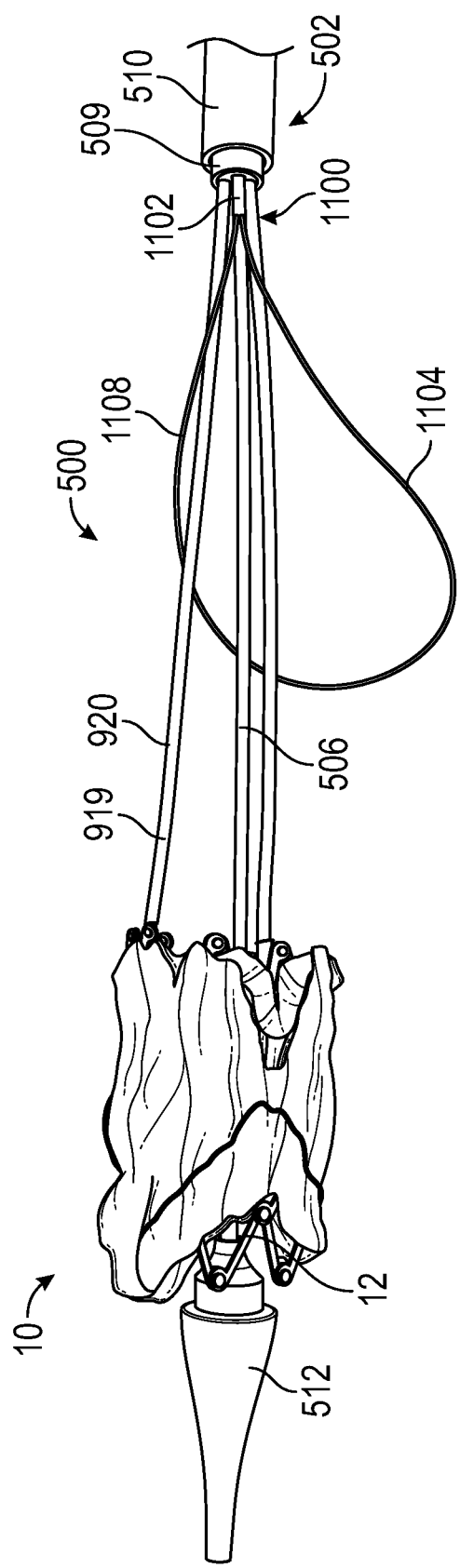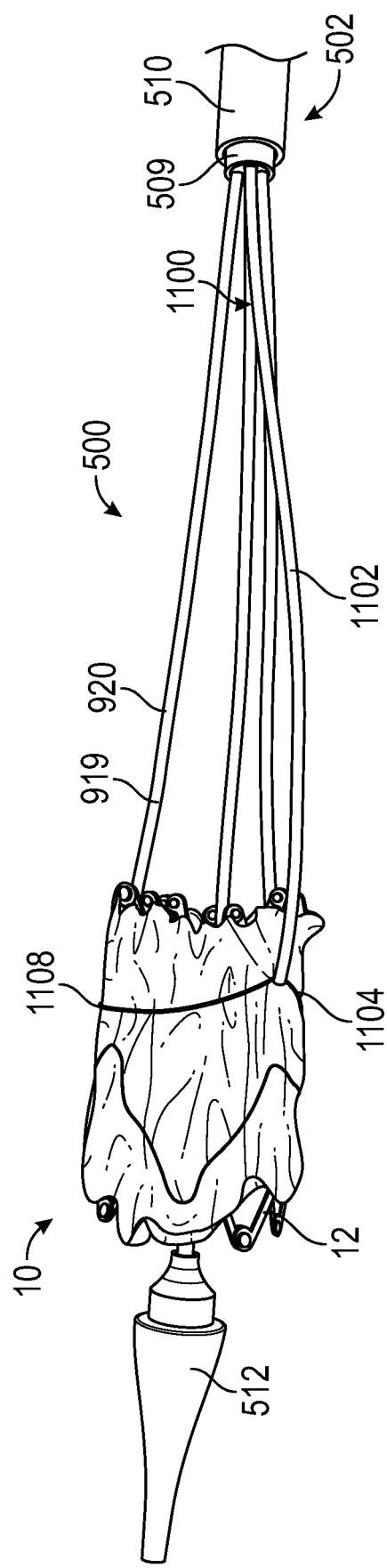
FIG. 22
FIG. 23

PROSTHETIC HEART VALVE HAVING NON-CYLINDRICAL FRAME

CROSS REFERENCE TO RELATED APPLICATIONS

This application is a continuation of International Application No. PCT/US19/56865 filed on Oct. 18, 2019, which claims the benefit of U.S. Provisional Application 62/799,678 filed on Jan. 31, 2019 and U.S. Provisional Patent Application 62/748,284 filed on Oct. 19, 2018, all of which are incorporated by reference herein in their entirety.

FIELD

The present disclosure relates to implantable, mechanically expandable prosthetic devices, such as prosthetic heart valves, and to methods and assemblies for assembling collapsible frames for, and including, such prosthetic devices.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, actuating a mechanical actuator that applies an expansion force to the prosthetic valve, or by deploying the prosthetic valve from a sheath of the delivery device so that the prosthetic valve can self-expand to its functional size.

Prosthetic valves that rely on a mechanical actuator for expansion can be referred to as "mechanically expandable" prosthetic heart valves. The actuator typically takes the form of pull cables, sutures, wires and/or shafts that are configured to transmit expansion forces from a handle of the delivery apparatus to the prosthetic valve.

Most expandable, transcatheter heart valves comprise a cylindrical metal frame or stent and prosthetic leaflets mounted inside the frame. Typically, the leaflets are attached to the frame in such a manner that the articulating or coaptation edges of the leaflets are spaced radially inward of the frame to prevent leaflet abrasion when the leaflets open under the flow of blood. In such valves, the effective outflow orifice typically is narrower than the inflow orifice, resulting in eddies and turbulence downstream at the outlet of the prosthetic valve, which can produce a relatively high-pressure gradient across the prosthetic valve when the leaflets are open and blood is flowing through the prosthetic valve. The presence of additional components adjacent the outflow end of the frame, such as actuators for expanding the valve, can further increase the pressure gradient across the prosthetic valve. The increased pressure gradient can lead to prosthesis-patient-mismatch (PPM) where the prosthetic valve is essentially undersized for the patient, which has been shown to be associated with worsened hemodynamic function, more cardiac events, and lower survival rates.

Accordingly, a need exists for improved prosthetic heart valve frame designs and methods for implantation.

SUMMARY

Described herein are embodiments of improved implantable medical devices, such as prosthetic heart valves, as well as methods for implanting such devices.

An implantable prosthetic device can include a frame that is radially expandable and compressible between a radially compressed configuration and a radially expanded configuration. The frame can comprise a first set of a plurality of struts extending in a first direction, and a second set of a plurality of struts extending in a second direction. Each strut of the first set of struts can be pivotably connected to at least one strut of the second set of struts. Each strut can be curved helically with respect to a first, longitudinal axis of the frame and each strut can be curved with respect to a second axis that is perpendicular to the first, longitudinal axis of the frame.

In some embodiments, each strut can be concave with respect to an outflow end of the frame. In other embodiments, each strut can be convex with respect to an outflow end of the frame.

In some embodiments, when the frame is in a radially expanded configuration, the frame can taper from a first diameter at a first location on the frame to a second diameter at a second location on the frame axially spaced from the first location. The first diameter can be greater than the second diameter.

In some embodiments, each strut can comprise a plurality of segments between locations where struts are pivotally connected to each other. Each segment can be curved with respect to the second axis such that the strut is curved along a length of the strut. In some embodiments, each strut can comprise a plurality of segments between locations where struts are pivotally connected to each other, and each segment can be offset from each adjacent segment such that the strut is curved along a length of the strut.

In some embodiments, each strut can extend from a first end of the frame to an axially opposed second end of the frame.

In some embodiments, the implantable prosthetic device can further comprise a valve assembly comprising a plurality of leaflets mounted inside the frame.

In a representative embodiment, an implantable prosthetic device comprises a frame having first and second opposing axial ends. The frame can comprise a first set of a plurality of struts extending in a first direction, and a second set of a plurality of struts extending in a second direction. Each strut can be curved along a length of the strut and can have first and second longitudinal edges extending along the length. The first longitudinal edge can form convex curve facing the first end of the frame and the second longitudinal edge can form a concave curve facing the second end of the frame.

In some embodiments, each strut can extend from the first end of the frame to the second end. In some embodiments, a projection of each strut in a plane parallel to a longitudinal axis of the frame can be curved.

In some embodiments, the frame can have a first diameter at the first end and a second diameter at the second end. In some embodiments, when the frame is in a radially expanded configuration, the second diameter can be larger than the first diameter. In some embodiments, when the frame is in a radially compressed configuration, the second diameter can be smaller than the first diameter.

In another representative embodiment, an implantable prosthetic device, comprises a frame movable between a radially compressed configuration and a radially expanded configuration. When in the radially expanded configuration the frame can have a tapered frustoconical shape. The frame can have a first draft angle when in the radially compressed configuration and a second draft angle when in the radially expanded configuration.

In some embodiments, the first draft angle can be less than the second draft angle. In some embodiments, the first draft angle is greater than the second draft angle.

In a representative embodiment, a method can comprise placing a prosthetic valve within a sheath of a delivery apparatus. The prosthetic valve can comprise a frame having a curved inflow end portion facing in a distal direction. The method can further comprise inserting the delivery apparatus into the vasculature of a patient and advancing the delivery apparatus and the prosthetic valve through the ascending aorta and into the native aortic valve of the patient. The method can further comprise deploying the prosthetic valve from the sheath, radially expanding the prosthetic valve, radially compressing the prosthetic valve, and retracting the prosthetic valve into the ascending aorta. The prosthetic valve can then be advanced into the patient's native aortic valve while the prosthetic valve is completely outside the sheath.

In some embodiments, the frame can be shape set such that the inflow end portion curves toward a longitudinal axis of the frame at least when the frame is radially compressed.

In another representative embodiment, an implantable prosthetic device comprises a frame having first and second opposing axial ends. The frame can comprise a first set of a plurality of struts extending in a first direction, and a second set of a plurality of struts extending in a second direction. Each strut can comprise a non-Euclidian geometry.

In some embodiments, each strut can comprise an elliptic geometry. In some embodiments, each strut can comprise a hyperbolic geometry.

In yet another representative embodiment, an implantable prosthetic device comprises a frame having first and second opposing axial ends. The frame can comprise a first set of a plurality of struts extending in a first direction, and a second set of a plurality of struts extending in a second direction. Each strut of the first plurality of struts can be pivotably coupled to one or more struts of the second plurality of struts. Each strut can be plastically and elastically deformable when radially compressed such that the frame is at least partially self-expandable without permanent plastic deformation.

In a representative embodiment, a medical device assembly comprises a radially expandable and compressible prosthetic valve and a delivery apparatus. The delivery apparatus can comprise a plurality of connecting members having distal end portions releasably coupled to the prosthetic valve and a tension member connecting to the plurality of connecting members. When the prosthetic valve is in a radially expanded state, tensioning the tension member can pull the connecting members radially inwardly and cause the prosthetic valve to compress from the radially expanded state to a radially compressed state.

In some embodiments, the tension member forms a loop around the connecting members.

In some embodiments, the delivery apparatus further comprises a tension member actuator having a distal end portion coupled to the tension member and a proximal end portion coupled to a handle of the delivery apparatus. Applying a proximal directed force to the tension member actuator is effective to tension the tension member, which in turn can apply a radially directed force to the connecting members to radially compress the prosthetic valve.

In some embodiments, each connecting member can comprise a retaining member and the tension member extends through each retaining member. In some embodiments, the retaining members comprise eyelets.

In some embodiments, the tension member can be connected to the distal end portion of the tension member actuator at a location radially offset inwardly toward a longitudinally axis of the delivery apparatus.

In some embodiments, the delivery apparatus can further comprise a sheath extending coaxially over the tension member actuator.

In some embodiments, the prosthetic valve can comprise a frame and a plurality of actuators mounted to the frame and being operable to radially expand the prosthetic valve to the radially expanded state. The delivery apparatus can comprise a plurality of actuator assemblies releasably connected to the actuators of the prosthetic valve and the connecting members can be components of the actuator assemblies.

In some embodiments, the actuator assemblies can comprise actuator members releasably connected to the actuators of the prosthetic valve and the connecting members can comprise support tubes extending over the actuator members.

In some embodiments, the prosthetic valve can have a tapered shape in a partially compressed state having a first diameter at a distal end and a second diameter at a proximal end. The second diameter can be greater than the first diameter, and the tension member, when tensioned, can compress the prosthetic valve from the partially compressed state to a further compressed state in which the prosthetic valve is less tapered than in the partially compressed state.

In some embodiments, the prosthetic valve can be substantially cylindrical in the further compressed state.

In another representative embodiment, a method comprises inserting a distal end portion of a delivery apparatus into the vasculature of a patient. The distal end portion comprising a sheath and a prosthetic valve retained within the sheath in a radially compressed state. The prosthetic valve can be releasably connected to a plurality of connecting members of the delivery apparatus. The method further comprising deploying the prosthetic valve from the sheath such that the prosthetic valve partially expands to a partially expanded state and tensioning a tension member connected to the connecting members. Tensioning the tension member can cause the connecting members to move radially inwardly, which compress the prosthetic valve from the partially expanded state to a fully compressed state. The method further comprising positioning the fully compressed prosthetic valve at an implantation site.

In some embodiments, the method can further comprise radially expanding the prosthetic valve at the implantation site by actuating a plurality of actuators of the prosthetic valve, and disconnecting the connecting members from the prosthetic valve.

In some embodiments, the delivery apparatus can comprise a plurality of actuator assemblies releasably connected to the actuators of the prosthetic valve. The connecting members can be components of the actuator assemblies, and radially expanding the prosthetic valve at the implantation site can comprise actuating the actuator assemblies, which in turn actuate the actuators of the prosthetic valve.

In some embodiments, the actuator assemblies can comprise actuator members releasably connected to the actuators of the prosthetic valve, and the connecting members can comprise support tubes extending over the actuator members.

In some embodiments, the prosthetic valve can have a tapered shape in a partially expanded state having a first diameter at a distal end and a second diameter at a proximal end. The second diameter can be greater than the first diameter, and the prosthetic valve in the fully compressed state can be less tapered than in the partially expanded state after tensioning the tension member.

In some embodiments, the prosthetic valve can be substantially cylindrical in the fully compressed state.

In some representative embodiments, an implantable prosthetic device can comprise a frame that is radially expandable and compressible between a radially compressed configuration and a radially expanded configuration. The frame can comprise a first set of a plurality of struts extending in a first direction, and a second set of a plurality of struts extending in a second direction. Each strut of the first set of struts can be pivotably connected to at least one strut of the second set of struts, and each strut can be curved helically with respect to a longitudinal axis of the frame. Each strut can be concave with respect to a line extending through an inflow end and an outflow end of the frame and crossing the longitudinal axis at an arbitrary angle.

In a representative embodiment, a delivery assembly can comprise a prosthetic valve movable between a radially expanded configuration and a radially compressed configuration, a delivery apparatus, and a crimping mechanism. The delivery apparatus comprising a handle and a plurality of actuators extending distally from the handle and configured to releasably couple the prosthetic valve and to move the prosthetic valve between the radially expanded and compressed configurations. The crimping mechanism comprising a tension member actuator defining an inner lumen, and a tension member extending through the inner lumen and configured to selectively extend around the prosthetic valve. The crimping mechanism can extend distally from the handle of the delivery apparatus. The tension member actuator is configured to selectively exert an axial force on the tension member, thereby radially compressing the prosthetic valve.

In some embodiments, the crimping mechanism is movable between an exposed position and a retracted position, wherein when in the exposed position the crimping mechanism is configured to extend around a circumference of the prosthetic valve, and wherein when in the retracted position the crimping mechanism does not contact the prosthetic valve.

In some embodiments, the tension member can define a loop portion at a distal end of the tension member actuator. In some embodiments, the loop portion comprises a closed loop. In other embodiments, the loop portion comprises an open loop.

In some embodiments, the tension member can comprise a suture, a wire, a pull cable, a shaft that is configured to transmit radial compression forces from the handle of the delivery apparatus, or combinations thereof.

In some embodiments, the crimping mechanism is movable between an exposed position and a retracted position and when in the exposed position the crimping mechanism is configured to extend around the plurality of actuators.

In a representative embodiment, a method for deploying a prosthetic valve from a sheath of a delivery apparatus inside a body of a patient can comprise expanding the prosthetic valve by actuating an actuation mechanism of the delivery apparatus such that the actuation mechanism applies an expansion force to the prosthetic valve. A crimping mechanism can be deployed from within the delivery apparatus such that the crimping mechanism extends around the partially compressed prosthetic valve. The crimping mechanism can comprise a tension member actuator having a lumen and a tension member extending through the lumen of the tension member actuator. The tension member can define a loop portion at a distal end of the tension member actuator. The tension member actuator can be moved relative to the tension member such that the loop portion applies tension to a selected crimping location causing the prosthetic valve to compress from a radially expanded state to a radially compressed state.

In some embodiments, the selected crimping location is located on the prosthetic valve. In other embodiments, the selected crimping location is located on the actuation mechanism of the delivery apparatus.

In another representative embodiment, a delivery assembly can comprise a prosthetic valve movable between a radially compressed configuration and a radially expanded configuration and a delivery apparatus. The delivery apparatus comprising a handle, a shaft extending distally from the handle, the shaft having a proximal end portion and a distal end portion, a plurality of actuators coupled to the prosthetic valve and configured to move the prosthetic valve between the compressed and expanded configurations, and a nose piece coupled to the distal end portion of the shaft. The delivery apparatus further comprising a capsule coupled to a proximal end portion of the nose piece, the capsule configured to retain a distal end of a prosthetic heart valve in the compressed configuration when the prosthetic heart valve is mounted on the shaft. The capsule being configured to slide distally off of the distal end of the prosthetic heart valve when the prosthetic valve moves from the compressed configuration to the expanded configuration.

In some embodiments, the capsule comprises a fabric. The fabric can comprise polytetrafluoroethylene (PTFE), polyamine, polyurethane, polypropylene, or a combination thereof. In other embodiments, the capsule comprises a non-textile polymer membrane. The non-textile polymer membrane can comprise polytetrafluoroethylene (PTFE), polyamine, polyurethane, polypropylene, or a combination thereof.

In some embodiments, the prosthetic valve has a non-cylindrical shape when in the radially compressed configuration and when in the radially expanded configuration.

In some embodiments, the capsule extends over less than half the length of the radially compressed prosthetic valve.

In another representative embodiment, a method comprises inserting a delivery assembly comprising a delivery apparatus and a radially compressed prosthetic valve into the body of a patient. The delivery apparatus having a shaft extending distally from the handle, a nose piece coupled to a distal end portion of the shaft, and a capsule coupled to a proximal end portion of the nose piece. The capsule can be configured to retain a distal end portion of the prosthetic valve in the radially compressed configuration when the prosthetic valve is mounted on the shaft. The method further comprising advancing the delivery assembly until the radially compressed prosthetic valve is disposed at least partially within the native annulus and expanding the prosthetic valve by actuating an expansion mechanism of the delivery apparatus, causing the capsule to slide distally off of the prosthetic valve.

In some embodiments, expanding the prosthetic valve causes the prosthetic valve to form a wedge shape. In some embodiments, the capsule comprises a fabric.

In another representative embodiment, a crimping mechanism comprises a support a support tube configured to be coupled to a prosthetic valve, the support tube defining a lumen. The crimping mechanism can include a connector disposed within the lumen of the support tube and a tension member coupled to the connector and configured to extend around a circumference of the prosthetic valve. Applying a proximally directed force to the tension member actuator is effective to tension the tension member, which in turn is configured to apply a radially directed force to a frame of the prosthetic valve to radially compress the prosthetic valve.

In some embodiments, the connector comprises a coupling portion, and wherein the tension member actuator comprises a receiving portion configured to be releasably coupled to the coupling portion. In some embodiments, the coupling portion comprises threads, and the receiving portion comprises corresponding threads. In some embodiments, the tension member comprises a wire.

In another representative embodiment, a medical device assembly comprises a radially expandable and compressible prosthetic valve having a frame, a delivery apparatus, and a crimping mechanism. The delivery apparatus can comprise a handle and a plurality of actuators extending distally from the handle and configured to be releasably coupled to the prosthetic valve and to move the prosthetic valve between the radially expanded and compressed configurations. The crimping mechanism can comprise a support tube coupled to the prosthetic valve and defining a lumen, a connector comprising a coupling portion, the connector disposed within the lumen of the support tube, a tension member coupled to the connector and extending around a circumference of the prosthetic valve, and a tension member actuator extending from the handle of the delivery apparatus and configured to be releasably coupled to the connector. Applying a proximally directed force to the tension member actuator is effective to tension the tension member, which is turn applies a radially directed force to the frame of the prosthetic valve to fully compress the prosthetic valve.

In some embodiments, the tension member comprises a wire.

In some embodiments, the prosthetic valve has a tapered shape in a partially expanded state having a first diameter at a distal end and a second diameter at a proximal end, the second diameter being greater than the first diameter, and wherein the prosthetic valve in the fully compressed state is less tapered than in the partially expanded state after tensioning the tension member. In some embodiments, the prosthetic valve is substantially cylindrical in the fully compressed state.

In some embodiments, the support tube can be mounted to one of the actuators.

In some embodiments, the tension member comprises a loop that extends around the circumference of the prosthetic valve and through an opening of the connector. In some embodiments, wherein the tension member comprises a suture.

In some embodiments, the prosthetic valve comprises a sleeve on the outside of the frame and the tension member extends through the sleeve.

In another representative embodiment, a method comprises inserting a distal end portion of a delivery apparatus and a crimping mechanism into the vasculature of a patient. The distal end portion can comprise a sheath and a prosthetic valve retained within the sheath. The crimping mechanism can comprise a support tube coupled to the prosthetic valve, a connector disposed within the support tube, a tension member encircling the prosthetic valve, and a tension member actuator releasably coupled to the connector. The method can further comprise deploying the prosthetic valve from the sheath of the delivery apparatus such that the prosthetic valve at least partially expands to an at least partially expanded state, applying a proximally directed force to the tension member actuator to tension the tension member, thereby applying a radially directed force to the frame of the prosthetic valve, which compresses the prosthetic valve from the partially expanded state to a fully compressed state, and positioning the fully compressed prosthetic valve at an implantation site.

In some embodiments, the method can further comprise radially expanding the prosthetic valve to a fully expanded state at the implantation site by actuating a plurality of actuators of the prosthetic valve. In some embodiments, the method further comprises applying a proximally directed force to the tension member actuator to tension the tension member, thereby applying a radially directed force to the frame of the prosthetic valve, which compresses the prosthetic valve from the fully expanded state to a fully compressed state. In some embodiments, the method further comprises recapturing the prosthetic valve into the sheath by retracting the prosthetic valve proximally relative to the sheath and removing the delivery apparatus, prosthetic valve, and crimping mechanism from the patient's body.

The foregoing and other objects, features, and advantages of the invention will become more apparent from the following detailed description, which proceeds with reference to the accompanying figures.

BRIEF DESCRIPTION OF THE DRAWINGS

FIG. 22 is a side elevational view of the distal end portion of a delivery apparatus including a crimping mechanism in an expanded configuration, and a prosthetic valve coupled to the delivery apparatus, according to one embodiment.

FIG. 23 is a side elevational view of the delivery apparatus and prosthetic valve of FIG. 22 showing the crimping mechanism placed around the prosthetic valve.

DETAILED DESCRIPTION

Exemplary Embodiments

Described herein are embodiments of frames for use in prosthetic implants, such as prosthetic valves (e.g., prosthetic heart valves or venous valves), stents, or grafts, to name a few. The frames can comprise struts shaped to form a non-cylindrical shape when expanded. Disclosed frame shapes can reduce the pressure gradient across the prosthetic implant and/or reduce paravalvular leakage.

Prosthetic devices (e.g., prosthetic valves) disclosed herein can be radially compressible and expandable between a radially compressed configuration and a radially expanded configuration. Thus, a prosthetic device can be crimped on an implant delivery apparatus in the radially compressed configuration during delivery, and then expanded to the radially expanded configuration once the prosthetic device reaches the implantation site.

Figure 1:
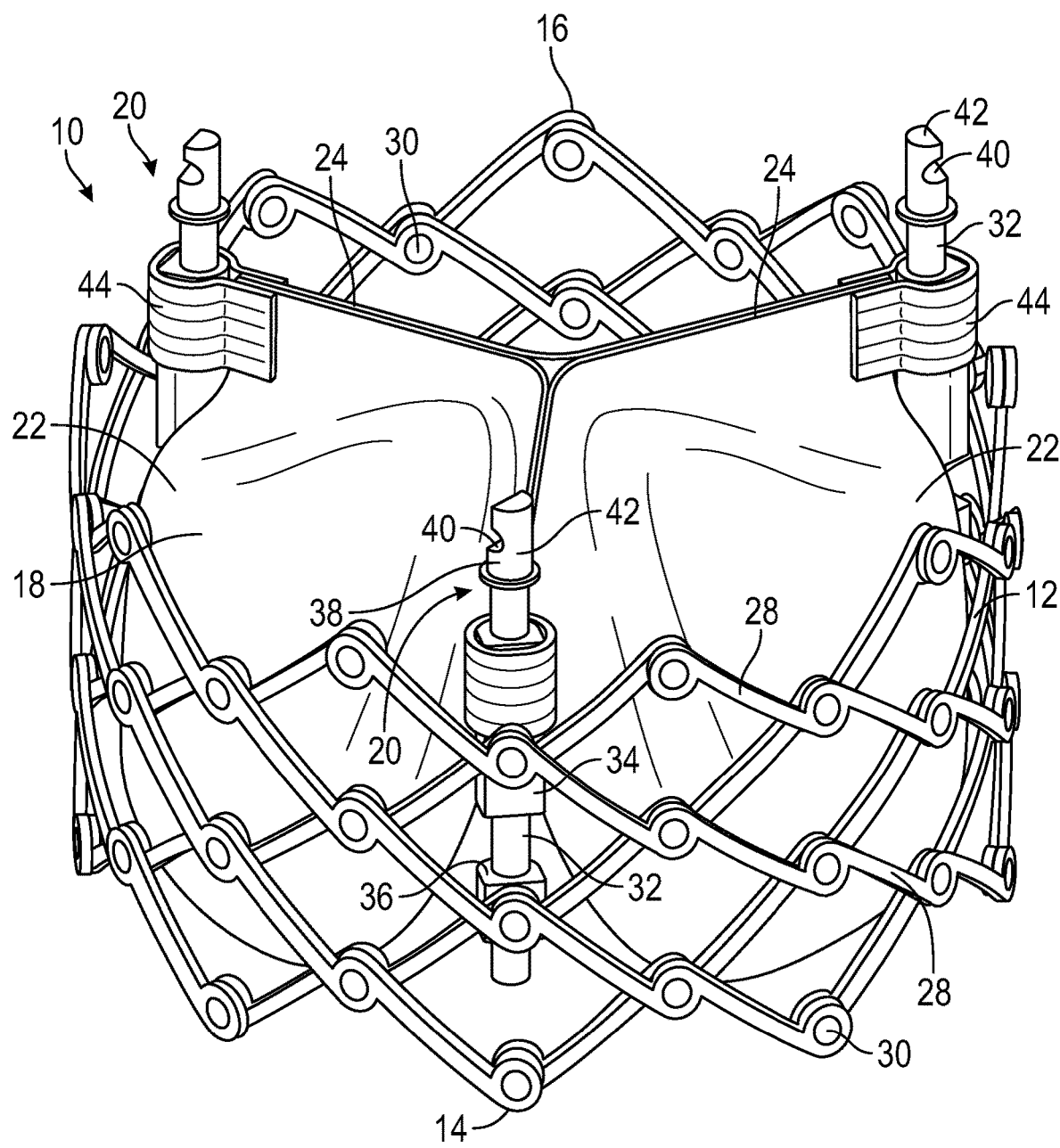
FIG. 1 is a perspective view of an embodiment of a prosthetic heart valve.

FIG. 1 shows an exemplary prosthetic valve 10, according to one embodiment. In particular embodiments, the prosthetic valve 10 can be implanted within the native aortic annulus, although it also can be implanted at other locations in the heart, including within the native mitral valve, the native pulmonary valve, and the native tricuspid valve. The prosthetic valve 10 can include an annular stent or frame 12 having a first end 14 and a second end 16. In the depicted embodiments, the first end 14 is an inflow end and the second end 16 is an outflow end. In other embodiments, the first end 14 can be an outflow end and the second end 16 can be the inflow end. The prosthetic valve 10 can also include a valvular structure 18 which is coupled to the frame 12 and configured to regulate the flow of blood through the prosthetic valve 10 from the inflow end 14 to the outflow end 16. The prosthetic valve 10 can further include one or more actuators 20 (also referred to as "expansion mechanisms") mounted to and equally spaced around the inner surface of the frame 12. Each of the actuators 20 can be configured to form a releasable connection with one or more respective actuators of a delivery apparatus, as further described below.

The valvular structure 18 can include, for example, a leaflet assembly comprising one or more leaflets 22 made of a flexible material. The leaflets 22 of the leaflet assembly can be made from in whole or part, biological material, biocompatible synthetic materials, or other such materials. Suitable biological material can include, for example, bovine pericardium (or pericardium from other sources). The leaflets 22 can be arranged to form commissures 24, which can be, for example, mounted to respective actuators 20. Further details regarding transcatheter prosthetic heart valves, including the manner in which the valvular structure can be coupled to the frame 12 of the prosthetic valve 10, can be found, for example, in U.S. Pat. Nos. 6,730,118, 7,393,360, 7,510,575, 7,993,394, and 8,652,202, and U.S. Publication No. 2018/0325665, all of which are incorporated herein by reference in their entireties.

The actuators 20 are configured to radially expand and compress the frame 12. Each of the actuators 20 can comprise a screw or threaded rod 32, a first anchor in the form of a cylinder or sleeve 34, and a second anchor in the form of a threaded nut 36. The rod 32 extends through the sleeve 34 and the nut 36. The sleeve 34 and the nut 36 can be secured to the frame 12, such as with respective fasteners that form hinges at junctions between two struts. Each actuator 20 is configured to increase the distance between the attachment locations of a respective sleeve 34 and nut 36, which causes the frame 12 to elongate axially and compress radially, and to decrease the distance between the attachment locations of a respective sleeve 34 and nut 36, which causes the frame 12 to foreshorten axially and expand radially.

For example, each rod 32 can have external threads that engage internal threads of the nut 36 such that rotation of the rod causes corresponding axial movement of the nut 36 toward or away from the sleeve 34 (depending on the direction of rotation of the rod 32). This causes the hinges supporting the sleeve 34 and the nut 36 to move closer towards each other to radially expand the frame or to move farther away from each other to radially compress the frame, depending on the direction of rotation of the rod 32.

In other embodiments, the actuators 20 can be reciprocating type actuators configured to apply axial directed forces to the frame to produce radial expansion and compression of the frame. For example, the rod 32 of each actuator can be fixed axially relative to the sleeve 34 and slidable relative to the sleeve 34. Thus, in this manner, moving the rod 32 distally relative to the sleeve 34 and/or moving the sleeve 34 proximally relative to the rod 32 radially compresses the frame. Conversely, moving the rod 32 proximally relative to the sleeve 34 and/or moving the sleeve 34 distally relative to the rod 32 radially expands the frame.

When reciprocating type actuators are used, the prosthetic valve can also include one or more locking mechanisms that retain the frame in the expanded state. The locking mechanisms can be separate components that are mounted on the frame apart from the actuators, or they can be a subcomponent of the actuators themselves. In particular embodiments, the actuators can comprise combination expansion and locking mechanism, as further described in U.S. Publication No. 2018/0153689, which is incorporated herein by reference.

Each rod 32 can include an attachment member 38 along a proximal end portion of the rod 32 configured to form a releasable connection with a corresponding actuator of a delivery apparatus. The actuator(s) of the delivery apparatus can apply forces to the rods for radially compressing or expanding the prosthetic valve 10. The attachment member 38 in the illustrated configuration comprises a notch 40 and a projection 42 that can engage a corresponding projection of an actuator of the delivery apparatus, as described in further detail below.

In the illustrated embodiments, the prosthetic valve 10 includes three such actuators 20, although a greater or fewer number of actuators could be used in other embodiments. The leaflets 22 can have commissure attachments members 44 that wrap around the sleeves 34 of the actuators 20. Further details of the actuators, locking mechanisms and delivery apparatuses for actuating the actuators can be found in U.S. Publication Nos. 2019/0060057, 2018/0153689, 2018/0153689 and 2018/0325665, each of which is incorporated herein by reference in its entirety. Any of the actuators and locking mechanisms disclosed in the previously filed applications can be incorporated in any of the prosthetic valves disclosed herein. Further, any of the delivery apparatuses disclosed in the previously filed applications can be used to deliver and implant any of the prosthetic valves discloses herein.

Although not shown in FIG. 1, the prosthetic valve 10 can also include one or more skirts or sealing members. For example, the prosthetic valve 10 can include an inner skirt mounted on the inner surface of the frame. The inner skirt can function as a sealing member to prevent or decrease perivalvular leakage, to anchor the leaflets 22 to the frame, and/or to protect the leaflets against damage caused by contact with the frame during crimping and during working cycles of the prosthetic valve. The prosthetic valve 10 can also include an outer skirt mounted on the outer surface of the frame 12 (see outer skirt 150 in FIG. 15). The outer skirt can function as a sealing member for the prosthetic valve by sealing against the tissue of the native valve annulus and helping to reduce paravalvular leakage past the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

The frame can be made of any of various suitable materials, such as stainless steel, a cobalt chromium alloy, or a nickel titanium alloy ("NiTi"), for example Nitinol. Referring again to FIG. 1, as shown, the frame 12 can include a plurality of interconnected struts 28 arranged in a lattice-type pattern. The struts 28 are shown as positioned diagonally, or offset at an angle relative to, and radially offset from, a longitudinal axis of the prosthetic valve 10 when the prosthetic valve 10 is in the expanded configuration. In other implementations, the struts 28 can be offset by a different amount than depicted in FIG. 1, or some or all of the struts 28 can be positioned parallel to the longitudinal axis of the prosthetic valve 10.

In the illustrated embodiment, the struts 28 are pivotably coupled to one another at one or more pivot joints along the length of each strut. For example, in the illustrated configuration, each of the struts 28 can be formed with apertures 110 (see e.g., FIG. 4A) at opposing ends of the strut and apertures 110 spaced along the length of the strut. Respective hinges can be formed at the locations where struts 28 overlap each other via fasteners, such as rivets or pins 30 that extend through the apertures. The hinges can allow the struts 28 to pivot relative to one another as the frame 12 is radially expanded or compressed, such as during assembly, preparation, or implantation of the prosthetic valve 10.

In some embodiments, the frame 12 can be constructed by forming individual components (e.g., the struts and fasteners of the frame) and then mechanically assembling and connecting the individual components together. In other embodiments, the struts 28 are not coupled to each other with respective hinges but are otherwise pivotable or bendable relative to each other to permit radial expansion and contraction of the frame 12. For example, the frame 12 can be formed (e.g., via laser cutting, electroforming or physical vapor deposition) from a single piece of material (e.g., a metal tube). Further details regarding the construction of the frame and the prosthetic valve are described in U.S. Publication Nos. 2018/0153689; 2018/0344456; 2019/0060057, all of which are incorporated herein by reference. Additional examples of expandable prosthetic valves that can be used with the delivery apparatuses disclosed herein are described in U.S. Publication Nos. 2015/0135506 and 2014/0296962, which are incorporated herein by reference.

Figure 2:
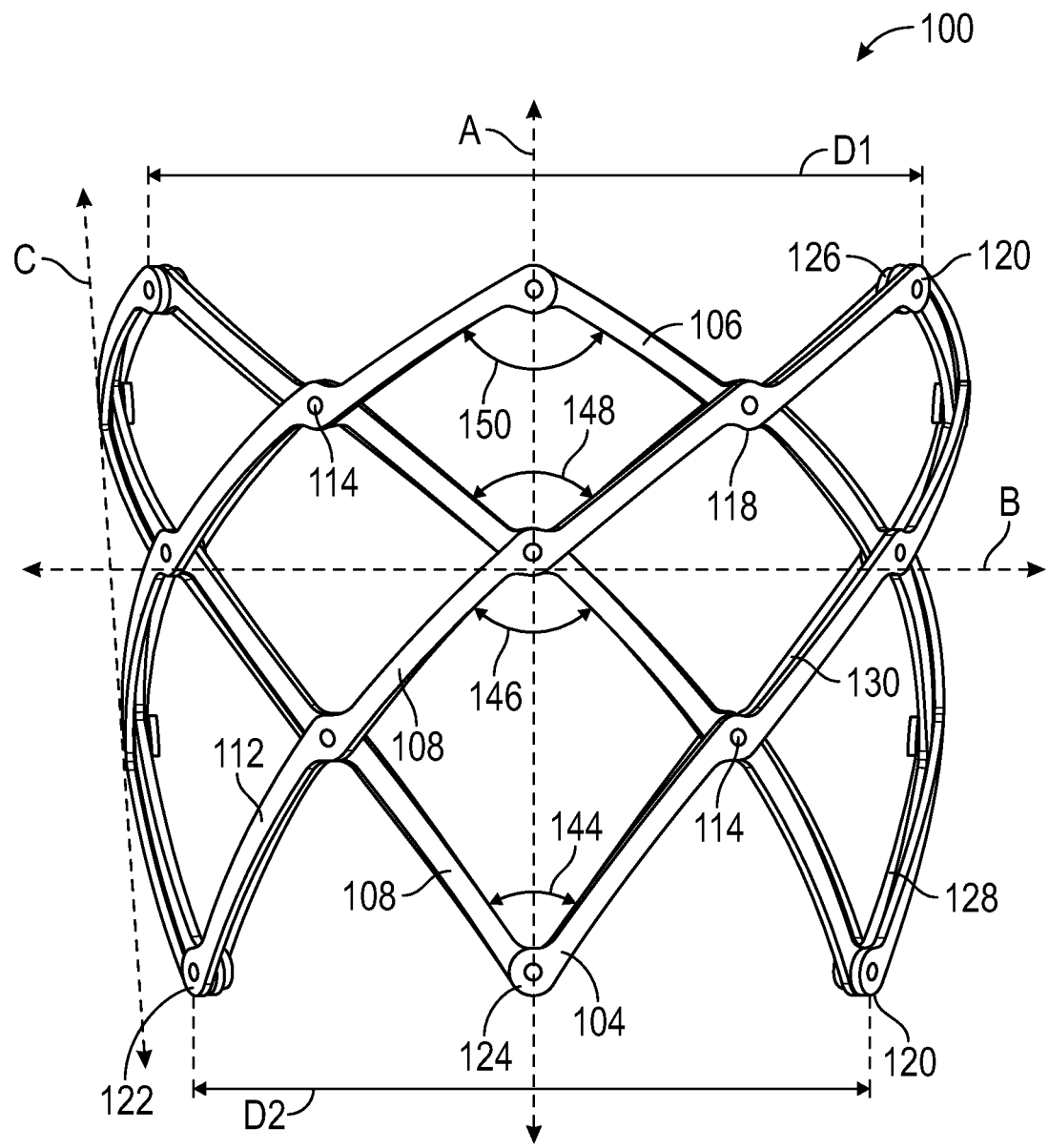
FIG. 2 is a side elevational view of a frame for a prosthetic heart valve, according to another embodiment.

FIG. 2 illustrates another embodiment of a prosthetic valve 100 comprising a frame 102 shown in its deployed, radially expanded configuration. The prosthetic valve 100 can include valvular structure (e.g., valvular structure 18), inner and/or outer skirts, and actuators (e.g., actuators 20) as previously described, although these components are omitted for purposes of illustration. The frame 102 can have an inflow end portion 104 defining an inflow end 124 of the frame and an outflow end portion 106 defining an outflow end 126 of the frame. The prosthetic valve 100 can define a longitudinal axis A extending from the inflow end portion 104 to the outflow end portion 106 and a lateral axis B extending perpendicular to the longitudinal axis A. While only one side of the frame 102 is depicted in FIG. 2, it should be appreciated that frame 102 forms an annular structure having an opposite side that is identical to the portion shown.

The frame 102 comprises a plurality of interconnected struts 108 arranged in a lattice-type pattern. Each strut can fully extend from the inflow end 124 of the frame 102 to the outflow end 126 of the frame. Thus, in the illustrated embodiment, the frame 102 can be formed entirely from struts that extend continuously from the inflow end 124 to the outflow end 126. In alternative embodiments, the frame 102 can have struts that are connected end-to-end along the length of the frame.

Figure 4A:
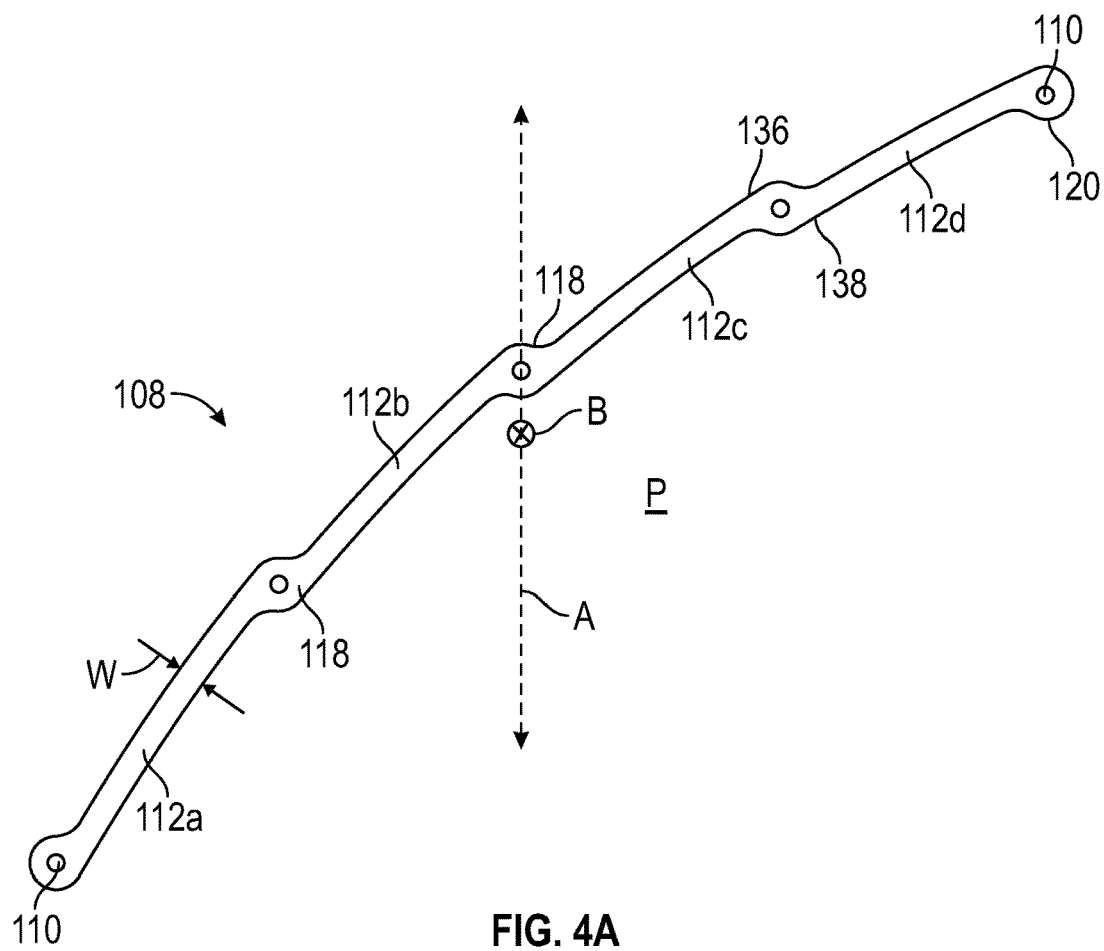
FIG. 4A is a plan view of a strut of the frame of FIG. 2 shown in a flattened configuration.

Each of the struts 108 can include a plurality of apertures 110 (see FIG. 4A). As shown in FIG. 4A, the apertures 110 can be spaced unequally along the length of each strut 108, defining a plurality of segments 112 having unequal lengths. In the illustrated embodiment, the strut 108 comprises segments 112a, 112b, 112c, and 112d, with segment 112a being the longest, and each subsequent segment 112b, 112c, and 112d having a progressively smaller length. In the assembled frame 102, the struts 108 form a plurality of closed cells arranged in a plurality of circumferentially extending rows of cells with the cells becoming progressively smaller from the inflow end 124 to the outflow end 126. In the illustrated embodiment, each strut 108 has five apertures 110 defining four segments 112 and three rows of cells, including a first row of cells 128, a second row of cells 130, and a third row of cells 132 with the cells 128 being the largest, the cells 130 being smaller than the cells 128 and the cells 132 being smaller than the cells 130.

As shown in FIG. 2, the varying lengths of the strut segments also form angles 144, 146, 148, 150 between pivotably connected struts wherein the angles progressively increase from the inflow end 124 to the outflow end 126. In alternative embodiments, one or more segments can have unequal lengths and one or more segments can have equal lengths. For example, the segment 112a can be the longest segment, segments 112b, 112c can have equal lengths, and the segment 112d can be the shortest segment.

Referring again to FIG. 4A, in the illustrated embodiment, each segment 112 has an equal width W. However, in other embodiments, the width of each segment 112 can vary along the length of the strut 108. For example, the width of segment 112a adjacent the inflow end portion 104 of the frame 102 can be greater than the width of segment 112d adjacent the outflow end portion 106 of the frame, or vice versa. In some embodiments, a strut 108 can comprise segments 112a, 112b, 112c, and 112d, with segment 112a being the widest, and each subsequent segment 112b, 112c, 112d having a progressively smaller width. In other embodiments, a strut 108 can comprise segments 112a, 112b, 112c, and 112d, with segment 112a being the narrowest, and each subsequent segment 112b, 112c, 112d having a progressively larger width.

In other embodiments, only the segments of the struts of a frame adjacent the inflow end portion 104 and the outflow end portion 106, that is, segments 112a and 112d respectively, have varying widths and the segments between the end segments can have equal widths. For example, in one embodiment, segment 112a can have a first, widest width, segments 112b and 112c can each have a second, narrower width (narrower than segment 112a), and segment 112d can have a third, narrowest width (narrower than segments 112a, 112b, and 112c). In another embodiment, segment 112a can have a first, smallest width, segments 112b and 112c can each have a second, wider width (wider than segment 112a), and segment 112d can have a third, widest width (wider than segments 112a, 112b, and 112c).

Varying the widths of the segments 112 along the strut 108 allows the frame 102 to have a tapered shape when in the radially compressed configuration. For example, in embodiments where the strut segments are narrower along the inflow end portion than along the outflow end portion (segment 112a is narrower than segment 112d), when the frame is radially compressed the inflow end portion 104 can have a diameter smaller than the diameter of the outflow end portion 106. Accordingly, when an outer skirt (e.g., skirt 150 shown in FIG. 15) is mounted on the outer surface of the inflow end portion 104 of the frame 102, the radially compressed frame 102 can have a diameter at the inflow end portion (including the outer skirt) that is substantially equal to the diameter of the frame at the outflow end portion 106. The frame and skirt combination can therefore have a substantially cylindrical shape and substantially constant diameter when radially compressed to facilitate advancement of the prosthetic valve through the patient's vasculature.

In still other embodiments, each segment 112 can have a width W that tapers along the length of the respective segment in a direction from the inflow end of the frame to the outflow end of the frame, or in a direction from the outflow end of the frame to the inflow end of the frame. For example, segment 112a can have a width that tapers along the length of the segment 112a. In some embodiments, each segment 112 can further have an average width that decreases along the length of the strut 108.

It should be understood that any of the struts and frames disclosed herein can have struts that vary in width along each segment as described above.

As shown in FIG. 2, each strut 108 can be curved helically with respect to the longitudinal axis A of the frame to define an annular shape of the frame 102. The helical curve provides each strut 108 with a concave, radial inner surface (the surface facing the longitudinal axis A) and an opposing convex, radial outer surface (the surface facing away from the longitudinal axis A).

Figure 7:
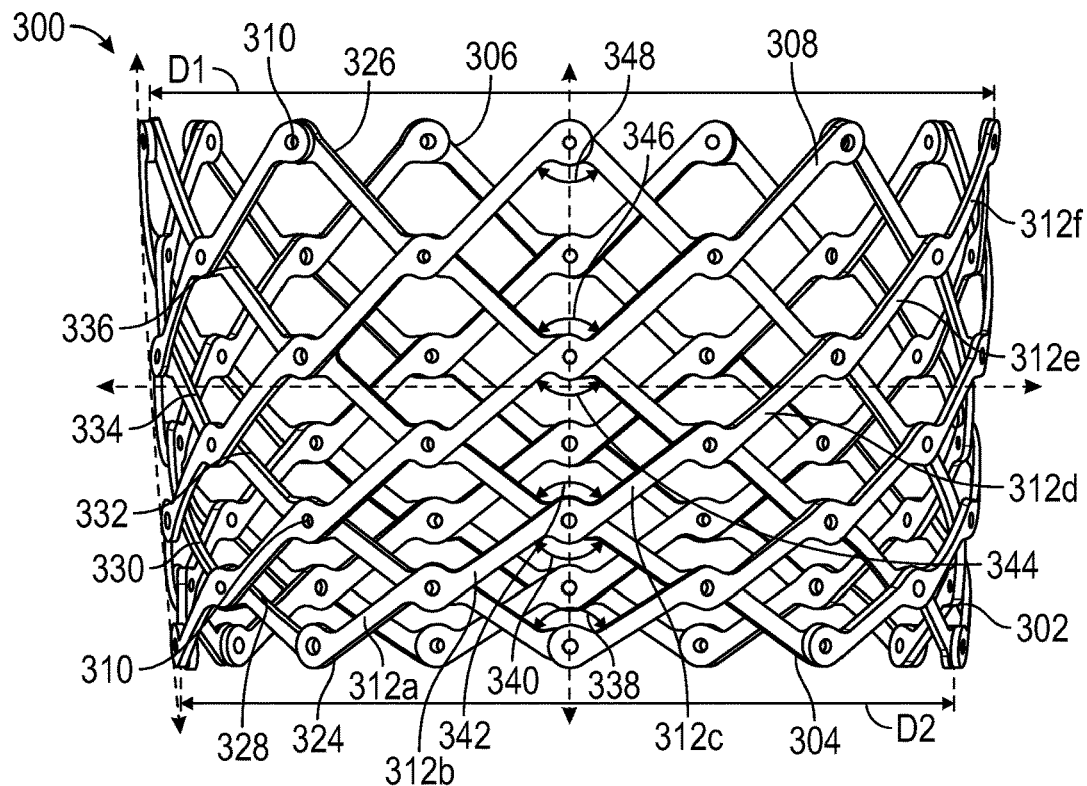
FIG. 7 is a side elevational view of another embodiment of a frame for a prosthetic heart valve shown in a fully expanded configuration.
Figure 8:
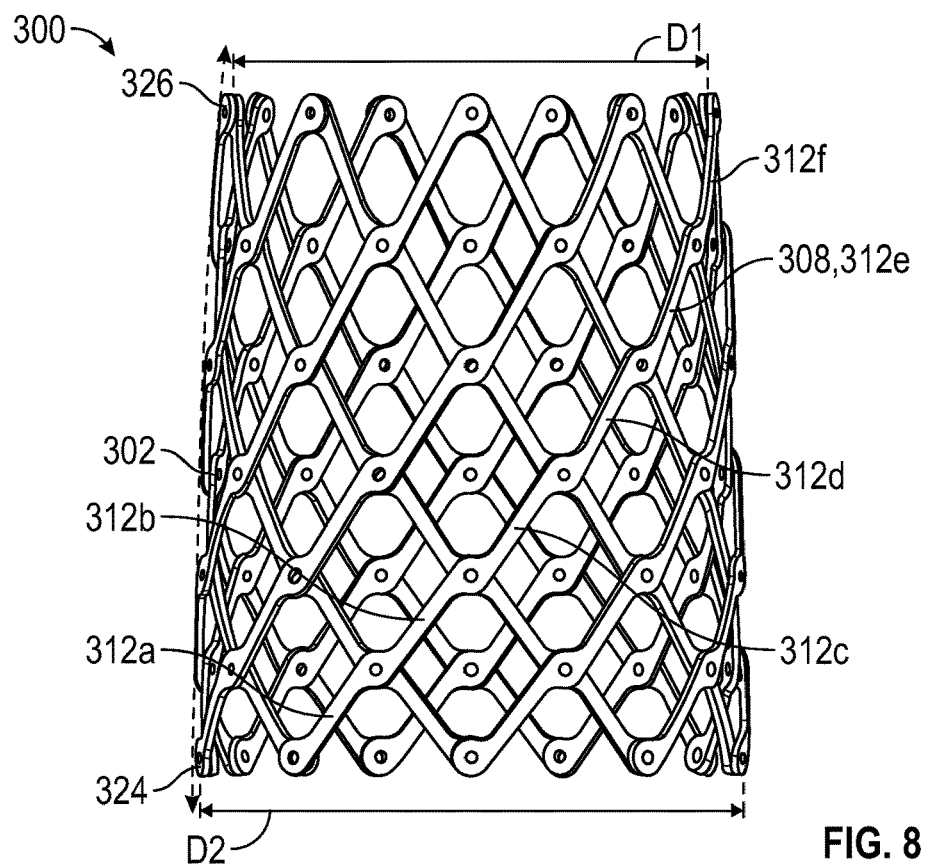
FIG. 8 is a side elevational view of the frame of FIG. 7 shown in a partially expanded configuration.
Figure 9:
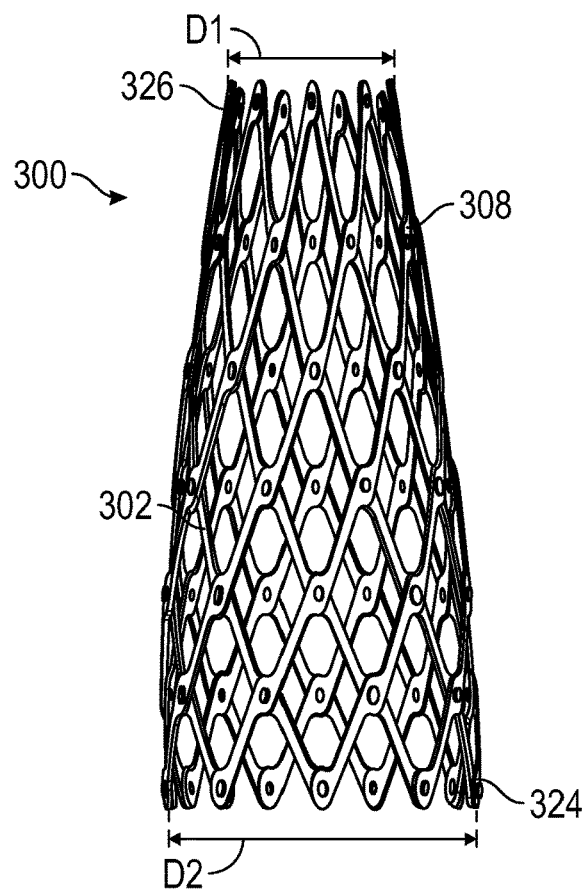
FIG. 9 is a side elevational view of the frame of FIG. 7 shown in a partially expanded configuration.

In the illustrated embodiment, each strut 108 comprises five apertures 110 defining four segments 112 and three rows of cells. In other embodiments, each strut can have a greater or fewer number of apertures to define a different number of strut segments and rows of frame cells. For example, FIGS. 7-9 show a prosthetic valve 300 (described below) wherein each strut comprises seven apertures.

Figure 3:
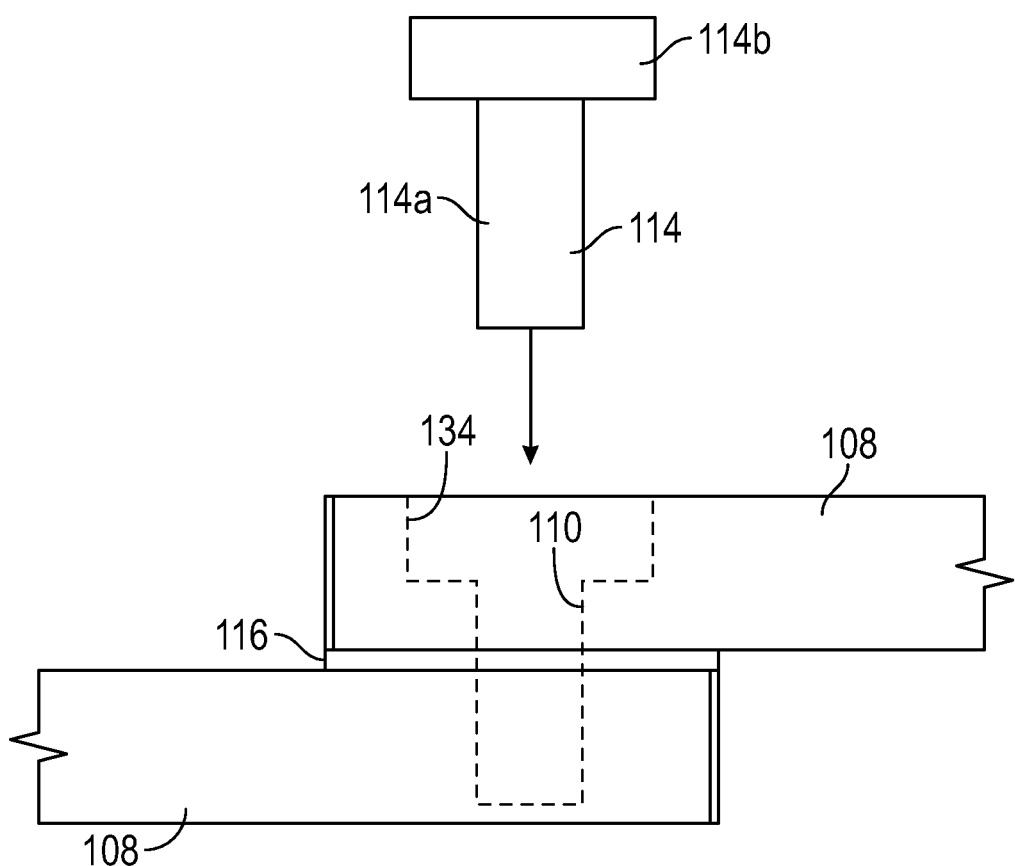
FIG. 3 is an enlarged side view showing the connection between two frame struts of the frame of FIG. 2.

With reference to FIG. 3, the apertures 110 can be used to connect the struts 108 to one another using fasteners 114, such as those described above with reference to prosthetic valve 10 (FIG. 1). Each fastener 114 can be formed with a shaft 114a and an enlarged head portion 114b. One of the apertures 110 at each hinge joint can be formed with a counter-bore 134 that is sized to receive the head portion 114b. A spacer 116, such as a washer or bushing, can be disposed in a joint between struts 108. The spacers 116 can assist the struts 108 in moving relative to one another. Further details of the struts can be found in U.S. Publication No. 2018/0344456. In other embodiments, the apertures 110, fasteners 114 and/or spacers 116 can be omitted. For example, the struts 108 can be fixedly connected to one another, such as by welding or adhesion, or by laser-cutting the individual struts of the frame from a metal tube.

FIG. 4A shows a flattened projection of a single strut 108 in a plane P parallel to the longitudinal axis A of the frame. The plane P is an XY-plane (see the coordinate system shown in FIG. 4B) from which axis B extends parallel to the Z-axis and perpendicular to the longitudinal axis A and the plane P. As shown, the segments 112 can be arranged end-to-end relative to each other with adjacent ends interconnected to each other by intermediate segments 118. The strut 108 can have enlarged (relative to segments 112) end portions 120 that form the apices 122 at the inflow and outflow ends 124, 126 of the frame 102. Each of the intermediate segments 118 and end portions 120 can have a respective aperture 110, such as at its geometric center, for receiving a fastener 114. Each segment 112 can be slightly laterally offset from an adjacent segment 112 in a direction perpendicular to the overall length of the strut 108, as shown. In alternative embodiments, the segments 112 can be arranged without any offset relative to each other.

In the illustrated embodiment, each segment 112 of the strut 108 is curved such that the overall shape of the strut 108 is curved with respect to the lateral axis B (or any line parallel to axis B and perpendicular to axis A) within the plane P. As used in the present application, a component, such as a strut or strut segment, being curved with respect to a particular axis means that the component curves around that axis and that axis is parallel to a line that is perpendicular to plane P and extends through the center of curvature of the curve. In other words, the strut 108 can be thought of as a straight bar that has been bent around axis B (which extends into and out of the plane P) to form a curve. Axis B is parallel to a line that extends through the center of curvature of the strut 108.

In particular embodiments, each strut can have a continuous and constant curve from one end of the strut to the other end of the strut. In other embodiments, the projection of each segment 112 in a plane parallel to the longitudinal axis A can be straight (i.e., each segment 112 is straight except for any helical curvature with respect to the longitudinal axis A) and the amount of offset of each segment 112 relative to an adjacent segment 112 along the length of strut 108 can vary such that the overall shape of the strut 108 is curved along its length with respect to the lateral axis B (or any line parallel to axis B and perpendicular to axis A); that is, a line extending from one end of the strut to the other end and intersecting each segment 112 is curved with respect to axis B. Alternatively, individual strut segments 112 can be straight and connected end-to-end to each other at non-zero angles such that the overall shape of the strut 108 is curved along its length with respect to the lateral axis B (or any line parallel to axis B and perpendicular to axis A). In other embodiments, one or more of the struts of a frame can have a non-constant or variable curvature along its length (in which case the center of curvature of the strut can vary as one moves along the length of the strut). For example, the radius of curvature can be greater along segments 112b, 112c and smaller along segments 112a, 112d.

Figure 4B:
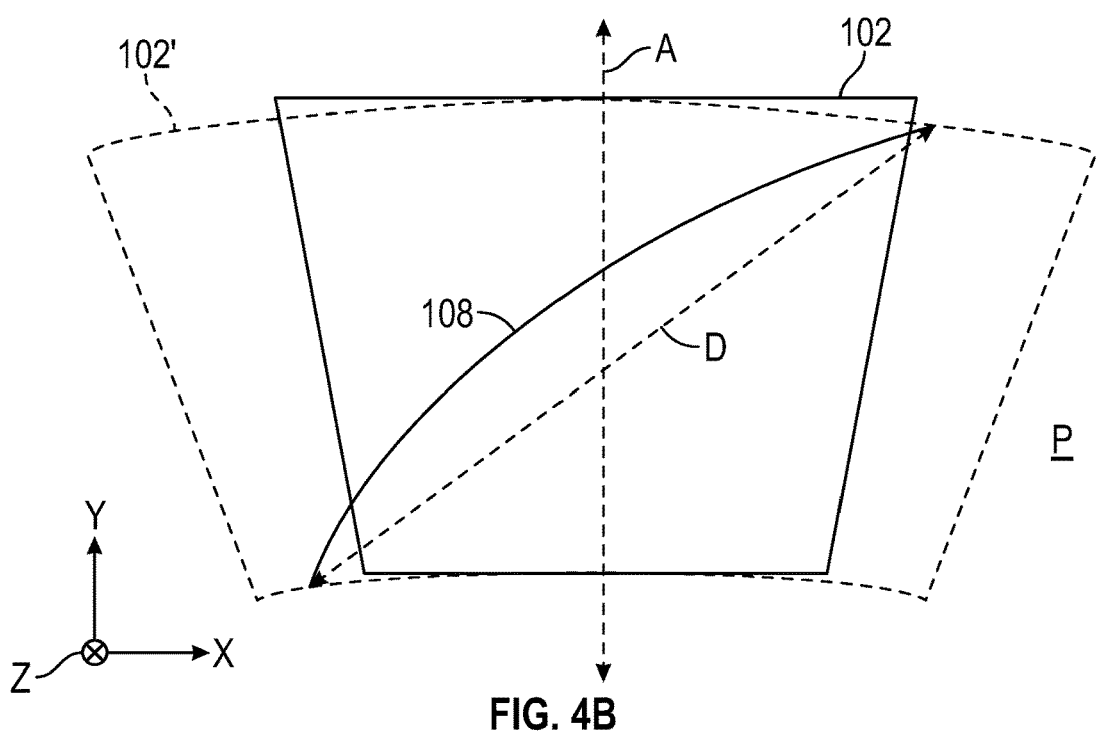
FIG. 4B is a plan view of a strut of the frame of FIG. 2 shown in a flattened configuration.

FIG. 4B shows the outline of frame 102 superimposed over frame 102', which is the frame 102 in an unrolled or unwrapped configuration in a plane P defined by the X- and Y-axes of the shown coordinate system. For any strut 108 of the frame, a diagonal line or axis D extending through the ends of the strut and the inflow and outflow ends of frame 102' can be drawn, wherein axis D forms an arbitrary angle with axis A. Each strut 108 curves away from and back toward the axis D along the length of the strut in space above the axis D. Additionally, the strut can be described as being concave with respect to the axis D.

As shown in FIG. 2, each strut 108 can be curved and arranged such that it is convex with respect to the outflow end 126 of the frame 102. As such, each strut 108 in the illustrated embodiment has a convex, first longitudinal edge 136 facing the outflow end 126 of the frame and a concave, second longitudinal edge 138 facing the inflow end 124 of the frame. Due to the unique shape of the struts 108, the frame 102 formed by the struts has a non-Euclidian geometry, and in particular, an elliptic geometry (also referred to as Riemannian geometry). The frame 102 in the illustrated embodiment therefore can be referred to as a "Riemann" frame.

The degree of curvature of a strut 108 in the plane P can be defined as the reciprocal of the radius of a circle comprising the strut as an arc, as shown in the following equation:

$$K_S = \frac{1}{R}; \qquad \text{Equation 1}$$

where $K_s$=the curvature of the strut, and R=the radius of a circle comprising the strut as an arc of the circle. In the illustrated embodiment, each strut 108 of frame 102 has the same degree of curvature in the plane P. However, in other embodiments, each strut 108 can have a differing degree of curvature in the plane P. In some embodiments (see e.g., FIGS. 7-9), due to the elasticity of the struts and the connections between overlapping struts, the degree of curvature of a strut can change during radial expansion and compression of the frame. In the radially compressed configuration, each strut can be deformed such that it has a lesser degree of curvature (each strut is straighter or straight in the plane P) than when in the radially expanded configuration (see FIG. 9).

Referring again to FIG. 2, in the expanded configuration, the curvature of the struts 108 in plane P can give the frame 102 a non-cylindrical, tapered shape (e.g., a frustoconical shape, a V-shape, or a Y-shape) wherein the outflow end 126 has a first diameter D1 larger than a second diameter D2 of the inflow end 124. The degree of taper can be referred to as the draft angle of the frame 102, which can be a measure of the angle between the longitudinal axis A and a line C drawn tangent to the outer surface of the frame. When implanted within the native annulus of a patient, the larger outflow relative to the inflow created by the tapered shape can reduce the pressure gradient across the prosthetic valve, helping to improve hemodynamics and mitigate the risk of paravalvular leakage.

In particular embodiments, the draft angle between lines A and C can be at least 2 degrees, at least 5 degrees, at least 10 degrees, at least 20 degrees, at least 30 degrees, at least 40 degrees, or at least 50 degrees. In particular embodiments, the draft angle can be between 2 and 15 degrees. In particular embodiments, the ratio of the outflow diameter D1 to the inflow diameter D2 is at least greater than 1, at least greater than 1.1, at least greater than 1.2, at least greater than 1.3, at least greater than 1.4, or at least greater than 1.5.

In some embodiments, there is a 2-3 mm difference between the outflow diameter D1 and the inflow diameter D2. In one specific example, the outflow diameter D1 is about 30 mm and the inflow diameter D2 is about 27 mm. In another example, the outflow diameter D1 is about 31.5 mm and the inflow diameter D2 is about 29 mm. In another example, the outflow diameter D1 is about 24.5 mm and the inflow diameter D2 is about 22 mm.

In some embodiments, while in the crimped or radially compressed configuration, the frame 102 can retain a tapered shape wherein the outflow end 126 has a diameter larger than a diameter of the inflow end 124 and the draft angle of the frame in the compressed configuration can be greater than the draft angle of the frame when the frame is in the expanded configuration (see, e.g., FIG. 17C, described below).

Additionally, in certain embodiments, when compressed to the radially compressed configuration, in particular embodiments, the struts 108 (or the struts of any of the frames disclosed herein) elastically deform along their length due to the pinned connections between overlapping struts (similar to the bending of a beam supported at both ends) and/or can elastically deform relative their lengthwise axes due to twisting or torsional forces applied to the struts. When the frame is retained in the radially compressed state (such as within the sheath of a delivery apparatus), the elastically deformed struts 108 place the frame in a state of tension. Thus, when released from the radially compressed state (e.g., when deployed from the sheath of a delivery apparatus), the struts provide a spring force that causes the frame to at least partially expand to its "free" or relaxed state. If needed, actuators (e.g., actuators 20) can be used to further expand the frame from the partially expanded state to the fully expanded state.

The free or relaxed state of the frame is the shape that the frame normally assumes in the absence of any outside forces acting on the frame. The relaxed state can be a fully expanded state or a partially expanded state of the frame depending on the shape of the frame and the extent of elastic deformation introduced in the struts when the frame is assembled. For example, the struts can be manufactured so as to conform to the curvature of a cylinder, such as by machining (e.g., laser cutting) the struts from a cylindrical piece of material, and then assembling the struts to each other in a manner to form a frame having a tapered shape. This induces bending and torsional strains within the struts and deforms the struts within the elastic range of the material. The elastic deformation provides a spring force that allows the frame to self-expand or revert back to its relaxed state after being released from a radially compressed state.

As noted above, the struts of the frame can be formed from various metals, including plastically deformable metals, such as stainless steel or a cobalt chromium alloy, or a super-elastic material, such as a nickel titanium alloy ("NiTi"), for example Nitinol. When formed from a plastically deformable metal, the struts 108 and the connections between the struts 108 can be configured to maintain the struts within the range of elastic deformation for the metal as the frame is compressed from the radially expanded state to the radially compressed state (and vice versa) so as to prevent plastic deformation of the frame when transitioning between the radially compressed state and the radially expanded state.

In some embodiments, the relaxed state of the frame is the fully expanded and operational state of the frame wherein the leaflets 22 can function to regulate the flow of blood through the prosthetic valve and the spring force of the struts 108 can be sufficient to produce full radial expansion of the frame from the compressed state to the expanded and operational state. In this manner, the frame 102 can fully self-expand from the compressed state to the expanded state without the use of actuators 20. However, actuators can be provided to assist in expanding the frame in cases where the native anatomy resists full expansion of the frame under its own resiliency (e.g., in cases of aortic stenosis). Regardless of whether actuators are provided, the prosthetic valve 100 can include one or more locking mechanisms (described above) that are configured to retain the frame in the expanded state.

In alternative embodiments, the relaxed state of the frame can be a partially expanded state between the fully expanded state and the radially compressed, delivery state. For example, the relaxed state of a frame 302 (described below) can be either of the partially expanded states shown in FIGS. 8-9. When the relaxed state is a partially expanded state, one or more actuators can be provided to fully expand the prosthetic valve. In still other embodiments, the frame is configured such that the struts do not elastically deform when radially compressed and therefore the struts do not provide any spring force or bias to expand the frame, in which case one or more actuators can be used to expand the frame from the radially compressed state to the fully expanded state.

Figure 17A:
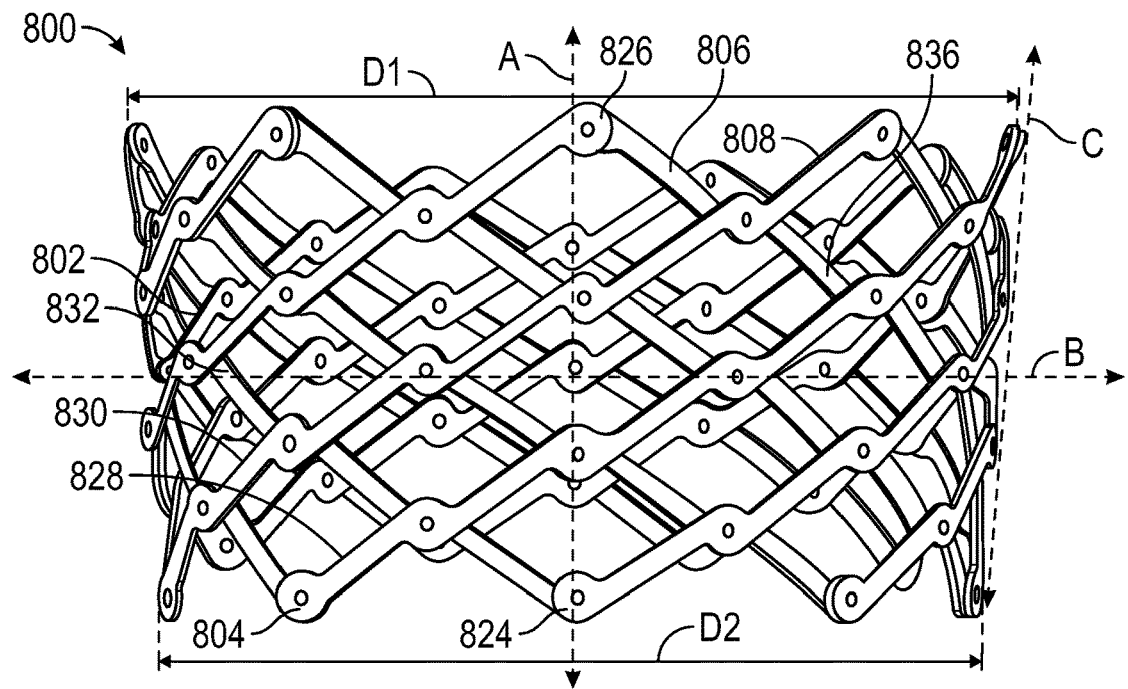
FIG. 17A is a side elevational view of another embodiment of a frame for a prosthetic heart valve shown in a fully expanded configuration.
Figure 17B:
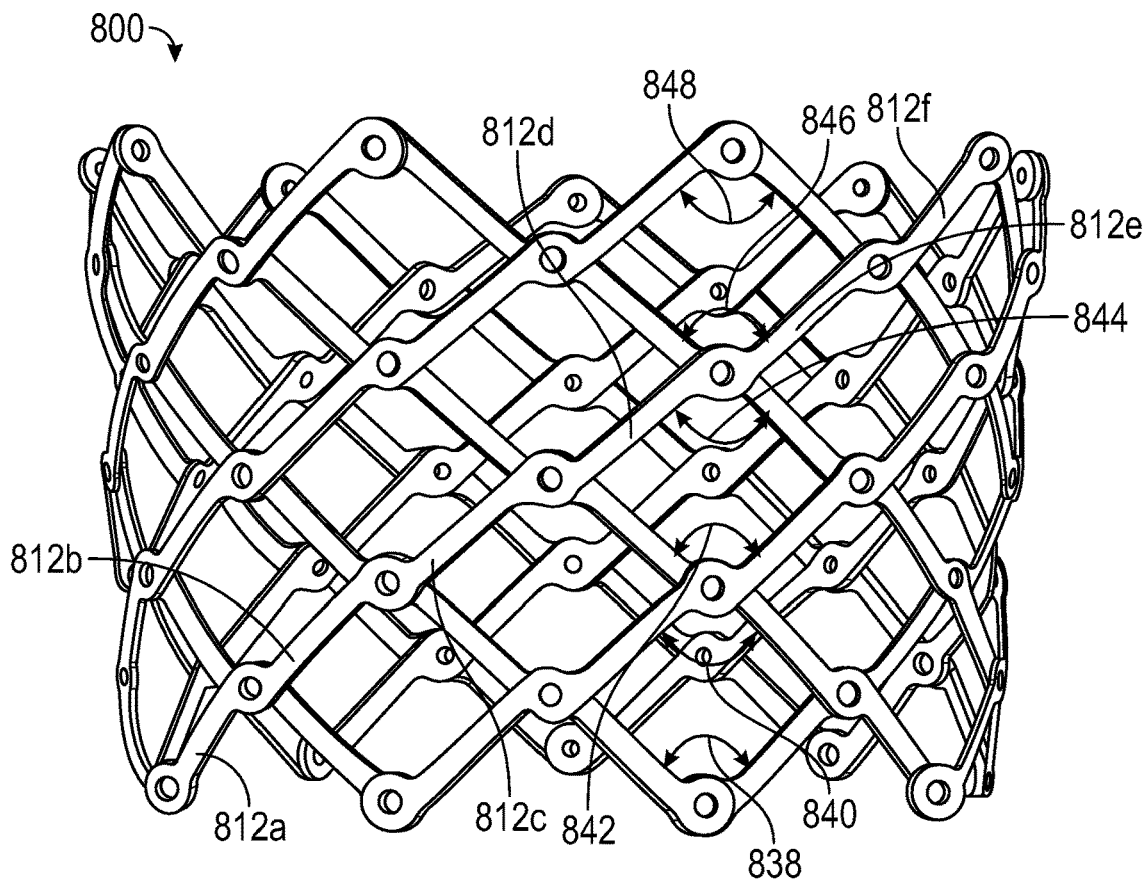
FIG. 17B is a side elevational view of the frame of FIG. 17A shown in a partially expanded configuration.
Figure 17C:
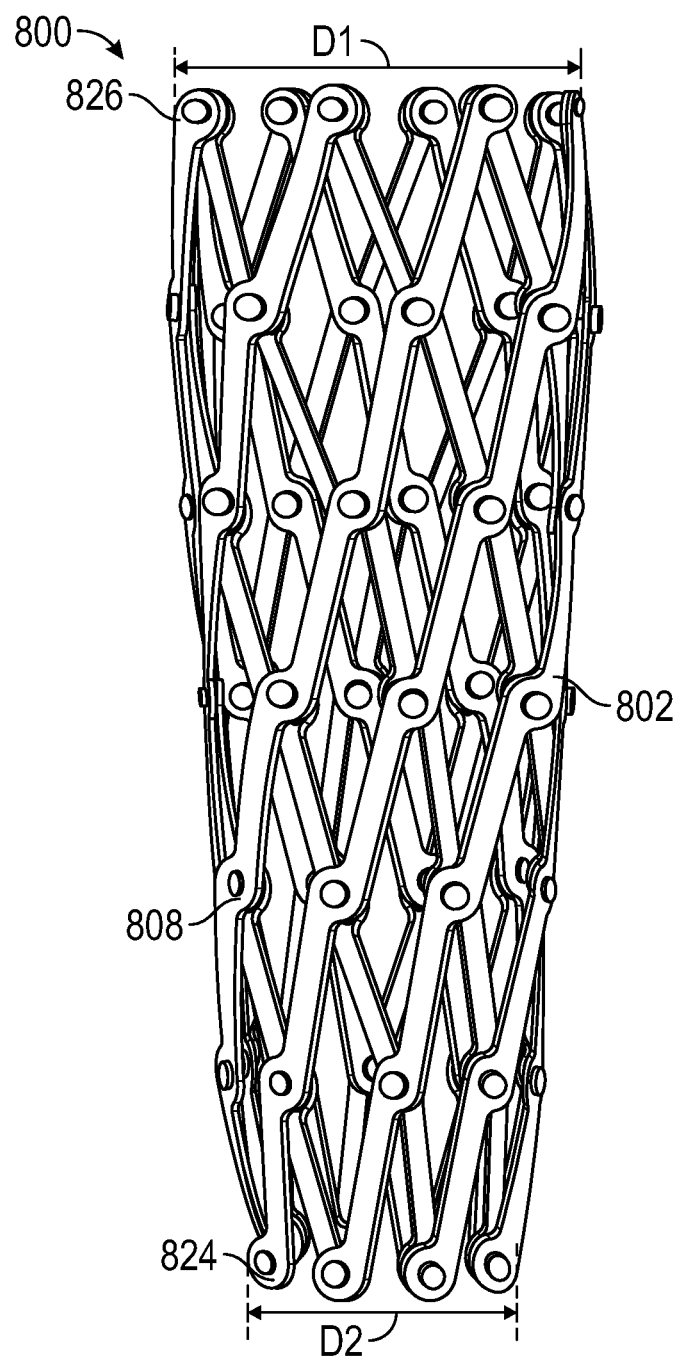
FIG. 17C is a side elevational view of the frame of FIG. 17A shown in a fully compressed configuration.

FIGS. 17A-17C illustrate a prosthetic valve 800 according to another embodiment. Prosthetic valve 800 is similar to prosthetic valve 100, except that prosthetic valve 800 has a frame 802 wherein each strut 808 comprises seven apertures 810 and therefore has more strut segments and frame cells than the struts of prosthetic valve 100. The frame 802 is another example of a Riemann frame. Like prosthetic valve 10, the prosthetic valve 800 can include a valvular structure (e.g., valvular structure 18), inner and/or outer skirts, and actuators (e.g., actuators 20) as previously described, although these components are omitted for purposes of illustration. The frame 802 can have an inflow end portion 804 defining an inflow end 824 of the frame and an outflow end portion 806 defining an outflow end 826 of the frame. The prosthetic valve can define a longitudinal axis A extending from the inflow end portion 804 to the outflow end portion 806 and a lateral axis B extending perpendicular to the longitudinal axis A.

The frame 802 comprises a plurality of interconnected struts 808 which extend from the inflow end 824 to the outflow end 826 of the frame 802. Thus, in the illustrated embodiment, the frame 802 can be formed entirely from struts that extend continuously from the inflow end 824 to the outflow end 826. In alternative embodiments, the frame 802 can have struts that are connected end-to end along the length of the frame.

Each of the struts 808 can include a plurality of apertures 810. As shown, the apertures 810 can be spaced unequally along the length of the strut 308, defining a plurality of segments 812 having unequal lengths. In the illustrated embodiment, the strut 808 comprises segments 812a, 812b, 812c, 812d, 812e, and 812f, with segment 812a being the longest, and each subsequent segment 812b, 812c, 812d, 812e, and 812f having a progressively smaller length. In the assembled frame 802, the struts 808 form a plurality of closed cells arranged in a plurality of circumferentially extending rows of cells with the cells becoming progressively smaller from the inflow end 824 to the outflow end 826. In the illustrated embodiment, each strut 808 has seven apertures 810 defining six segments 812 and five rows of cells, including a first row of cells 828, a second row of cells 830, a third row of cells 832, a fourth row of cells 834, and a fifth row of cells 836, with the cells 828 being the largest, and each row of cells becoming progressively smaller from the inflow end to the outflow end.

The varying lengths of the struts also form angles 838, 840, 842, 844, 846, 848 between pivotably connected struts, wherein the angles progressively increase from the inflow end 824 to the outflow end 826.

In alternative embodiments, one or more segments can have unequal lengths and one or more segments can have equal lengths. For example, the segment 812a can be the longest segment, segments 812b, 812c, 812d, 812e can have equal lengths, and the segment 812f can be the shortest segment. In still other embodiments, apertures 810 can be equally spaced along the length of each strut, forming segments of equal lengths. The strut 808 can further comprise segments 812 of varying widths, as described above with respect to strut 108 shown in FIG. 4A.

As shown in FIG. 17A, each strut 808 can be curved helically with respect to the longitudinal axis A of the frame to define an annular shape of the frame 802. The helical curve provides each strut with a concave, radial inner surface (the surface facing the longitudinal axis A) and an opposing convex, radial outer surface (the surface facing away from the longitudinal axis A).

The struts 808 can be connected to each other at apertures 810, for example, using fasteners, such as fasteners 114 disposed in the apertures as described above.

A flattened projection of a strut 808 in a plane P parallel to the longitudinal axis of the frame A is similar to the projection shown of strut 108 in FIG. 4A, except that strut 808 has seven apertures 810 and six segments 812. In some embodiments, each segment 812 can be straight (except for have a helical curvature with respect to the longitudinal axis A) and can be offset from adjacent segments such that the overall shape of the struts is curved along its length with respect to axis B. In other embodiments, each segment 812 can be curved to create a continuous and constant curve along the length of the strut with respect to axis B.

Each strut 808 can be curved or arranged such that it is concave with respect to the outflow end 826 of the frame 802. The degree of curvature of each strut 808 can be calculated using Equation 1 above. In the illustrated embodiment, each strut 808 has the same degree of curvature in the plane P. However, in other embodiments, each strut 808 can have a differing degree of curvature.

Referring still to FIGS. 17A-17C, due to the elasticity of the struts 808 and the connections between overlapping struts, the degree of curvature of a strut can change during radial compression and expansion of the frame. As shown in FIG. 17C, in the radially compressed configuration, each strut can be deformed such that it has a lesser degree of curvature (each strut is straighter or straight in the plane P) than when in the radially expanded configuration (see FIG. 17A).

As with prosthetic valve 100, in the expanded configuration, the curvature of the struts 808 in plane P can give the frame 802 a non-cylindrical, tapered shape (e.g., a frusto-conical shape, a V-shape, or a Y-shape) wherein the outflow end 826 has a first diameter D1 larger than a second diameter D2 of the inflow end 824. This configuration can cause the valvular structure coupled to the frame to take the shape of a cylindrical conduit without hitting or rubbing against the frame during diastole, thereby reducing the pressure gradient across the prosthetic valve 300 and improving hemodynamics.

In particular embodiments, the draft angle between lines A and C in frame 802 can be between 2 and 15 degrees. In particular embodiments, the draft angle can be at least 2 degrees, at least 5 degrees, at least 10 degrees, at least 20 degrees, at least 30 degrees, at least 40 degrees, or at least 50 degrees. In particular embodiments, the ratio of the outflow diameter D1 to the inflow diameter D2 is at least greater than 1, at least greater than 1.1, at least greater than 1.2, at least greater than 1.4, or at least greater than 1.5.

In some embodiments, there is a 2-3 mm difference between the outflow diameter D1 and the inflow diameter D2. In one specific example, the outflow diameter D1 is about 30 mm and the inflow diameter D2 is about 27 mm. In another example, the outflow diameter D1 is about 31.5 mm and the inflow diameter D2 is about 29 mm. In another example, the outflow diameter D1 is about 24.5 mm and the inflow diameter D2 is about 22 mm.

Referring to FIG. 17C, in some embodiments, while in the partially crimped or partially radially compressed configuration, the frame 802 can retain a tapered shape wherein the outflow end 826 has a diameter D1 larger than a diameter of the inflow end 824 and the draft angle of the frame in the compressed configuration can be greater than the draft angle of the frame when the frame is in the expanded configuration. The tapered shape in the partially compressed configuration can aid in the positioning and implantation of the prosthetic valve 800 at a selected implantation site. During crimping of the prosthetic valve for encapsulation within the delivery apparatus, a crimping mechanism can be used to further crimp the prosthetic valve beyond the configuration of FIG. 17C by applying force to the frame sufficient to deform the struts within the elastic and plastic deformation range of the struts, thus causing the diameter D2 at the inflow end 824 to be equal or substantially equal to the diameter D1 at the outflow end 826. This can create a "barrel shaped" valve having a shape wherein a diameter at the middle portion of the prosthetic valve 800 is slightly greater than the diameters D1, D2 at the outflow and inflow portions, respectively. In other embodiments, crimping can radially compress the prosthetic valve until it has a null draft angle, meaning the prosthetic valve in the fully compressed configuration is cylindrical.

Figure 16:
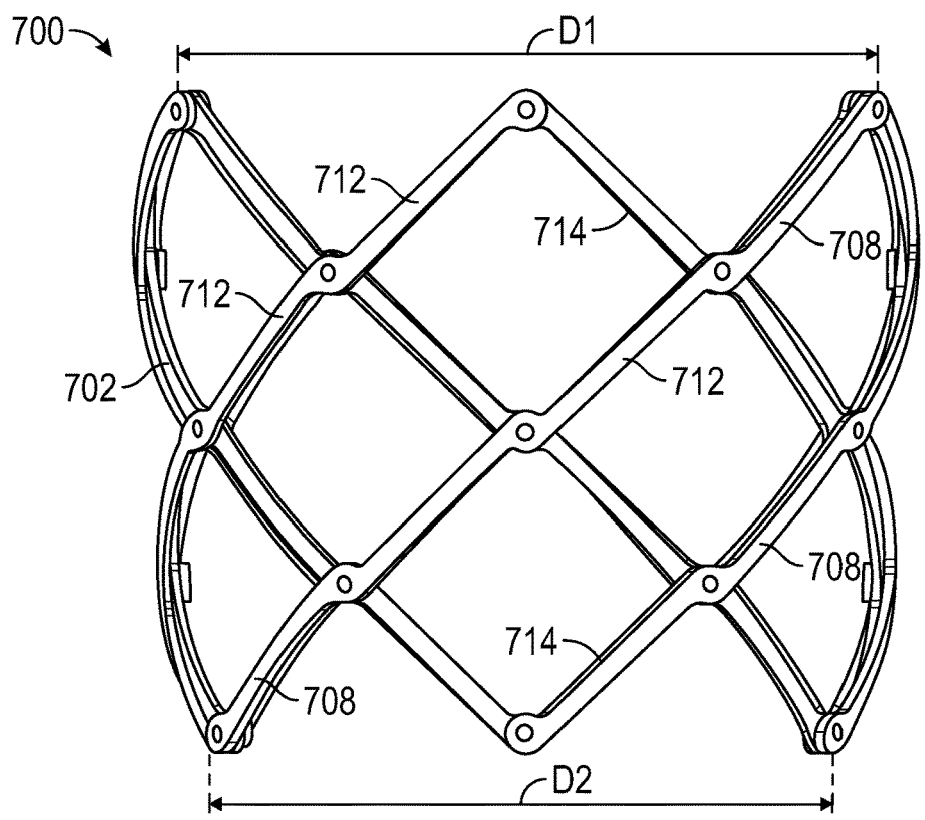
FIG. 16 is a side elevational view of another embodiment of a frame for a prosthetic heart valve.

Referring to FIG. 16, in another embodiment, a prosthetic valve 700 can have a frame 702 wherein each strut 708 has apertures 710 equally spaced along the length of each strut 708, forming segments 712 of equal lengths. The frame 702 is another example of a Riemann frame. In the assembled frame, the struts 708 form a plurality of closed cells 714 arranged in a plurality of circumferentially extending rows of cells with the cells 714 being substantially equal in size. The struts 708 can be identical to the struts 108, except for the spacing between apertures 710 and the lengths of the strut segments 712. Due to the curvature of the struts 708 (which is the same as described above for struts 108), the assembled frame 702 has an overall tapered shape defining an outflow end having a diameter D1 and an inflow end having a diameter D2 that is less than D1.

In certain embodiments, the frame 702 operates similar to frames 102 and 802 in that the draft angle of the frame 702 increases when the frame is radially compressed.

Figure 5:
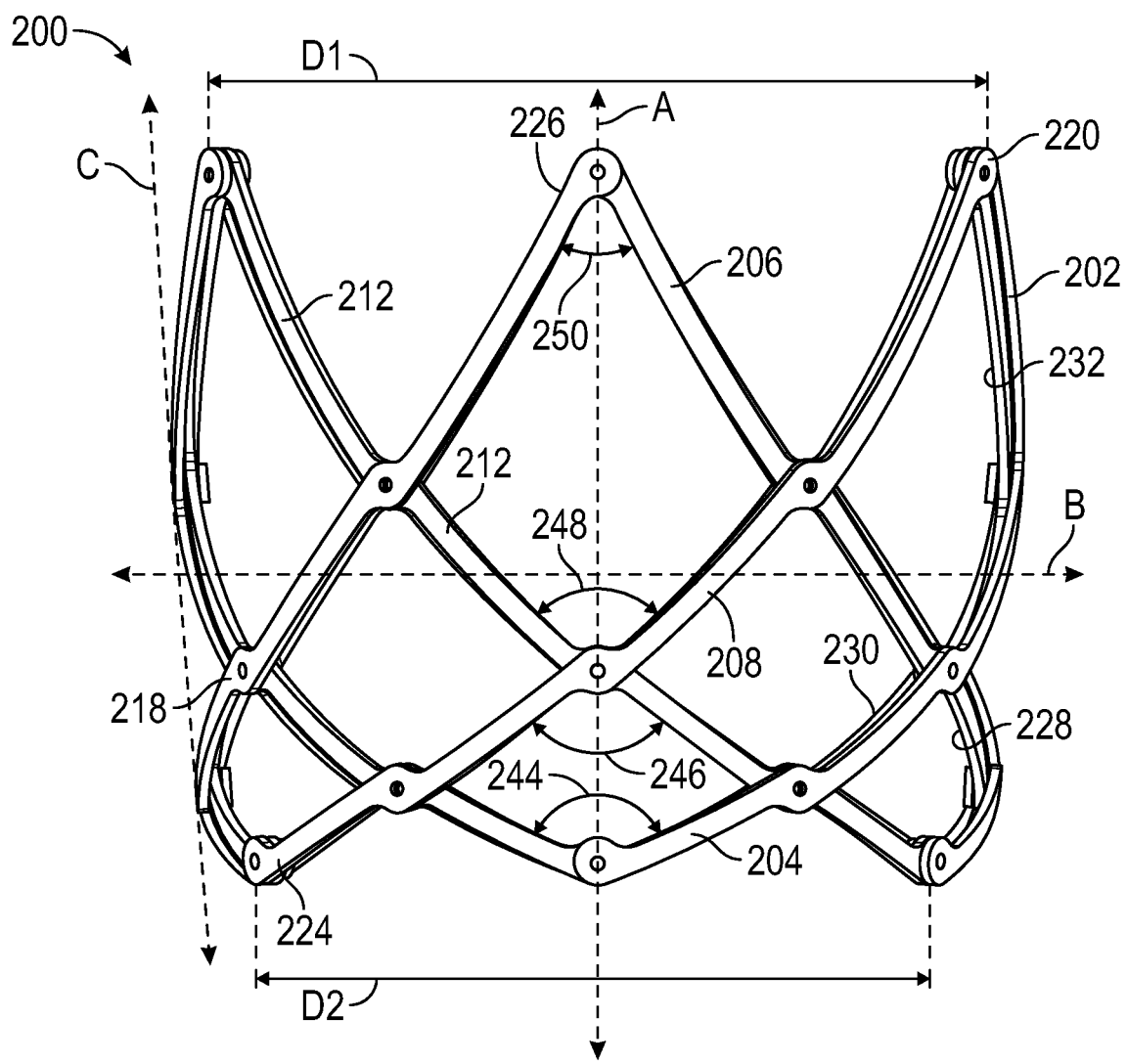
FIG. 5 is a side elevational view of another embodiment of a frame for a prosthetic heart valve.

FIG. 5 illustrates another embodiment of a prosthetic valve 200 comprising a frame 202 shown in its deployed, radially expanded configuration. Similar to prosthetic valve 10, the prosthetic valve 200 can include a valvular structure (e.g., valvular structure 18), inner and/or outer skirts, and actuators (e.g., actuators 20) as previously described, although these components are omitted for purposes of illustration. The frame 202 can have an inflow end portion 204 defining an inflow end 224 of the frame and an outflow end portion 206 defining an outflow end 226 of the frame. The prosthetic valve 200 can define a longitudinal axis A extending from the inflow end portion 204 to the outflow end portion 206 and a lateral axis B extending perpendicular to the longitudinal axis A. While only one side of the frame 202 is depicted in FIG. 5, it should be appreciated that frame 202 forms an annular structure having an opposite side that is identical to the portion shown.

The frame 202 comprises a plurality of interconnected struts 208 arranged in a lattice-type pattern. Each strut 208 can fully extend from the inflow end 224 of the frame 202 to the outflow end 226 of the frame. Thus, in the illustrated embodiment, the frame 202 can be formed entirely from struts that extend continuously from the inflow end 224 to the outflow end 226. In alternative embodiments, the frame 202 can have struts that are connected end-to-end along the length of the frame.

Figure 6A:
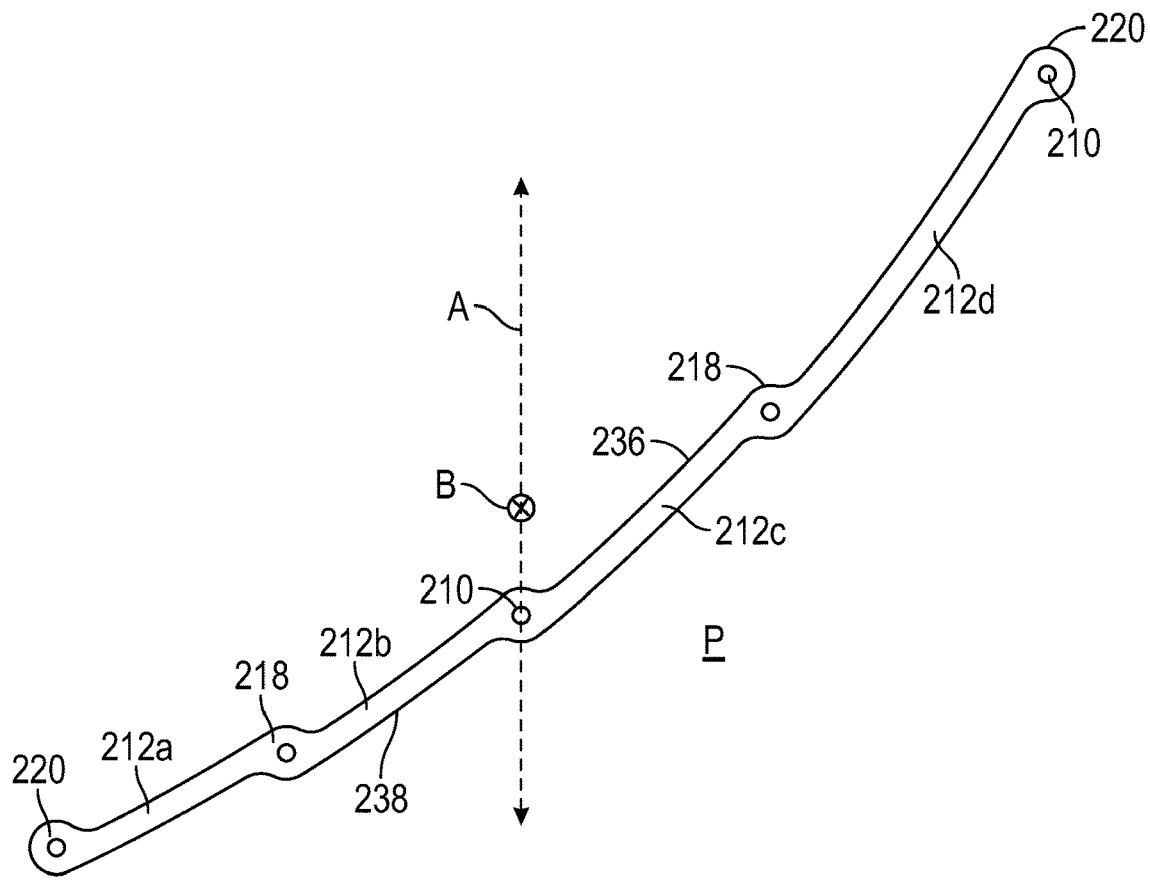
FIG. 6A is a plan view of a strut of the frame of FIG. 5 shown in a flattened configuration.

FIG. 6A shows a flattened projection of a single strut 208 of the prosthetic valve 200 in a plane P parallel to the longitudinal axis A of the frame. Plane P is an XY plane defined by coordinate axes X and Y (see the coordinate system shown in FIG. 6B) from which axis B extends parallel to the longitudinal axis A and the plane P. The longitudinal axis A can be parallel to the coordinate Y-axis and the lateral axis B can be parallel to the coordinate Z-axis. The struts 208 of the prosthetic valve 200 are similar to the struts 108 of the prosthetic valve 100, having apertures 210, segments 212, intermediate segments 218, and end portions 220, except that the struts 208 of the prosthetic valve 200 are arranged and curved such that they are concave with respect to the outflow end portion 206 of frame 202. The strut 208 can further comprise segments 212 of varying widths, as described above with respect to strut 108 shown in FIG. 4A.

In the illustrated embodiment, the strut 208 comprises segments 212a, 212b, 212c, and 212d, with segment 212a being the smallest, and each subsequent segment 212b, 212c and 212d having a progressively longer length. In the assembled frame 202, the struts 208 form a plurality of closed cells arranged in a plurality of circumferentially extending rows of cells with the cells becoming progressively larger from the inflow end 224 to the outflow end 226. In the illustrated embodiment, each strut 208 has five apertures 210 defining four segments 212 and three rows of cells, including a first row of cells 228, a second row of cells 230, and a third row of cells 232 with the cells 228 being the smallest, the cells 230 being larger than the cells 228 and the cells 232 being larger than the cells 230.

The varying lengths of the strut segments also form angles 244, 246, 248, 250 between pivotably connected struts wherein the angles progressively decrease from the inflow end 224 to the outflow end 226.

In alternative embodiments, one or more segments can have unequal lengths and one or more segments can have equal lengths. For example, the segment 212a can be the shortest segment, segments 212b, 212c can have equal lengths, and the segment 212d can be the longest segment. In still other embodiments, the apertures 210 can be equally spaced along the length of each strut, forming segments of equal lengths.

As shown in FIG. 5, each strut 208 can be curved helically with respect to the longitudinal axis A of the frame to define an annular shape of the frame 202. The helical curve provides each strut 208 with a concave, radial inner surface (the surface facing the longitudinal axis A) and an opposing convex, radial outer surface (the surface facing away from the longitudinal axis A).

In the illustrated embodiment, each strut 208 comprises five apertures 210 defining four segments 212 and three rows of cells. In other embodiments, each strut can have a greater or fewer number of apertures to define a different number of strut segments and rows of frame cells.

The struts 208 can be connected to each other at apertures 210, for example, using fasteners, such as fasteners 114 disposed in the apertures as described above.

Referring again to FIG. 6A, as shown, the segments 212 can be arranged end-to-end relative to each other and connected by intermediate segments 218 and ending in end portions 220 at the inflow and outflow ends 224, 226 of the frame 202. Each segment 212 can be slightly laterally offset from an adjacent segment 112 in a direction perpendicular to the overall length of the strut 208, as shown. In alternative embodiments, the segments 212 can be arranged without any lateral offset relative to each other.

In the illustrated embodiment, each segment 212 of the strut 208 is curved such that the overall shape of the strut 208 is curved with respect to the lateral axis B (or any line parallel to axis B and perpendicular to axis A) within the plane P. In particular embodiments, each strut can have a continuous and constant curve from one end of the strut to the other end of the strut. In other embodiments, the projection of each segment 112 in plane P can be straight (i.e., each segment 212 is straight except for any helical curvature with respect to the longitudinal axis A) and the amount of offset of each segment 212 relative to an adjacent segment 212 along the length of strut 208 can vary such that the overall shape of the strut 208 is curved with respect to the lateral axis B. In other embodiments, one or more struts of a frame can have a non-constant or variable curvature along its length (in which case the center of curvature of the strut can vary as one moves along the length of the strut). For example, the radius of curvature can be greater along segments 212b, 212c and smaller along segments 212a, 212d.

Figure 6B:
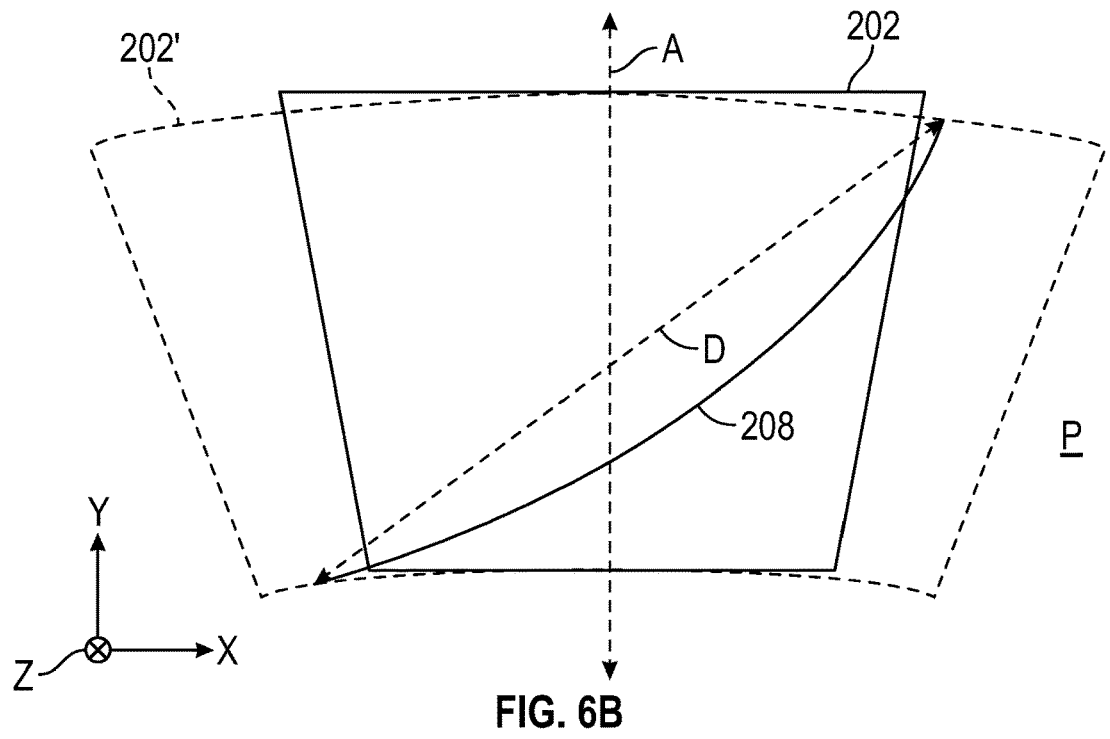
FIG. 6B is a plan view of a strut of the frame of FIG. 5 shown in a flattened configuration.

FIG. 6B shows the outline of frame 202 superimposed over frame 202', which is the frame 202 in an unrolled or unwrapped configuration in a plane P defined by the X- and Y-axes of the coordinate system. For any strut 208 of this frame, a diagonal line or axis D extending through the ends of the strut and the inflow and outflow ends of the frame 202' can be drawn, wherein axis D forms an arbitrary angle with axis A. Each strut 208 curves away from and back toward the axis D along the length of the strut in the space below the axis D. Additionally, the strut 208 can be described as being concave with respect to the axis D.

As shown in FIG. 5, each strut 208 can be curved or arranged such that it is concave with respect to the outflow end 226 of the frame 202. As such, each strut 208 in the illustrated embodiment has a concave, first longitudinal edge 236 facing the outflow end 226 of the frame and a convex, second longitudinal edge 238 facing the inflow end 224 of the frame 202. Each strut 208 can have a non-Euclidian geometry, and in particular, a hyberbolic geometry (also referred to as Lobachevsky geometry). The frame 202 in the illustrated embodiment therefore can be referred to as a "Lobachevsky" frame.

One advantage provided by the struts 208 having a concave curvature with respect to the outflow end of the frame is that the shape of the struts generally correspond to the curvature of the cusp (inflow) edges 33 (see FIG. 1) of the leaflets 22. Thus, the struts 208 allow for a more secure attachment of the cusp edges 33 to the frame.

The degree of curvature of a strut 208 of prosthetic valve 200 in plane P can be determined using Equation 1, described above with reference to prosthetic valve 100.

In the expanded configuration, the curvature of the struts 208 in plane P can give the frame 202 a non-cylindrical, tapered shape (e.g., a frustoconical shape, a V-shape, or a Y-shape) wherein the outflow end 226 has a first diameter D1 larger than a second diameter D2 of the inflow end 224. The frame 202 can have a draft angle as described above with reference to the frame 102.

In particular embodiments, the draft angle between lines A and C in frame 202 can be between 2 and 15 degrees. In particular embodiments, the draft angle can be at least 2 degrees, at least 5 degrees, at least 10 degrees, at least 20 degrees, at least 30 degrees, at least 40 degrees, or at least 50 degrees. In particular embodiments, the ratio of the outflow diameter D1 to the inflow diameter D2 is at least greater than 1, at least greater than 1.1, at least greater than 1.2, at least greater than 1.4, or at least greater than 1.5.

In some embodiments, there is a 2-3 mm difference between the outflow diameter D1 and the inflow diameter D2. In one specific example, the outflow diameter D1 is about 30 mm and the inflow diameter D2 is about 27 mm. In another example, the outflow diameter D1 is about 31.5 mm and the inflow diameter D2 is about 29 mm. In another example, the outflow diameter D1 is about 24.5 mm and the inflow diameter D2 is about 22 mm.

In some embodiments, while in the crimped or radially compressed configuration, the frame 202 can have a tapered shape wherein the diameter D1 of the outflow end 226 is smaller than the diameter D2 of the inflow end 224, giving the radially compressed frame 202 a negative draft angle. In other words, when the frame 202 is in the radially expanded state, the frame tapers in a direction from the outflow end 226 to the inflow end 224. When the frame 202 is in the radially compressed state, the frame tapers from the inflow end 224 to the outflow end 226. Because the direction of the taper changes when the frame is radially compressed, the draft angle (the angle between lines A and C) changes from a positive angle to a negative angle when measured from the same origin at the intersection of lines A and C.

Additionally, as described above with respect to frame 102, when compressed to the radially compressed configuration, in particular embodiments, the struts 208 in particular embodiments can elastically deform along their lengths due to the pinned connections between overlapping struts, similar to the bending of a beam supported at both ends. When the frame is retained in the radially compressed state (such as within the sheath of a delivery apparatus), the elastically deformed struts 208 place the frame 202 in a state of tension. Thus, when released from the radially compressed state (e.g., when deployed from the sheath of a delivery apparatus), the struts provide a spring force that causes the frame to at least partially expand. If needed, actuators (e.g., actuators 20) can be used to further expand the frame to the fully expanded state. As noted above, the struts of the frame can be formed from various metals, including plastically deformable metals, such as stainless steel or a cobalt chromium alloy, or a super-elastic material, such as a nickel titanium alloy ("NiTi"), for example Nitinol. When formed from a plastically deformable metal, the struts 208 and the connections between the struts 208 can be configured to maintain the struts within the range of elastic deformation for the metal as the frame is compressed from the radially expanded state to the radially compressed state (and vice versa) so as to prevent plastic deformation of the frame when transitioning between the radially compressed state and the radially expanded state.

In some embodiments, the spring force of the struts 208 can be sufficient to produce full radial expansion of the frame from the compressed state to an expanded and operational state wherein the leaflets 22 can function to regulate the flow of blood through the prosthetic valve. In this manner, the frame 202 can fully self-expand from the compressed state to the expanded state without the use of actuators 20. The prosthetic valve 200 can include one or more locking mechanisms (described above) that are configured to retain the frame in the expanded state.

FIGS. 7-11 illustrate another embodiment of a prosthetic valve 300. The prosthetic valve 300 is similar to the prosthetic valve 200 except that the prosthetic valve 300 has a frame 302 wherein each strut 308 comprises seven apertures 310 and therefore has more strut segments and frame cells than the struts of prosthetic valve 200. The frame 302 is another example of a Lobachevsky frame. Similar to prosthetic valve 10, the prosthetic valve 300 can include a valvular structure (e.g., valvular structure 18), inner and/or outer skirts, and actuators (e.g., actuators 20) as previously described, although these components are omitted for purposes of illustration. The frame 302 can have an inflow end portion 304 defining an inflow end 324 of the frame and an outflow end portion 306 defining an outflow end 326 of the frame. The prosthetic valve can define a longitudinal axis A extending from the inflow end portion 304 to the outflow end portion 306 and a lateral axis B extending perpendicular to the longitudinal axis A.

The frame 302 comprises a plurality of interconnected struts 308 which extend from the inflow end 324 to the outflow end 326 of the frame 302. Thus, in the illustrated embodiment, the frame 302 can be formed entirely from struts that extend continuously from the inflow end 324 to the outflow end 326. In alternative embodiments, the frame 302 can have struts that are connected end-to end along the length of the frame.

Each of the struts 308 can include a plurality of apertures 310. As shown, the apertures 310 can be spaced unequally along the length of the strut 308, defining a plurality of segments 312 having unequal lengths. In the illustrated embodiment, the strut 308 comprises segments 312a, 312b, 312c, 312d, 312e, and 312f, with segment 312a being the shortest, and each subsequent segment 312b, 312c, 312d, 312e, and 312f having a progressively larger length. In the assembled frame 302, the struts 308 form a plurality of closed cells arranged in a plurality of circumferentially extending rows of cells with the cells becoming progressively larger from the inflow end 324 to the outflow end 326. In the illustrated embodiment, each strut 308 has seven apertures 310 defining six segments 312 and five rows of cells, including a first row of cells 328, a second row of cells 330, a third row of cells 332, a fourth row of cells 334, and a fifth row of cells 336, with the cells 328 being the smallest, and each row of cells becoming progressively larger from the inflow end to the outflow end.

The varying lengths of the struts also form angles 338, 340, 342, 346, 348 between pivotably connected struts, wherein the angles progressively decrease from the inflow end 324 to the outflow end 326.

In alternative embodiments, one or more segments can have unequal lengths and one or more segments can have equal lengths. For example, the segment 312*a* can be the shortest segment, segments 312*b*, 312*c*, 312*d*, 312*e* can have equal lengths, and the segment 312*f* can be the longest segment. In still other embodiments, apertures 310 can be equally spaced along the length of each strut, forming segments of equal lengths.

As shown in FIG. 7, each strut 308 can be curved helically with respect to the longitudinal axis A of the frame to define an annular shape of the frame 302. The helical curve provides each strut with a concave, radial inner surface (the surface facing the longitudinal axis A) and an opposing convex, radial outer surface (the surface facing away from the longitudinal axis A).

Apertures 310 can be used to connect the struts 308 to one another using fasteners, such as fasteners 114 as described above.

A flattened projection of a strut 308 in a plane P parallel to the longitudinal axis of the frame A is similar to the projection shown of strut 208 in FIG. 6A, except that strut 308 has seven apertures 310 and six segments 312. In some embodiments, each segment 312 can be straight (except for having a helical curvature with respect to the longitudinal axis A) and can be offset from the adjacent segments such that the overall shape of the strut is curved along its length with respect to axis B. In other embodiments, each segment 312 can be curved to create continuous and constant curve along the length of the strut with respect to axis B.

Each strut 308 can be curved or arranged such that it is concave with respect to the outflow end 326 of the frame 302. The degree of curvature of each strut 308 can be calculated using Equation 1 above. In the illustrated embodiment, each strut 308 has the same degree of curvature in the plane P. However, in other embodiments, each strut 308 can have a different degree of curvature.

Figure 10:
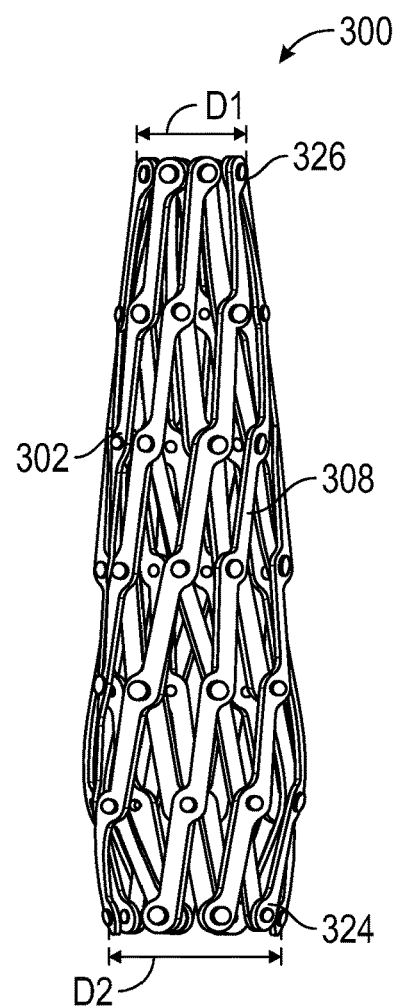
FIG. 10 is a side elevational view of the frame of FIG. 7 shown in a fully compressed configuration.
Figure 11:
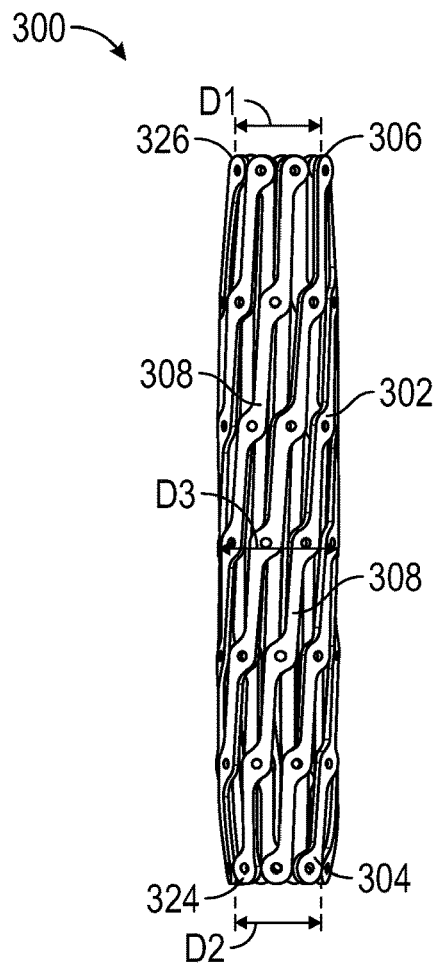
FIG. 11 is a side elevational view of the frame of FIG. 7 shown in a force-crimped configuration.

Referring still to FIGS. 7-11, due to the elasticity of the struts 308 and the connections between overlapping struts, the degree of curvature of a strut can change during radial compression and expansion of the frame. As shown in FIG. 11, in the radially compressed configuration, each strut can be deformed such that it has a lesser degree of curvature (each strut is straighter or straight in the plane P) than when in the radially expanded configuration (see FIG. 7).

As with prosthetic valves 100 and 200, in the expanded configuration, the curvature of the struts 308 in plane P can give the frame 302 a non-cylindrical, tapered shape (e.g., a frustoconical shape, a V-shape, or a Y-shape) wherein the outflow end 326 has a first diameter D1 larger than a second diameter D2 of the inflow end 324. This configuration can reduce the pressure gradient across the prosthetic valve 300 and improve hemodynamics.

In particular embodiments, the draft angle between lines A and C in frame 802 can be between 2 and 15 degrees. In particular embodiments, the draft angle can be at least 2 degrees, at least 5 degrees, at least 10 degrees, at least 20 degrees, at least 30 degrees, at least 40 degrees, or at least 50 degrees. In particular embodiments, the ratio of the outflow diameter D1 to the inflow diameter D2 is at least greater than 1, at least greater than 1.1, at least greater than 1.2, at least greater than 1.4, or at least greater than 1.5.

In some embodiments, there is a 2-3 mm difference between the outflow diameter D1 and the inflow diameter D2. In one specific example, the outflow diameter D1 is about 30 mm and the inflow diameter D2 is about 27 mm.

In another example, the outflow diameter D1 is about 31.5 mm and the inflow diameter D2 is about 29 mm. In another example, the outflow diameter D1 is about 24.5 mm and the inflow diameter D2 is about 22 mm.

Referring now to FIG. 10, in some embodiments, while in the crimped or radially compressed configuration, the frame 302 can have a tapered shape wherein the diameter D1 of the outflow end 326 is smaller than the diameter D2 of the inflow end 324, giving the radially compressed frame 302 a negative draft angle. The tapered shape created by a negative draft angle can be beneficial for retracting the frame 302 into the sheath of the delivery apparatus, if the prosthetic valve 300 needs to be retrieved or removed during an implantation process.

The ratio between the inflow and outflow diameters of the prosthetic valve 300 can change during expansion and compression, thus changing the draft angle of frame 302. For example, the prosthetic valve 300 can have a first draft angle when in the radially compressed configuration (FIG. 10), a second draft angle when in the partially expanded/partially compressed configuration (FIGS. 8-9), and a third draft angle when in the fully expanded configuration (FIG. 7). FIG. 10 shows the radially compressed configuration of the frame 302 after it has been radially compressed without any plastic deformation of the struts 308. The frame 302 can be crimped to shape shown in FIG. 10 without any elastic deformation of the struts or with elastic deformation of the struts 308, depending on how the frame is assembled.

FIG. 7 shows the frame 302 in a fully expanded configuration having a positive draft angle (e.g., the diameter at the outflow end 326 of the prosthetic valve 300 is greater than the diameter at the inflow end 324). FIGS. 8 and 9 show partially radially compressed configurations of the frame 302, having a negative draft angle (e.g., the diameter D2 at the inflow end 324 of the frame 302 is greater than the diameter D1 at the outflow end 326). FIG. 10 shows the frame in a fully radially compressed configuration wherein the frame 302 has a negative draft angle. This tapered shape can aid in re-crossing the native aortic annulus, when necessary, as described below with reference to FIG. 12.

Referring now to FIG. 11, in some embodiments, during crimping of the prosthetic valve, a crimping mechanism can be used to further crimp the prosthetic valve beyond the configuration of FIG. 10 by applying force to the frame sufficient to deform the struts within the elastic and plastic deformation range of the struts, thus causing the diameter D2 at the inflow end 324 to be equal or substantially equal to the diameter D1 at the outflow end. This can create a "barrel shaped" valve having a shape wherein a diameter D3 at the middle portion of the prosthetic valve 300 is slightly greater than the diameters D1, D2 at the outflow and inflow portions, respectively. In other embodiments, crimping can radially compress the prosthetic valve until it has a null draft angle, meaning the prosthetic valve in the fully compressed configuration is cylindrical.

The frame 302 can be retained in a barrel or cylindrical configuration by a delivery apparatus while being advanced through the patient's vasculature to an implantation site. For example, after crimping the prosthetic valve to achieve a barrel or cylindrical shape, it can be placed in the sheath of a delivery apparatus, which can retain the shape of the frame against the expansion forces of the frame. Once deployed from the sheath at or near the implantation site, the frame 302 can recover from the deformed shape of FIG. 11 and revert back to its relaxed state, which can be one of the compressed state of FIG. 10, the partially expanded states of FIGS. 9-10, or the fully expanded state of FIG. 7.

Figure 15:
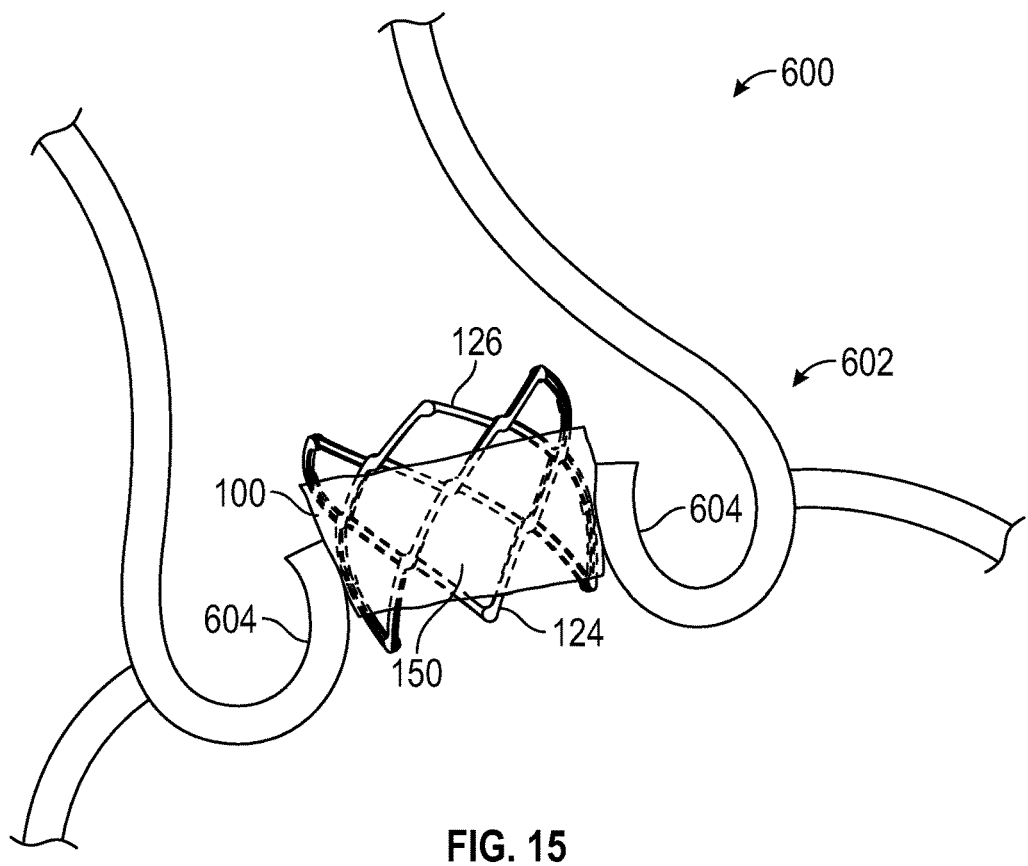
FIG. 15 is a side view of an embodiment of a prosthetic valve implanted within a native aortic valve of a heart, which is partially shown.

The tapered frames of prosthetic valves 100, 200, 300, 700, and 800 when implanted, can help reduce the pressure gradient through prosthetic valve by increasing the effective outflow orifice of the prosthetic valve, and mitigating the acceleration of flow through the prosthetic valve and the formation of eddies and turbulence at the outflow of the prosthetic valve. For example, FIG. 15 shows exemplary prosthetic valve 100 implanted within the native annulus of a patient. In addition, the increased diameter at the outflow end of the prosthetic valve provides additional space for the expansion actuators (e.g., actuators 20 of prosthetic valve 10), if needed, helping mitigate any perturbation of flow caused by the location of the actuators within the frame.

The tapered shape of the frame can also improve paravalvular sealing between an outer skirt 150 and the surrounding tissue (e.g., the native aortic leaflets). As shown in FIG. 15, the tapered shape of the frame can effectively wedge the prosthetic valve between the native leaflets (the native aortic valve leaflets 604 in the illustrated configuration), similar to a male cone that is received by a female cone of a cone clutch assembly.

Figure 12:
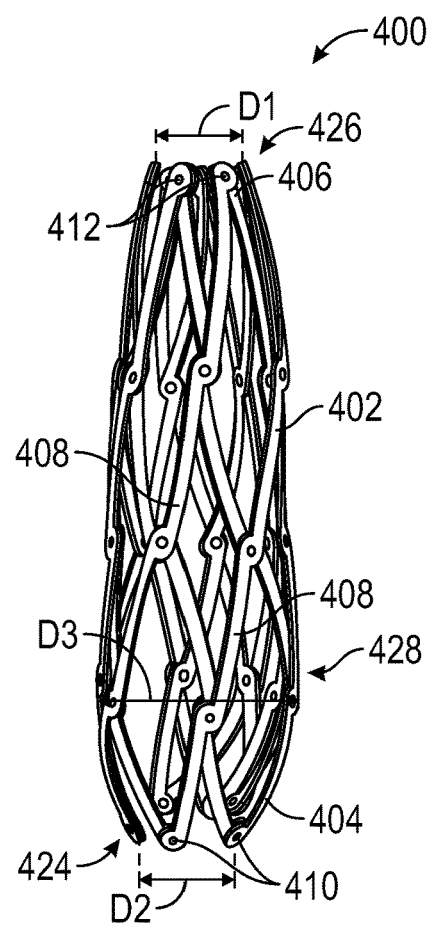
FIG. 12 is a side elevational view of another embodiment of a frame for a prosthetic heart valve.

FIG. 12 illustrates a prosthetic valve 400, according to another embodiment, comprising a frame 402. Similar to prosthetic valve 10, the prosthetic valve 400 can include a valvular structure (e.g., valvular structure 18), inner and/or outer skirts, and actuators (e.g., actuators 20) as previously described, although these components are omitted for purposes of illustration.

FIG. 12 shows the frame 402 in a radially compressed state. The frame 402 comprises an inflow end portion 404 and an outflow end portion 406. The inflow end portion 404 and the outflow end portion 406 curve radially inwardly toward the longitudinal axis of the prosthetic valve. The curved inflow end portion 404 facilitates re-crossing of the native aortic annulus during implantation without requiring the re-sheathing of prosthetic valve 400 within a delivery apparatus, as described in more detail below. In some embodiments, when the prosthetic valve 400 is in the expanded configuration, the inflow and/or outflow end portions of the frame can maintain a shape that curves radially inwardly. The inwardly curved shape of the inflow and/or outflow end portions 404, 406 can help prevent or mitigate contact between the inflow and outflow apices 410, 412 of the frame 402 from contacting the native anatomy, thereby preventing or mitigating damage to the native anatomy.

In other embodiments, one or more of the inflow and/or outflow end portions can be configured to flare radially outwardly away from the longitudinal axis of the prosthetic valve. The inflow and/or outflow end portions can flare radially outwardly when the frame is in the radially compressed state, the radially expanded state, or both. In some particular embodiments, as described in more detail below, the inflow and/or outflow end portions of the frame can curve radially inwardly when the frame is in the compressed state and can flare radially outwardly when the frame is in the expanded state.

Figure 14:
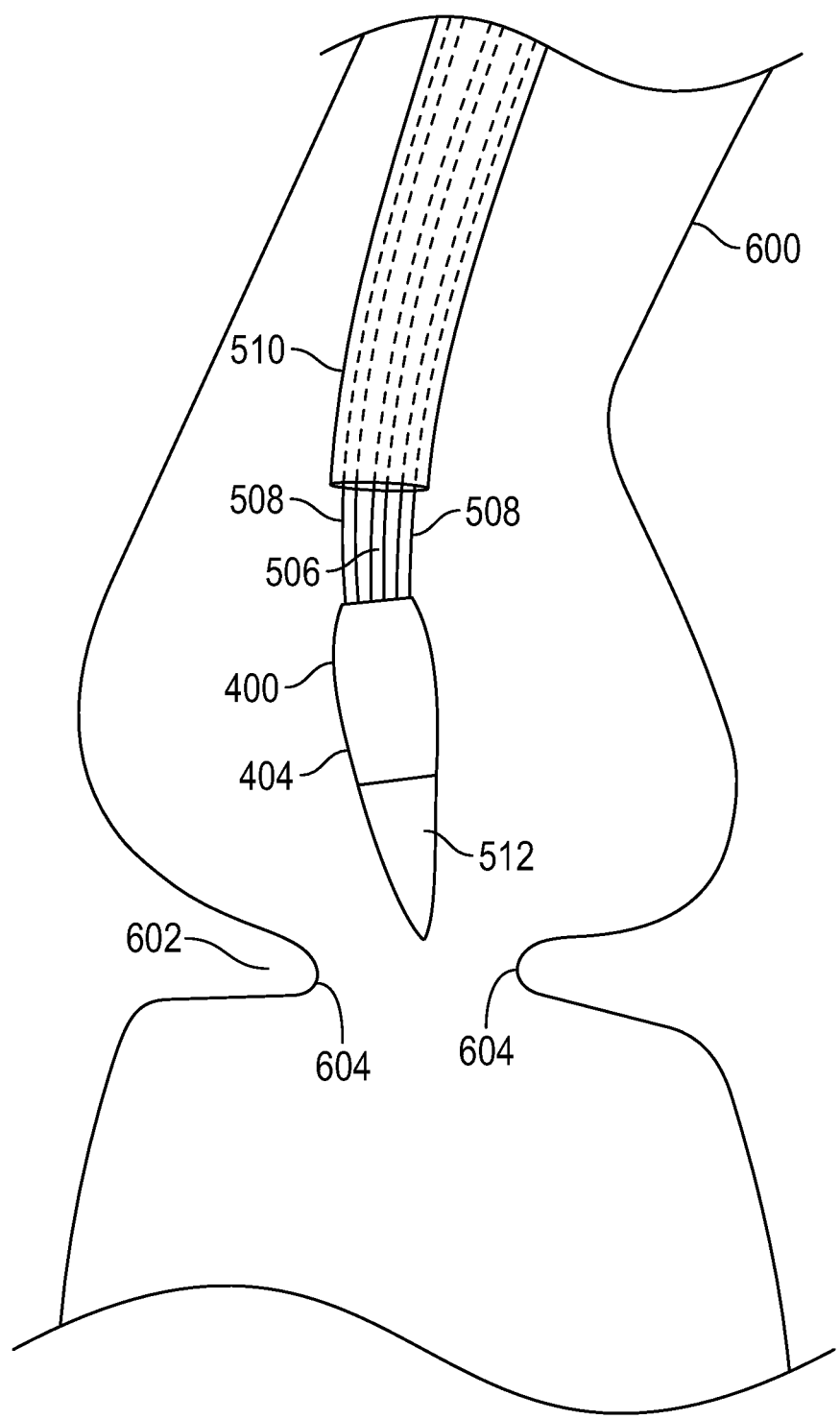
FIG. 14 is a side view of an embodiment of a prosthetic valve being implanted within a native aortic valve of a heart, which is partially shown.

As shown in FIG. 12, the curved inflow portion 404 can define an inflow end 424 of the frame 402, and the outflow end portion 406 can define an outflow end 426. In the crimped configuration, the curved inflow and/or outflow portions 404, 406 can give the frame a non-cylindrical, tapered shape wherein the outflow end 426 has a first diameter D1, the inflow end 424 has a second diameter D2, and an intermediate portion 428 of the frame adjacent the inflow end 424 has a third diameter D3. The curvature of the inflow end portion 404 creates a tapered shape wherein the third diameter D3 is greater than the second diameter D2 at the inflow end 424. This allows a smooth taper to be formed between the inflow end portion 404 of the frame 402 and the nose cone 512, as shown in FIG. 14.

The frame 402 in the illustrated embodiment also has a more gradual taper from the intermediate portion 428 to the outflow end 426 such that the diameter D3 is greater than the diameter D1 at the outflow end. The diameter D1 in the illustrated embodiment is less than the diameter D2, but in alternatively embodiments the diameter D1 can be the same as D2 or greater than D2.

The curved inflow and/or outflow end portions 404, 406 of the frame 402 and the taper from the intermediate portion 428 to the outflow end 426 can be formed by shape-setting the struts of the frame, such as by heating the frame 402 and plastically deforming the struts 408 to form the shape shown in FIG. 12. In some embodiments, the frame can be shape-set to have curved and/or flared end portions while the frame is in an assembled state. In other embodiments, each strut can be shape-set prior to have a curved and/or flared shape prior to assembling the frame. In still other embodiments, the curved or flared portions of the frame can be formed in various other ways, as described in more detail below.

As mentioned previously, in some embodiments, a strut can be radially curved or flared along the length of the strut. In other embodiments, a strut can comprise one or more radially curved or flared segments. For example, one or more segments of a strut can be shape-set or bent such that they curve radially inward toward a longitudinal axis of the prosthetic valve or flare radially outward away from the longitudinal axis of the prosthetic valve. In some embodiments, only the distal-most and/or proximal-most segments of a strut can be curved and/or flared. In other embodiments, a strut can be curved or flared along the length of the strut and the distal-most and/or proximal-most segments of the strut can be further curved or flared such that they bend radially inwardly or outwardly at a steeper angle.

In still other embodiments, the curved or flared end portions can be formed using struts having segments of differing lengths. For example, in some embodiments, the distal-most and/or proximal-most segments of selected struts (which together form a crown) can have shorter and/or longer lengths than the distal-most or proximal-most segments of the struts which form adjacent crowns. As the frame is crimped, the differing lengths of the distal- and/or proximal-most segments cause the inflow and/or outflow end portions of the frame to bend radially inwardly, forming tapered or curved end portions. The curved inflow portion of the prosthetic valve when in the compressed configuration can facilitate re-crossing of the native annulus, especially in instances where the native leaflets have become calcified. As the frame is expanded, the struts pivot relative to one another such that the inflow and/or outflow ends of the frame bend radially outwardly to form a flared end portion. The flared inflow end portion can help prevent or mitigate the risk of paravalvular leakage (PVL) that may occur if there is a gap between the inflow end portion of the prosthetic valve and the native annulus.

FIGS. 34-37 illustrate various exemplary embodiments of a prosthetic heart valve 1400 having a frame 1402 comprising a plurality of struts 1404 pivotably connected to each other at a plurality of junctions 1406. The junctions can include junctions at the outflow end portion 1408 of the frame 1402 (referred to as proximal crowns 1410) and junctions at the inflow end portion 1412 of the frame (referred to as distal crowns 1414). The prosthetic valve 1402 can include a valvular structure (e.g., valvular structure 18) and inner and/or outer skirts, as previously described, though these components are omitted for purposes of illustration. While only one side of the frame 1402 is depicted in FIGS. 34-37, it should be appreciated that frame 1402 forms an annular structure having an opposite side that is identical to the portion shown.

Figure 34:
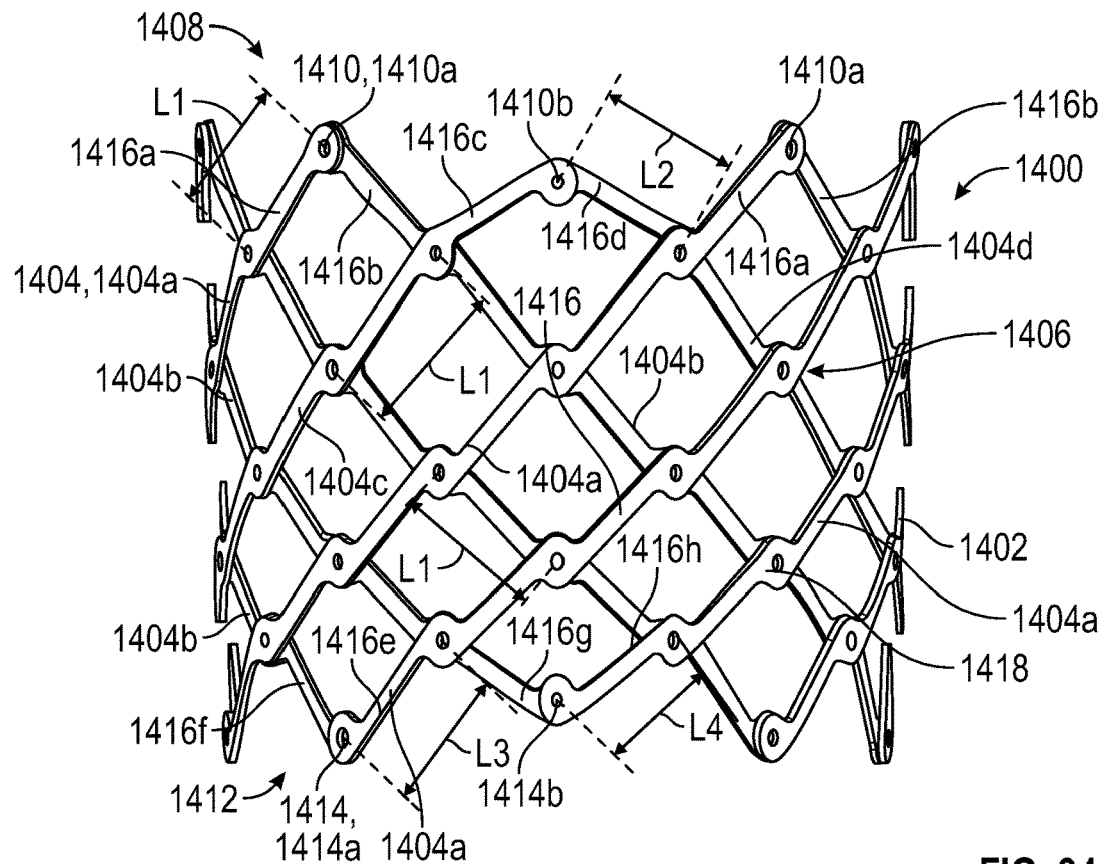
FIG. 34 is a side elevational view of an embodiment of a frame for a prosthetic heart valve.

Referring to FIG. 34, each strut can comprise a plurality of segments 1416 arranged end-to-end relative to each other with adjacent ends interconnected to each other by connecting segments 1418. Each of the connecting segments 1418 can have a respective aperture at its geometric center for receiving a fastener.

As shown in FIG. 34, the outflow end portion 1408 of the frame 1402 can include one or more first proximal crowns 1410a, each comprising a first strut 1404a and a second strut 1404b. In the illustrated embodiment, first struts 1404a are spaced radially outward of second struts 1404b, however, in other embodiments, second struts 1404b can be spaced radially outward of first struts 1404a. The struts 1404a, 1404b can each comprise a proximal-most segment 1416a, 1416b having a length $L_1$. The frame 1402 can further include one or more second proximal crowns 1416b, each comprising a third strut 1404c and a fourth strut 1404d. The struts 1404c, 1404d can each comprise a proximal-most segment 1416c, 1416d having a length $L_2$ shorter than length $L_1$. Likewise, the inflow end portion 1412 of the frame 1402 can include one or more first distal crowns 1414a, each comprising a first strut 1404a and a second strut 1404b. The first and second struts 1404a, 1404b each comprise a distal-most segment 1416e, 1416f having a length $L_3$. In the illustrated embodiment, $L_3$ is equal to $L_1$, however, in other embodiments, $L_3$ can be greater than $L_1$ or vice versa. The frame can further include one or more second distal crowns 1414b, each comprising a third strut 1404c and a fourth strut 1404d. The struts 1404c, 1404d can each comprise a distal-most segment 1416g, 1416h having a length $L_4$ shorter than length $L_3$. In the illustrated embodiment, $L_4$ is equal to $L_2$, however, in other embodiments $L_4$ can be greater than $L_2$ or vice versa. The strut segments between the segments at the opposite ends of the frame can all have a length $L_1$; that is, the strut segments not forming any of the proximal and distal crowns can all have a length $L_1$.

For ease of reference, crowns where the proximal-most or distal-most segment has a length $L_1$ or $L_3$ (e.g., the first proximal crowns 1410a and the first distal crowns 1414a) can be referred to as "standard crowns" 1410a, 1414a and crowns where the proximal-most or distal-most segment has a length $L_2$ or $L_4$ (e.g., the second proximal crowns 1410b and the second distal crowns 1414b) can be referred to as "shorter crowns" 1410b, 1414b.

In the embodiments shown in FIG. 34, the shorter crowns 1410b, 1414b or longer crowns 1410c, 1414c are disposed between the standard crowns 1410a, 1414a such that the shorter and standard crowns or the longer and standard crowns have an alternating configuration. However, in other embodiments, the shorter crowns and standard crowns can be disposed in any of various configurations. For example, there can be two shorter crowns 1410b, 1414b disposed between each pair of standard crowns 1410a, 1414a, or vice versa. In still other embodiments, all the inflow and/or outflow crowns of a prosthetic valve can be shorter crowns. In some particular embodiments, the frame 1402 can be configured such that, when implanted within a native annulus, the shorter crowns 1410b, 1414b align with the commissures of the native leaflets, and the standard crowns align with the native sinuses.

Figure 35:
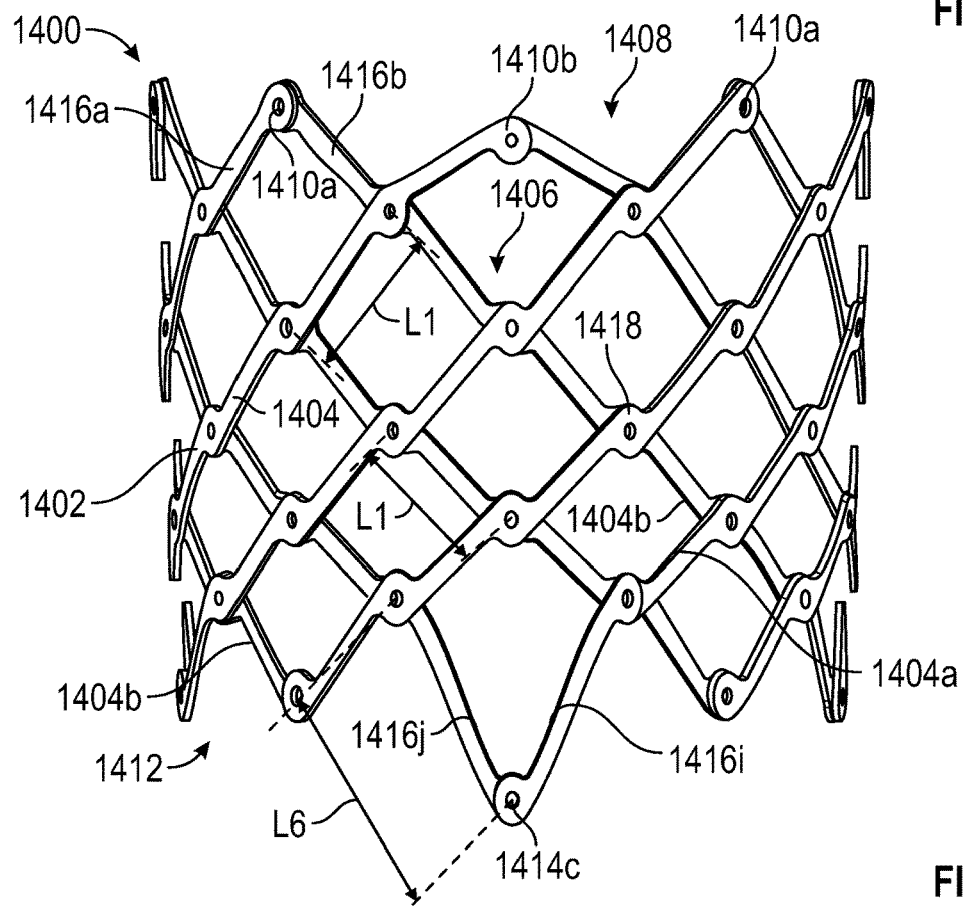
FIG. 35 is a side elevational view of another embodiment of a frame for a prosthetic heart valve.

In some embodiments, in lieu of or in addition to the standard crowns 1410a, 1414a and/or the shorter crowns 1410b, 1414b, the frame 1402 can comprise one or more crowns having proximal-most or distal-most segments having a length $L_5$ (for proximal-most segments, see FIG. 36) or $L_6$ (for distal-most segments, see FIG. 35), where $L_5$ and $L_6$ are greater than $L_1$ and $L_3$. Crowns where the proximal-most or distal-most segment has a length $L_5$ or $L_6$ can be referred to as "longer crowns" or "elongated crowns" 1410c, 1414c. FIG. 35 illustrates an embodiment of frame 1402 wherein the inflow end portion 1412 comprises one or more elongated crowns 1414c. The longer crown 1414c can comprise a first strut 1404a and a second strut 1404b each comprising a distal-most segment 1416i, 1416j, respectively, having a length $L_6$ greater than the length $L_3$ of the distal-most segments of the adjacent standard crowns 1414a. In the embodiment shown in FIG. 35, the longer crown 1414c is disposed between two standard crowns 1414a such that the longer and standard crowns have an alternating configuration. However, in other embodiments, the longer crowns and standard crowns can be disposed in any of various configurations. In some embodiments, the inflow and/or outflow end portions of the frame 1402 can comprise only longer crowns.

In some embodiments, the inflow and/or outflow end portions 1408, 1412 of the valve can comprise any combination of shorter crowns, longer crowns, and standard crowns in any pattern.

Figure 36:
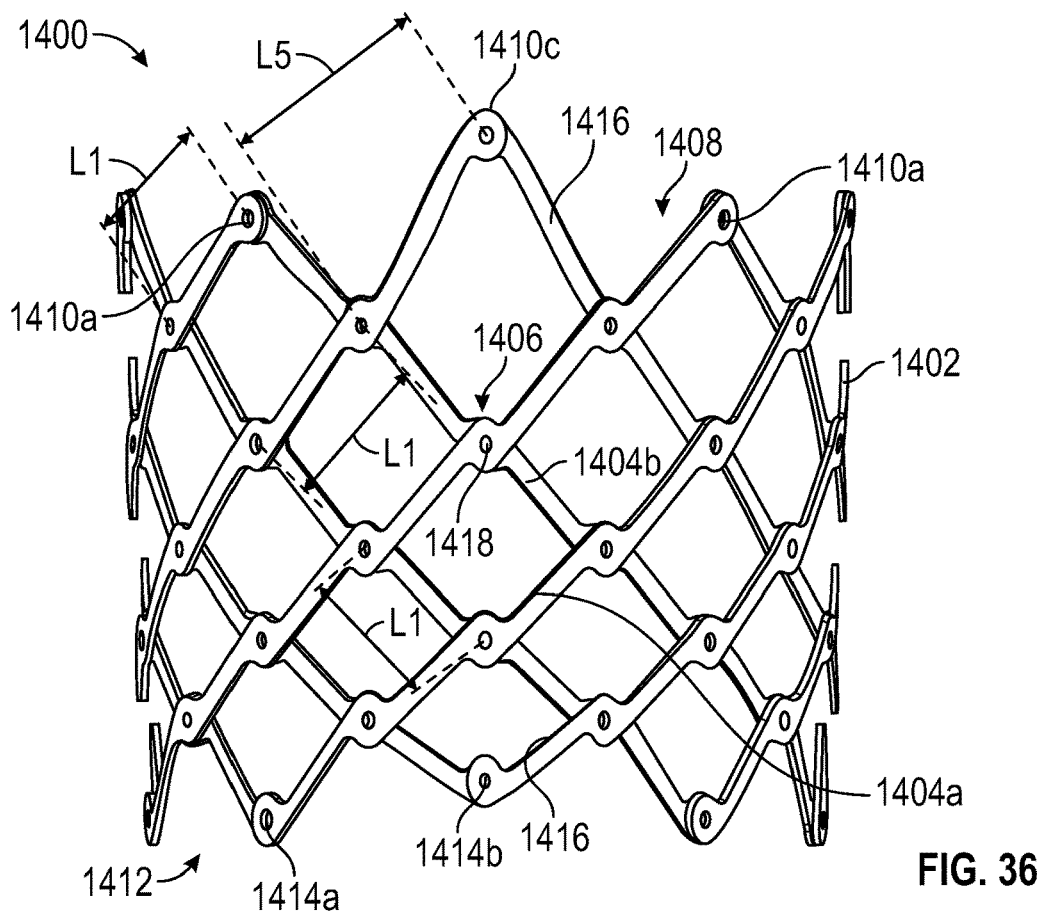
FIG. 36 is a side elevational view of another embodiment of a frame for a prosthetic heart valve.
Figure 37:
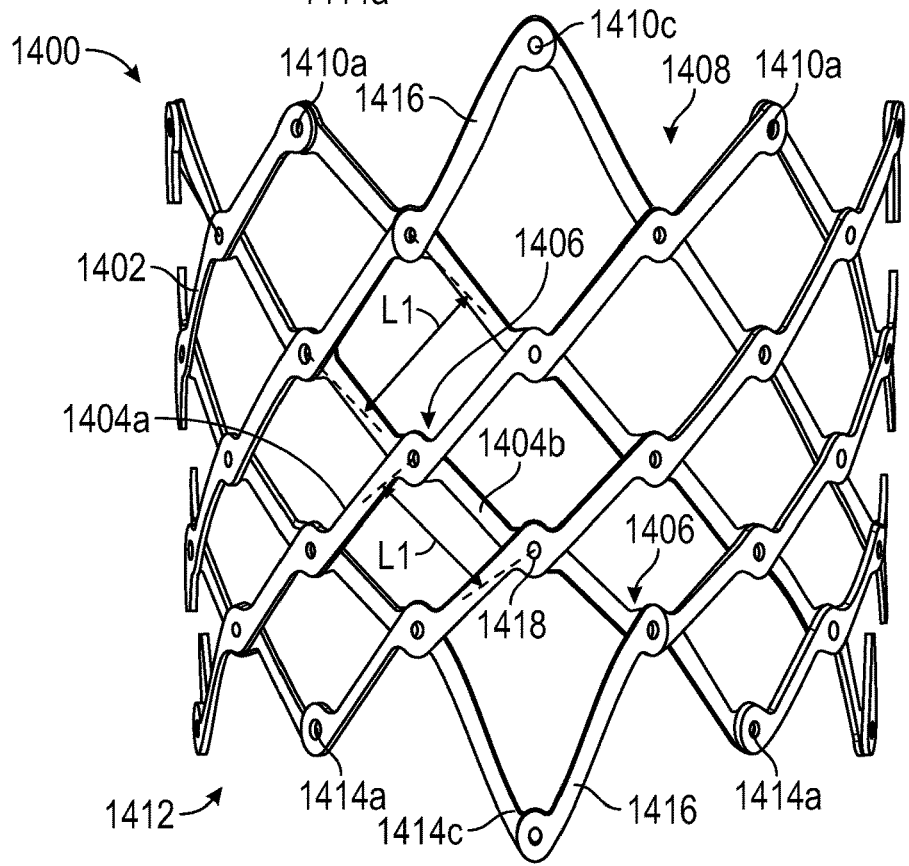
FIG. 37 is a side elevational view of another embodiment of a frame for a prosthetic heart valve.

FIGS. 34-37 illustrate frames having various combinations of proximal and distal crowns 1410, 1414. FIG. 34 illustrates an embodiment wherein both the outflow end portion 1408 and the inflow end portion 1412 comprise one or more shorter crowns 1410b, 1414b and one or more standard crowns 1410a, 1414a. FIG. 35 illustrates an embodiment wherein the outflow end portion 1408 comprises one or more shorter crowns 1410b and one or more standard crowns 1410a and the inflow end portion 1412 comprises one or more longer crowns 1414c and one or more standard crowns 1414a. FIG. 36 illustrates an embodiment wherein the outflow end portion 1408 comprises one or more longer crowns 1410c and one or more standard crowns 1410a, and wherein the inflow end portion comprises one or more shorter crowns 1414b and one or more standard crowns 1414a. FIG. 37 illustrates an embodiment wherein the outflow end portion 1408 and the inflow end portion 1412 each comprise one or more longer crowns 1410c, 1414c and one or more standard crowns 1410a, 1414a.

Due to the elasticity of the struts 1404 and the connections between overlapping struts, the degree of curvature of a strut (radially inwardly and outwardly relative to longitudinal axis A) can change during radial compression and expansion of the frame 1402. For example, as the frame 1402 is crimped, the struts 1404 pivot toward one another, decreasing the distance between adjacent junctions 1406 in a circumferential row of junctions 1406. This causes the proximal and/or distal crowns 1410, 1414 to bend radially inwardly as the frame is crimped, resulting in a tapered or curved outflow end portion 1408 and/or inflow end portion 1412. The shorter crowns can bend radially inward at a faster rate than the standard and/or longer crowns.

As the frame 1402 expands, the struts 1404 pivot away from each other, increasing the distance between the junctions 1406 in a circumferential row of junctions. This causes the proximal and/or distal crowns 1410, 1414 to bend radially outwardly as the frame expands, resulting in a flared outflow end portion 1408 and/or inflow end portion 1412. As mentioned previously, a flared inflow end portion can help prevent or mitigate PVL.

In the embodiments of FIGS. 34-37, the struts of the frame are helically curved but not curved with respect to an axis D (FIGS. 4B and 6B) (that is, the struts are straight in a flat projection of the frame). However, it should be understood that any of the concepts described in connection with FIGS. 34-37 can be applied to any of the frames disclosed herein, including those with struts that are curved with respect to an axis D.

Referring again to FIG. 12, in the illustrated embodiment, each strut 408 is straight in the plane P (see plane P in FIG. 4A); that is, the struts do not have a curvature with respect to an axis B, but may be curved helically with respect to axis A. In alternative embodiments, however, any of the above-described methods and/or strut configurations can be used to create curved portions at the inflow or outflow end portions of any of the previously described prosthetic valves 100, 200, 300, 700, and 800.

Though not shown, any of the prosthetic valve described herein (e.g., prosthetic valves 100, 200, 300, 400, 700, 800) can comprise actuators, such as actuators 20 of prosthetic valve 10, for producing radial expansion and compression of the prosthetic valve.

Figure 13:
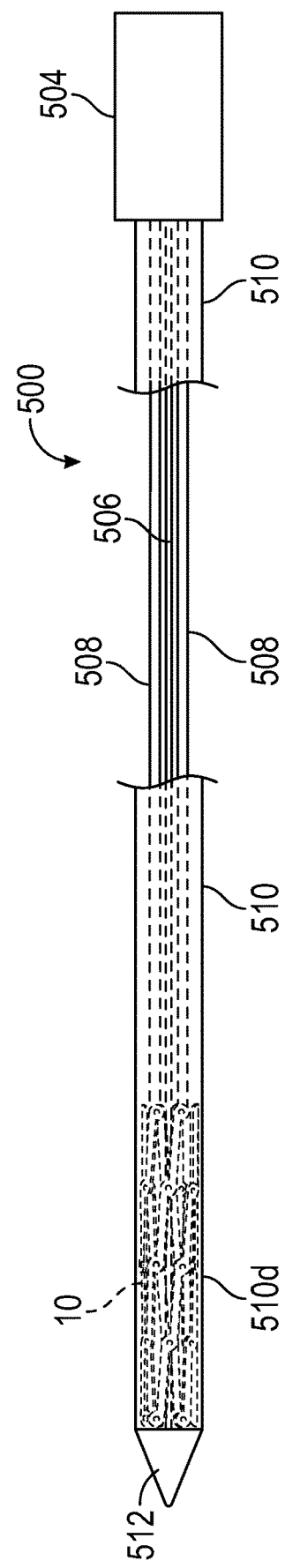
FIG. 13 is side view of an embodiment of a prosthetic valve delivery apparatus shown being used to implant a prosthetic heart valve.

FIG. 13 shows one example of a delivery assembly 500 that can be used to deliver and implant any of the prosthetic valves disclosed herein within a patient's body. The delivery assembly 500 can include two main components: a delivery apparatus 502 and a prosthetic heart valve (prosthetic heart valve 10 is shown in FIG. 13 as a representative example of a prosthetic valve). The prosthetic valve 10 can be mounted in a radially compressed configuration around a distal end portion of the delivery apparatus 502 for insertion into a patient's body. In some embodiments, the prosthetic valve 10 can be oriented so that the outflow end is positioned proximally relative to the inflow end. In this orientation, the prosthetic valve can be advanced through the patient's vasculature in a retrograde approach (e.g., through a femoral artery and the aorta) to the heart for implantation at the native aortic valve. In other embodiments, the prosthetic valve 10 can be oriented so that the inflow end is positioned proximally relative to the outflow end, depending on the particular delivery approach used and the implantation location for the prosthetic valve.

The delivery apparatus 502 in the illustrated embodiment includes a handle 504, a first shaft 506 extending distally from the handle 504, a plurality of actuator members 508 extending distally from the handle 504, and a second shaft 510 extending co-axially over the first shaft 506 and the actuator members 508, and a nose cone 512. The first shaft 506 is the inner-most shaft in the illustrated embodiment and can be referred to as the inner shaft of the delivery apparatus 502. Likewise, the second shaft 510 is the outer-most shaft in the illustrated embodiment and can be referred to as the outer shaft or outer sheath of the delivery apparatus 502. The shafts 506, 510 and the actuator members 508 can be axially and/or rotationally moveable relative to each other.

The nose cone 512 can be connected to a distal end of the inner shaft 506. A guide wire (not shown) can extend through a central lumen of the inner shaft 506 and an inner lumen of nose cone 512, so that the delivery apparatus 502 can be advanced over the guide wire inside the patient's vasculature.

The proximal ends of the shafts 506, 510 and the actuator members 508 can be coupled to the handle 504. During delivery of a prosthetic valve, the handle 504 can be maneuvered by a surgeon to advance or retract the delivery apparatus through the patient's vasculature. In some embodiments, the handle 504 can include a plurality of knobs or other actuating mechanisms for controlling different components of the delivery assembly 500 in order to expand and/or deploy the prosthetic valve. For example, the handle 504 can include one or more knobs or other actuating mechanisms, each configured to produce relative axial and/or rotational movement of a selected shaft 506 or 510 or a selected actuator member 508 relative to the others.

As shown in FIG. 13, a distal end portion 510d of the outer sheath 510 can extend over the prosthetic valve 10 and contact the nose cone 512 in the delivery configuration of the delivery apparatus 502. Thus, the distal end portion 510d of the outer sheath 510 can serve as a delivery capsule that contains or houses prosthetic valve 10 in the radially compressed configuration for delivery through the patient's vasculature. The outer sheath 510 and the inner shaft 506 can be configured to be axially movable relative to one another and the actuator members 508 such that proximal movement of the outer sheath 510 relative to the inner shaft 506 and the actuator members 508 (or distal movement of the inner shaft 506 and the actuator members 508 relative to the outer sheath 510) can expose the prosthetic valve 10 from the outer sheath 510. In alternative embodiments, the prosthetic valve 10 need not be housed within the outer sheath 510 during delivery. As such, in some embodiments, the delivery apparatus 502 does not include the outer sheath 510.

Figure 20:
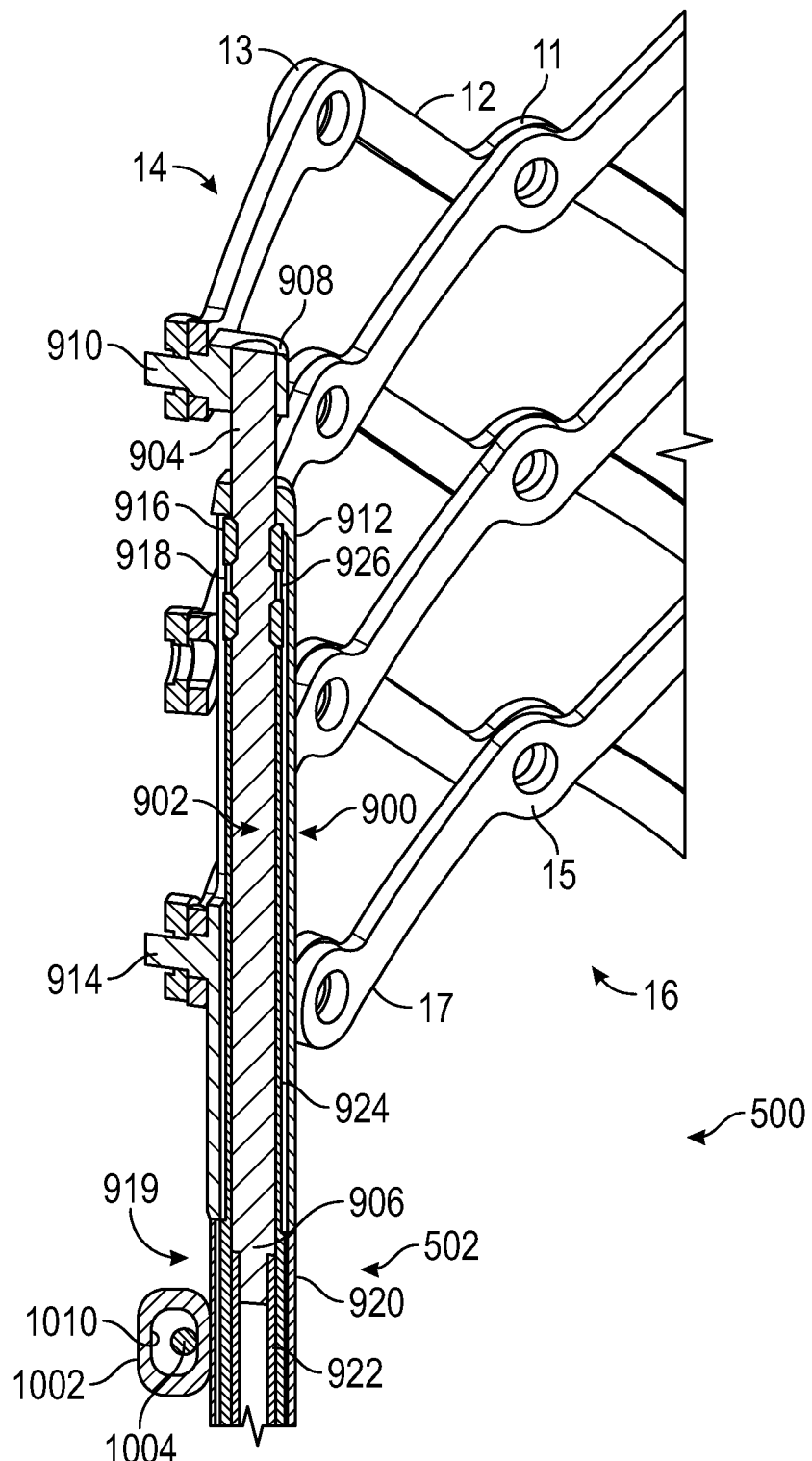
FIG. 20 is a cross-sectional view of an exemplary expansion and locking member including an exemplary crimping mechanism, along with a portion of the frame.
Figure 21:
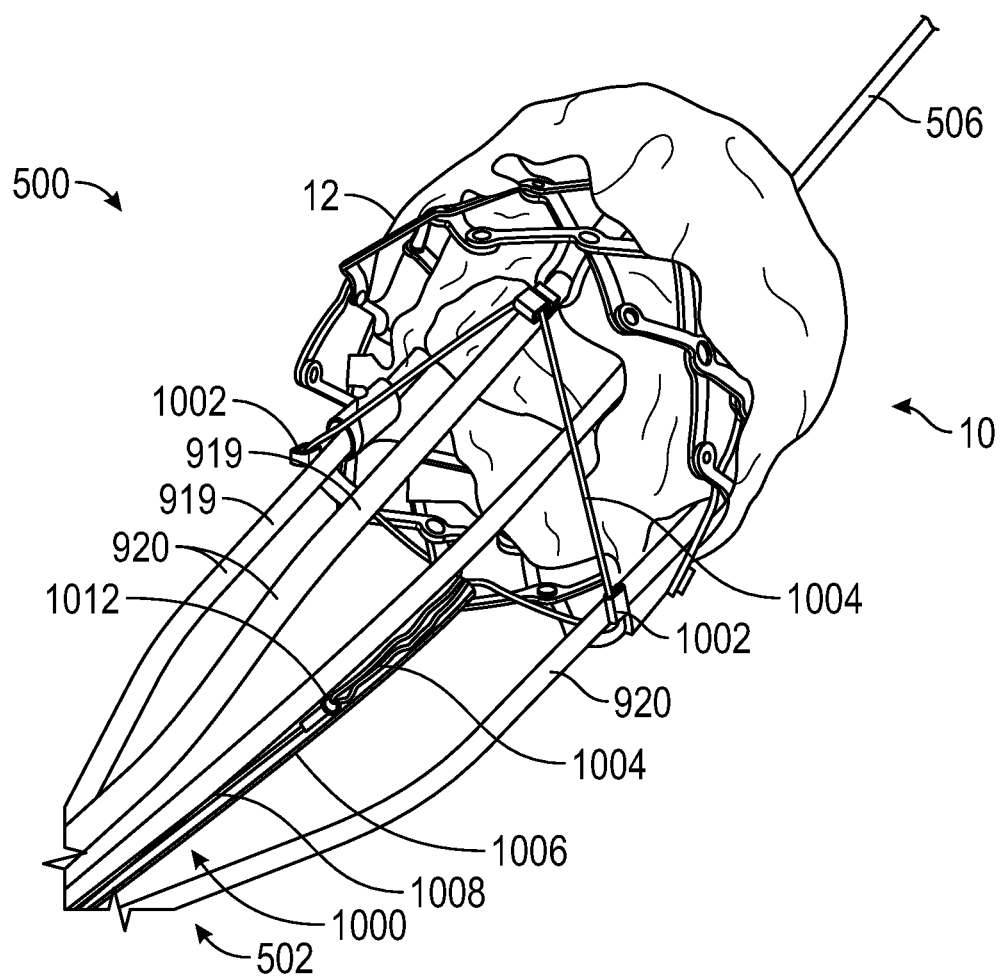
FIG. 21 is a perspective view of the distal end portion of a delivery apparatus including the crimping mechanism of FIG. 20 and a prosthetic valve coupled to the delivery apparatus, according to one embodiment.

Each actuator member 508 can have a proximal end portion connected to the handle 504 and a distal end portion releasably connected to a respective actuator 20 of the prosthetic heart valve 10 (see e.g., FIGS. 20-21). One actuator member 508 can be provided for each actuator 20 on the prosthetic valve. In the illustrated embodiment, the delivery apparatus 502 includes three such actuator members 508 (only two are shown in FIGS. 13 and 14 for purposes of illustration, but see e.g., FIG. 21), although in other embodiments a greater of fewer number of actuator members 508 can be used depending on the number of the actuators provided on the prosthetic valve.

In some embodiments, the actuator members 508 of the delivery apparatus can be torque shafts having distal end portions configured to mate with corresponding attachment members 38 of rods 32. In such embodiments, the torque shafts can be rotated (e.g., in a clockwise direction) thereby causing the rods or screws 32 to rotate and radially compress the prosthetic valve 10. At or adjacent the implantation site, a control knob or other actuator on the handle 504 can be actuated to rotate the torque shafts (e.g., in a counter-clockwise direction), thereby causing the rods or screws 32 to rotate and radially expand the frame 12 of the prosthetic valve 10. Further details of the actuator members, their use, and the manner in which they connect to the respective actuators of the prosthetic valve can be found in U.S. application Ser. Nos. 16/105,353; 15/831,197 (published as U.S. Publication No. 2018/0153689) and Ser. No. 15/959,623, which are incorporated herein by reference.

The delivery apparatus 502 can be used to deliver and implant a prosthetic heart valve having a tapered frame, for example, prosthetic heart valve 400, in the following exemplary manner. The prosthetic valve can be connected to the delivery apparatus 502 as described above with respect to prosthetic valve 10. The distal end portion of delivery apparatus 502 (along with the prosthetic valve 400) can be advanced through the vasculature of a patient to a selected implantation site. The prosthetic valve 400 can then be deployed at the implantation site (e.g., the native aortic annulus).

In a particular example, the prosthetic valve 400 can be delivered in a retrograde approach by advancing the delivery apparatus through a femoral artery and the aorta 600 (FIG. 14) to arrive at the native aortic valve 602 having leaflets 604 (FIG. 14). The tapered nose cone 512 facilitates crossing of the native annulus, allowing the sheathed prosthetic valve 400 to be positioned within the native valve. The prosthetic valve 400 can be deployed from the outer sheath 510 by, for example, retracting the sheath 510 proximally with respect to the prosthetic valve 400.

Once deployed from the sheath, the prosthetic valve 400 can be expanded using the actuator members 508 of the delivery device to apply forces to the corresponding actuators (e.g., actuators 20) of the prosthetic valve 400, decreasing the distance between the attachment locations of a respective sleeve and nut, which causes the frame 402 to foreshorten axially and expand radially until it reaches a diameter sufficient to anchor the prosthetic valve in place against the surrounding tissue with minimal or no paravalvular leakage.

In some cases, the physician may need to re-cross the native aortic valve, for example, if the prosthetic valve is accidentally pulled back into the aorta prior to final deployment, or if the physician intentionally decides to re-position the prosthetic valve by first pulling the prosthetic valve back into the aorta. In such cases, the prosthetic valve 400 can be radially re-compressed using the actuator members 508 of the delivery apparatus 502. Once re-compressed, the prosthetic valve 400 can be advanced distally such that it re-crosses the native annulus, thus allowing the prosthetic valve 400 to be re-positioned at the implantation site.

The curved inflow end portion 404 of prosthetic valve 400 facilitates re-crossing of the native annulus without requiring re-sheathing of prosthetic valve 400 within sheath 510. As shown in FIG. 14, the tapered inflow portion 404 creates a smooth transition between the nose cone 512 and the frame 402, helping mitigate the risk of the frame catching on or damaging the native leaflets or aortic wall. The diameter of the proximal end of the nose cone 512 can be the same as or slightly greater than the diameter D2 of the inflow end of the frame. Once the prosthetic valve 400 is situated at the implantation site, the prosthetic valve 400 can be re-expanded.

When the frame is retained in the radially compressed state (such as within the sheath of a delivery apparatus), the elastically deformed struts place the frame in a state of tension. Thus, when released from the radially compressed state (e.g., when deployed from the sheath of a delivery apparatus), the struts provide a spring force that causes the frame to at least partially expand. In some embodiments, during implantation, calcification of the native leaflets 604 (FIG. 15) may initially cause the prosthetic valve to be held in a substantially cylindrical shape. Over time, the spring force exerted by the elastically deformed struts expands the prosthetic valve into a non-cylindrical shape such as a frustoconical or V-shape. The gradual expansion allows for atraumatic movement of the calcified leaflets, thus mitigating risk to the patient.

Figure 18C:
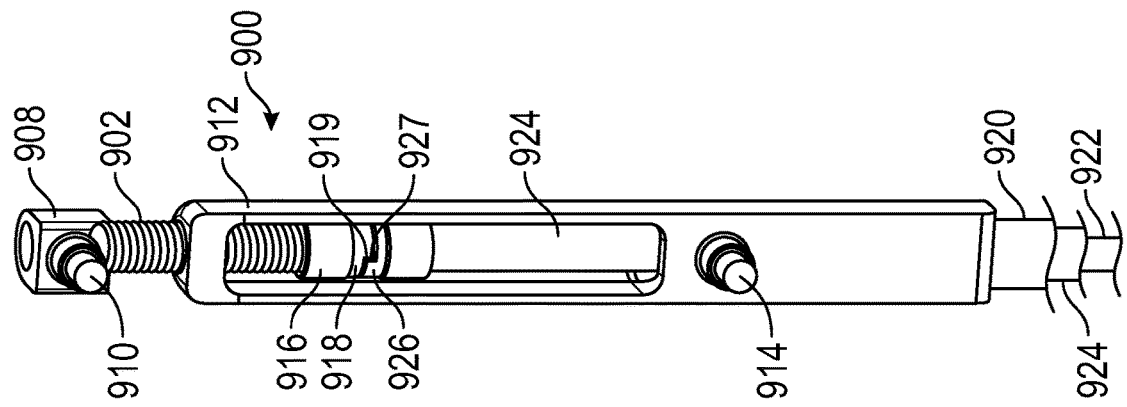
FIG. 18C is another perspective view of the expansion and locking mechanism of FIG. 18B.
Figure 18B:
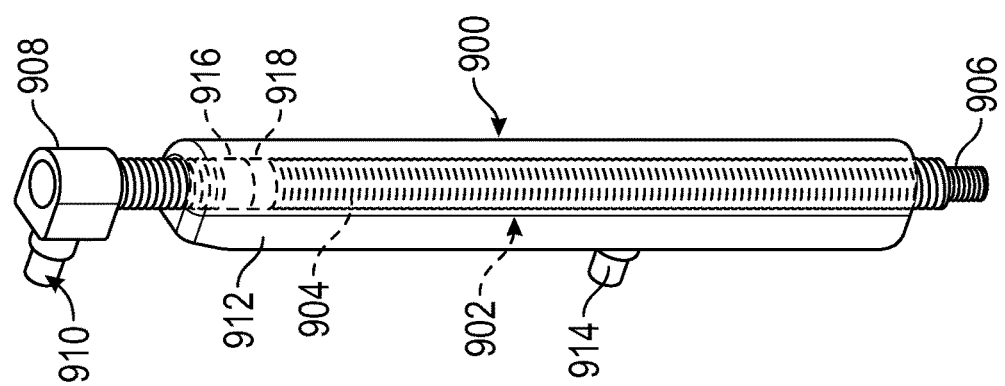
FIG. 18B is a perspective view of an exemplary expansion and locking mechanism.
Figure 18A:
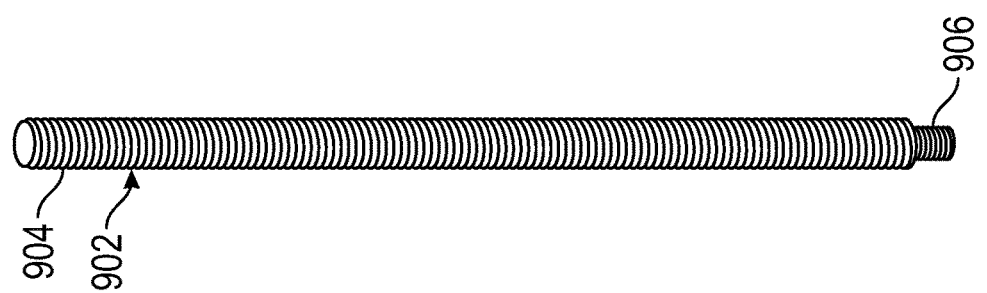
FIG. 18A is a perspective view of a screw of an exemplary expansion and locking mechanism.
Figure 19:
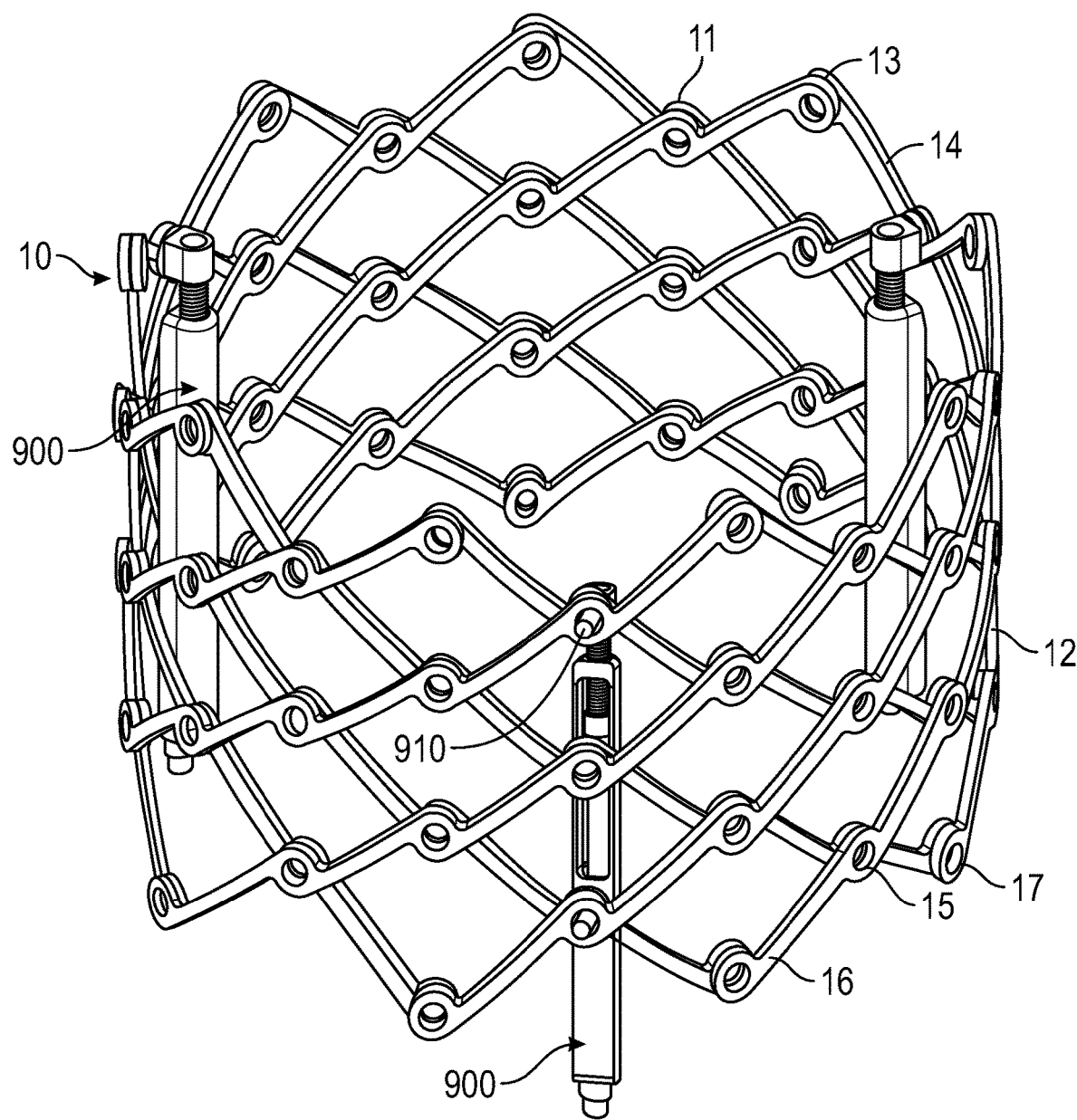
FIG. 19 is a perspective view of a prosthetic valve frame, shown in a radially expanded state, having a plurality of expansion and locking mechanisms according to FIG. 18B.

Referring now to FIGS. 18-19, in some embodiments, a prosthetic valve (e.g., a prosthetic valve 10) can include one or more expansion and locking mechanisms 900 (which can also be referred to as actuators) in lieu of or in addition to the actuators 20 described above. As shown in FIG. 18A, the expansion and locking mechanism 900 in the illustrated embodiment can include an actuator screw 902 (which functions as a linear actuator or a push-pull member in the illustrated embodiment) comprising a relatively long upper, or distal, portion 904 and a relatively shorter lower, or proximal portion 906 at the proximal end of the screw 902. The lower portion can have a smaller diameter than the upper portion. Both the upper and lower portions 904, 906 can have externally threaded surfaces. Referring now to FIGS. 18B and 18C, the actuator screw 902 can have a distal attachment piece 908 attached to its distal end having a radially extending distal valve connector 910. The distal attachment piece 908 can be fixed to the screw 902 (e.g., welded together or manufactured as one piece).

As shown in FIG. 19, the distal valve connector 910 can extend through an opening at or near the distal end of the frame 12 formed at a location on the frame where two or more struts intersect. The distal valve connector 910 can be fixed to the frame (e.g., welded). Due to the shape of the struts, the inflow, or distal end 14 of the frame 12 comprises an alternating series of distal junctions 11 and distal apices 13. In the illustrated example, the distal valve connectors 910 of the expansion and locking mechanisms 900 are connected to the frame 12 through openings in the distal junctions 11. In other examples, one or more distal valve connectors 910 can be connected to the frame 12 through the distal apices 13. In other embodiments, the distal valve connectors 910 can be connected to junctions closer to the proximal end of the frame 12.

Referring again to FIGS. 18B and 18C, the expansion and locking mechanism 900 can further include a sleeve 912. The sleeve 912 can be positioned annularly around the upper portion 906 of the screw 902 and can contain axial openings at its proximal and distal ends through which the screw 902 can extend. The axial openings and the lumen in the sleeve 912 can have a diameter larger than the diameter of the upper portion 906 of the screw 902 such that the screw can move freely within the sleeve (the screw 902 can be moved proximally and distally relative to the sleeve 912). Because the actuator screw 902 can move freely within the sleeve, it can be used to radially expand and/or contract the frame 12 as disclosed in further detail below.

The sleeve 912 can have a proximal valve connector 914 extending radially from its outer surface. The proximal valve connector 914 can be fixed to the sleeve 912 (e.g., welded). The proximal valve connector 914 can be axially spaced from the distal valve connector 910 such that the proximal valve connector can extend through an opening at or near the proximal end of the frame 12. The outflow, or proximal end 16 of the frame 12 comprises an alternating series of proximal junctions 15 and proximal apices 17. In the illustrated example, the proximal valve connectors 914 of the expansion and locking mechanisms 900 are connected to the frame 12 through proximal junctions 15. In other examples, one or more proximal valve connectors 914 can be connected to the frame 12 through proximal apices 17. In other embodiments, the proximal valve connectors 914 can be connected to junctions closer to the distal end of the frame 12.

It should be understood that the distal and proximal connectors 910, 914 need not be connected to opposite ends of the frame 12. The expansion and locking mechanism 900 can be used to expand and compress the frame as long as the distal and proximal connectors are connected to respective junctions on the frame that are axially spaced from each other.

A locking nut 916 can be positioned inside of the sleeve 912 and can have an internally threaded surface that can engage the externally threaded surface of the actuator screw 902. The locking nut 916 can have a notched portion 918 at its proximal end, the purpose of which is described below. The locking nut can be used to lock the frame 12 into a particular, radially expanded state, as discussed below.

In particular embodiments, an assembly 500 can include a prosthetic valve 10 having the expansion and locking mechanisms 900 and a delivery apparatus 502. As shown in FIG. 20, in lieu of or in addition to actuator members 508, the delivery apparatus 502 can include actuator mechanisms 919 configured to engage and actuate the expansion and locking mechanisms 900. The delivery apparatus 502 of FIGS. 20-21 can have any of the components of the delivery apparatus 502 of FIGS. 13-14 described above.

The actuator mechanisms 919 can include a support tube 920, an actuator member 922, and a locking tool 924. The proximal end of the support tube 920 can be connected to the handle 504 of the delivery apparatus 502 or other control device (not shown) that a doctor or operator of the delivery assembly utilizing to operate the expansion and locking mechanism 900 as described herein. Similarly, the proximal ends of the actuator member 922 and the locking tool 924 can be connected to the handle.

The support tube 920 annularly surrounds a proximal portion of the locking tool 924 such that the locking tool extends through a lumen of the support tube. The support tube 920 and the sleeve are sized such that the distal end of the support tube abuts or engages the proximal end of the sleeve 912 such that the support tube is prevented from moving distally beyond the sleeve.

The actuator member 922 extends through a lumen of the locking tool 924. The actuator member 922 can be, for example, a shaft, a rod, a cable, or wire. The distal end portion of the actuator member 922 can be releasably connected to the lower portion 906 of the actuator screw 902. For example, the distal end portion of the actuator member 922 can have an internally threaded surface that can engage the external threads of the lower portion 906 of the actuator screw 902. Alternatively, the actuator member can have external threads that engage an internally threaded portion of the screw. When the actuator member 922 is threaded onto the actuator screw 902, axial movement of the actuator member causes axial movement of the screw.

The distal portion of the locking tool 924 annularly surrounds the actuator screw 902 and extends through a lumen of the sleeve 912 and the proximal portion of the locking tool annularly surrounds the actuator member 922 and extends through a lumen of the support tube 920 to the handle of the delivery device. The locking tool 924 can have an internally threaded surface that can engage the externally threaded surface of the locking screw 902 such that clockwise or counter-clockwise rotation of the locking tool 924 causes the locking tool to advance distally or proximally along the screw, respectively.

The distal end of the locking tool 924 can comprise a notched portion 926. The notched portion 926 of the locking tool 924 can have an engagement surface that is configured to engage a correspondingly shaped engagement surface of the notched portion 918 of the locking nut 916 such that rotation of the locking tool (e.g., clockwise rotation) causes the nut 916 to rotate in the same direction (e.g., clockwise) and advance distally along the locking screw 902. The notched portions 918, 926 in the illustrated embodiment are configured such that rotation of the locking tool 924 in the opposite direction (e.g., counter-clockwise) allows the notched portion 926 of the tool 924 to disengage the notched portion 918 of the locking nut 916; that is, rotation of the locking tool in a direction that causes the locking tool to move proximally does not cause corresponding rotation of the nut.

In alternative embodiments, the distal end portion of the locking tool 924 can have various other configurations adapted to engage the nut 916 and produce rotation of the nut upon rotation of the locking tool for moving the nut distally, such as any of the tool configurations described herein. In some embodiments, the distal end portion of the locking tool 924 can be adapted to produce rotation of the nut 916 in both directions so as move the nut distally and proximally along the locking screw 902.

In operation, prior to implantation, the expansion and locking mechanisms 900 of the prosthetic valve 10 can be coupled to the actuator mechanisms 919 of the delivery apparatus 502 in the following exemplary manner. The actuator member 922 is screwed onto the lower portion 906 of the actuator screw 902 and the locking nut 916 is rotated such that it is positioned at the proximal end of the screw. The frame 12 can then be placed in a radially collapsed state and the delivery assembly 500 can be inserted into a patient. Once the prosthetic valve 10 is at a desired implantation site, the frame 12 can be radially expanded as described herein.

To radially expand the frame 12, the support tube 920 is held firmly against the sleeve 912. The actuator member 922 is then pulled in a proximal direction through the support tube, such as by pulling on the proximal end of the actuator member or actuating a control knob on the handle that produces proximal movement of the actuator member. Because the support tube 920 is being held against the sleeve 912, which is connected to a proximal end 16 of the frame 12 by the proximal valve connector 914, the proximal end 16 of the frame is prevented from moving relative to the support tube. As such, movement of the actuator member 922 in a proximal direction causes movement of the actuator screw 902 in a proximal direction (because the actuator member is threaded onto the screw), thereby causing the frame 12 to foreshorten axially and expand radially. Alternatively, the frame 12 can be expanded by moving the support tube 920 distally while holding the actuator member 922 stationary, or moving the support tube distally while moving the actuator member 922 proximally.

After the frame 12 is expanded to a desired radially expanded size, the frame can be locked at this radially expanded size as described herein. Locking the frame can be achieved by rotating the locking tool 924 in a clockwise direction causing the notched portion 926 of the locking tool to engage the notched portion 918 of the locking nut 916, thereby advancing the locking nut distally along the actuator screw 902. The locking tool 924 can be so rotated until the locking nut 916 abuts an internal shoulder at the distal end of the sleeve 912 and the locking nut 916 cannot advance distally any further (see FIG. 20). This will prevent the screw 902 from advancing distally relative to the sleeve 912 and radially compressing the frame 12. However, in the illustrated embodiment, the nut 916 and the screw 902 can still move proximally through the sleeve 912, thereby allowing additional expansion of the frame 12 either during implantation or later during a valve-in-valve procedure.

Once the frame 12 is locked in radially expanded state, the locking tool 924 can be rotated in a direction to move the locking tool proximally (e.g., in a counter-clockwise direction) to decouple the notched portion 926 from the notched portion 918 of the locking nut 916 and to unscrew the locking tool from the actuator screw 904. Additionally, the actuator member 922 can be rotated in a direction to unscrew the actuator member from the lower portion 906 of the actuator screw 902 (e.g., the actuator member 922 can be configured to disengage from the actuator screw when rotated counter-clockwise). Once the locking tool 924 and the actuator member 922 are unscrewed from the actuator screw 904, they can be removed from the patient along with the support tube 920, leaving the actuator screw and the sleeve 912 connected to the frame 12 with the frame 12 locked in a particular, radially expanded state. Further details regarding the expansion and locking mechanisms 900, including the manner in which the frame can be locked in the radially expanded configuration, can be found in, for example, U.S. Publication 2018/0153689, which is incorporated herein in its entirety.

As shown in FIGS. 20-21, in some particular embodiments, a delivery apparatus 502 can further comprise a crimping mechanism 1000. A delivery assembly 500 can include a prosthetic valve (e.g., a prosthetic valve 10 or any of the other prosthetic valves disclosed herein) and a delivery apparatus 502 having crimping mechanism 1000. The crimping mechanism 1000 can be part of the delivery apparatus 502 and can facilitate crimping of a prosthetic valve, such as prosthetic valve 10, after the prosthetic valve 10 has been exposed from the outer sheath 510 inside the patient, as discussed in more detail below.

In the embodiment of FIGS. 20-21, the delivery apparatus 502 includes actuator mechanisms 919 and the crimping mechanism 1000 therefore is described in connection with actuator mechanisms 919. In alternative embodiments, the crimping mechanism 1000 can be used with various other types of actuators, such as actuator members 508 (described above). Because the crimping mechanism 1000 is coupled to part of the delivery apparatus 502 rather than being coupled to prosthetic valve 10 directly, the crimping mechanism 1000 does not affect the crimp profile of the prosthetic valve and does not require a separate de-coupling step for disconnecting the crimping mechanism from the prosthetic valve after the prosthetic valve has been fully deployed at the desired implantation site.

As previously described, the delivery apparatus can include one or more actuator mechanisms 919 (e.g., three in the illustrated embodiment) releasably coupled to corresponding expansion and locking mechanisms 900, as previously described. Each actuator mechanism 919 transmits forces from the handle 504 of the delivery apparatus to a respective expansion and locking mechanism 900. The crimping mechanism 1000 can comprise a plurality of canals, rings, or eyelets 1002 mounted on respective actuator mechanisms 919, a tension member 1004, and a tension member actuator 1008. In the illustrated embodiment, each eyelet 1002 is disposed on an outer surface of a respective actuator mechanism 919 so as to face away from the longitudinal axis A of the prosthetic valve 10. For example, each eyelet 1002 can be mounted on a respective support tube 920 and oriented to face away from the longitudinal axis A. However, in other embodiments, each eyelet 1002 may be disposed on an outer surface of a respective actuator mechanism 919 (e.g., a support tube 920 of the actuator mechanism) so as to face toward the longitudinal axis A of the prosthetic valve 10.

Each eyelet 1002 can have an inner lumen 1010 sized such that a portion of the tension member 1004 can extend through the lumen 1010. In the illustrated embodiment, each eyelet 1002 has a flat-oval cross-sectional shape (e.g., a shape comprising an oval with flat sides). However, in other embodiments, each eyelet 1002 can have any of various shapes in cross-section such as, without limitation, square, rectangle, circle, triangle, ellipse, and/or combinations thereof.

Referring now to FIG. 21, the tension member 1004 can extend through the lumen 1010 of the eyelets 1002, thus forming a loop around the support tubes 920 of the delivery apparatus 502. The tension member 1004 can have a first end and a second end which can be coupled together (e.g., by knotting, bonding, or other type of connection) to form a closed loop, which is coupled to the tension member actuator 1008.

The tension member can be, for example, a suture (e.g., a single filament suture or a multi-filament suture), a flexible wire (e.g., a metal wire formed from stainless steel, Nitinol or other suitable metals), a cable (e.g., a braided cable formed from metal or polymeric strands) or any other similar materials that can be threaded through the eyelets and placed in tension to radially compress the prosthetic valve as described herein.

In alternative embodiments, the actuator mechanisms 919 can comprise different types of retaining members other than eyelets 1002 for retaining the tension member 1004 in a loop around the support tubes. For example, each support tube 920 can include a retaining member in the form of an open hook with the tension member 1004 extending through the hooks to form a loop. In another example, each retaining member can take the form of a pair of axially-spaced posts or projections extending radially outwardly from the outer surfaces of the support tubes 920 with the tension member 1004 extending through each pair of posts or projections on each support tube to form a loop.

As noted above, the crimping mechanism 1000 also comprises a tension member actuator 1008. The actuator 1008 can be, for example, a pull cable, a wire, or shaft, and can have a proximal end portion coupled to the handle 504 and a distal end portion coupled to the tension member 1004. The handle 504 can include a knob or other actuation mechanism operatively coupled to the actuator 1008 to apply a force to the actuator 1008 and thereby to the tension member 1004, as described in further detail below.

The distal end portion of the actuator 1008 can be connected to an attachment member 1012. The attachment member 1012 in turn can be connected to the tension member 1004 such that the actuator 1008 can apply a tensile force to the tension member 1004. In the illustrated embodiment, the attachment member 1012 is a ring or loop disposed at the distal end portion of the actuator 1008 through which the tension member 1004 can extend. In other embodiments, the attachment member 1012 can be, for example, a clip, a hook, or other such mechanism configured to couple the actuator 1008 to the tension member 1004. An optional sheath or tube 1006 can extend over the actuator 1008 the length of the delivery apparatus from the handle to the tension member 1004. A portion of the loop formed by the tension member 1004 can extend into the sheath 1006. The sheath 1006 can have a proximal end portion connected to the handle 504 of the delivery apparatus.

In some embodiments, in place of a separate tension member actuator 1008, the tension member 1004 can extend from the handle through the lumen of the tube 1006 and outwardly through a distal opening of the tube 1006 through the inner lumens 1010 of the eyelets 1002 and then back into the distal opening and through the lumen of the tube 1006 to the handle such that the tension member forms one long loop portion that can extend from the handle, along the length of the delivery apparatus, through the eyelets 1002 and around the actuator mechanisms 919.

The actuator 1008 and the sheath 1006 can extend along an axis that is radially offset inwardly from the support tubes 920 toward the longitudinally axis of the delivery apparatus. For example, as shown in the illustrated embodiment, the actuator 1008 and the sheath 1006 can extend longitudinally alongside the inner shaft 506, which can extend along the longitudinal axis of the delivery apparatus. In this manner, the actuator 1008 can be connected to the tension member 1004 (such as via the connector 1012) at a location radially inwardly of the actuator mechanisms 919 and applying a proximally directed force to the actuator 1008 is effective to pull the actuator mechanisms 919 radially inwardly via the tension member 1004 to compress the prosthetic valve, as further described below.

The crimping mechanism 1000 can be used to radially compress a prosthetic heart valve, such as prosthetic heart valve 10, in the following exemplary manner. The prosthetic valve 10 can be connected to the delivery apparatus 502 in the manner described above. The distal end portion of the delivery apparatus 502 (along with prosthetic valve 10) can be advanced through the vasculature of a patient to a selected implantation site. The prosthetic valve 10 can then be deployed at the implantation site (e.g., the native aortic annulus).

In some cases, after deployment from the sheath 510, the prosthetic valve 10 can expand slightly due to the inherent resiliency of the frame 12. For example, in some embodiments, the prosthetic valve can resiliently expand to a natural diameter of 22 mm. In such cases, the physician can use the crimping mechanism 1000 to compress the prosthetic valve 10 to a fully compressed configuration such that it can be more easily positioned at the implantation site. The physician can apply an axial force in the proximal direction (e.g., a pulling force) to the actuator 1008 (and thus the tension member 1004) using the handle 504. Applying an axial force to the tension member 1004 places the tension member 1004 in tension around the support tubes 920, which in turn applies a radially inwardly directed force to each support tube 920, pulling the support tubes 920 (and therefore the actuator mechanisms 919) radially inward toward one another. The movement of the support tubes 920 in turn transmits the radial force applied by the tension member 1004 to the frame 12 of the prosthetic valve 10, thereby radially compressing the frame 12.

Alternatively, in some cases, the physician can use the crimping mechanism 1000 to maintain the valve in a fully crimped configuration prior to the retraction of the outer sheath 510, thus preventing or at least mitigating any expansion caused by the inherent resiliency of the frame 12. Maintaining the crimped configuration of the prosthetic valve 10 during retraction of the sheath 510 can help mitigate radial or axial 'jumps' (i.e., unplanned movements of the prosthetic valve) caused by inherent frame expansion, and thereby maximize the physician's control over positioning the prosthetic valve. In this manner, the mechanism 1000 is used to maintain the prosthetic valve in the radially compressed state, rather than for crimping the prosthetic valve after partial or full expansion.

Once the prosthetic valve 10 is positioned at the desired implantation site, the applied force on the actuator 1008 can be released (thereby releasing tension on the tension member 1004) and the prosthetic valve can be expanded using the expansion and locking mechanisms 900 as previously described herein. The delivery apparatus can then be released from the prosthetic valve and removed from the body. Because the tension member 1004 is mounted on components of the delivery apparatus and not the prosthetic valve, a separate release or de-coupling step for the crimping mechanism is not needed.

Additionally, in some cases, once the prosthetic valve has been at least partially expanded the physician can determine whether the prosthetic valve needs to be repositioned. In such cases, the physician can use the crimping mechanism 1000 to fully compress the prosthetic heart valve using the method described above in order to reposition the prosthetic valve 10 at the implantation site. Once the prosthetic valve 10 has been repositioned, it can be expanded using the expansion and locking mechanisms 900 as previously described herein. The prosthetic valve 10 can be re-crimped, re-positioned and re-expanded multiple times, as needed. In some cases, the prosthetic valve 10 can be fully compressed and "recaptured" (retracted back into the sheath 510) and then removed from the patient's body.

Crimping mechanism 1000 advantageously does not require distal advancement of the sheath 510 in order to re-crimp the prosthetic valve 10. This mitigates the likelihood of causing trauma to the patient's anatomy by advancing sheath 510 distally. Distal advancement of a sheath without an attached nosecone can result in rubbing or scraping of the patient's anatomy, which can, for example, result in stroke in cases where the patient's anatomy has calcified.

Additionally, the crimping mechanism 1000 allows the prosthetic valve 10 to be re-crimped in place without significant distal or proximal movement of the prosthetic valve. This allows the physician to re-crimp the prosthetic valve 10 and fine-tune its positioning without having to restart the positioning process from the beginning (e.g., by recapturing the prosthetic valve into the sheath 510). In some cases, recapturing the prosthetic valve into the sheath for repositioning can result in damage to the prosthetic valve. The crimping mechanism 1000 allows the valve to be re-crimped and repositioned while mitigating the risk of damage to the prosthetic valve because the prosthetic valve does not need to be re-inserted into sheath 510.

The crimping mechanism 1000 can be used with any of the prosthetic valves described herein (e.g., prosthetic valves 10, 100, 200, 300, 400, 700, and 800). For example, crimping mechanism 1000 can be used to compress a prosthetic valve that normally assumes a tapered shape while in the compressed configuration, such as prosthetic valve 800 having expansion actuators (e.g., the expansion and locking mechanisms 900), into a cylindrical or substantially cylindrical configuration to facilitate positioning/re-positioning of the prosthetic valve inside the patient's body and/or recapture of the prosthetic valve back into the sheath 510.

Explaining further, after the outer sheath 510 of the delivery apparatus 502 is retracted, the prosthetic valve 800 normally assumes a tapered configuration wherein a diameter of the proximal end of the prosthetic valve (e.g., the outflow end 826 when the prosthetic valve is mounted for retrograde delivery) is greater than a diameter of the distal end of the prosthetic valve (e.g., the inflow end 824 when the prosthetic valve is mounted for retrograde delivery) (see e.g., FIG. 17C). The physician can actuate the actuator 1008 of the crimping mechanism 1000, thereby applying radial forces to the support tubes 920 of the delivery apparatus 502. Because the radial forces are applied to the support tubes 920 rather than to the frame of the prosthetic valve itself, the crimping mechanism 1000 can compress the outflow end 826 of the prosthetic valve 800 to a greater degree than the inflow end 824. Because the crimping mechanism is offset to one side of the prosthetic valve, it can compensate for the larger diameter of the outflow end 826 of the prosthetic valve 800, thus crimping the prosthetic valve 800 into a substantially cylindrical configuration.

In alternative embodiments, the crimping mechanism 1000 can be incorporated in delivery apparatuses having other types of actuator assemblies and can be used with prosthetic valves having other types of actuators than the type shown in FIGS. 20-21. Further, the tension member 1004 need not be looped around components of the actuator assemblies of the delivery apparatus. For example, a delivery apparatus can have a plurality of circumferentially spaced connecting members, such as in the form of fingers or shafts, that form a releasable connection with a prosthetic valve but do not necessarily function as actuators for expanding the prosthetic valve, such as disclosed in U.S. Publication No. 2012/0239142, which is incorporated herein by reference. In such cases, the tension member 1004 can be looped around the connecting members in the same manner as shown in FIGS. 20-21 and can function to radially compress the prosthetic valve in situ.

Referring now to FIGS. 22-25, in some particular embodiments, in lieu of or in addition to crimping mechanism 1000, a delivery assembly 500 can comprise a prosthetic valve (e.g., a prosthetic valve 10 or any of the other prosthetic valves disclosed herein), a delivery apparatus 502, and a crimping mechanism 1100. The crimping mechanism 1100 can be a separate component from the delivery apparatus 502 and can be inserted into and removed from the delivery apparatus 502. In alternative embodiments, the crimping mechanism 1100 can be incorporated into the delivery apparatus 502 such that it is not a separable component. The delivery apparatus 502 of FIGS. 22, 23 and 25 has actuator mechanisms 919 (which can be coupled to actuators 900 on the prosthetic valve 10) in lieu of actuators 508 but can have any of the other components of the delivery apparatus 502 of FIGS. 13-14 described above.

The crimping mechanism 1100 can facilitate crimping of a prosthetic valve, such as prosthetic heart valve 10, after the prosthetic valve 10 has been exposed from the outer sheath 510 inside the patient, as discussed in more detail below. Although described with respect to a delivery apparatus having actuator mechanisms 919, the crimping mechanism 1100 can be used with a delivery apparatus having any of various types of actuator mechanisms that couple a prosthetic valve to the delivery apparatus and are configured to expand and compress the prosthetic valve. Additionally, the crimping mechanism 1100 can also be used with delivery apparatuses that are configured to deliver self-expanding or balloon expandable prosthetic valves.

The crimping mechanism 1100 is similar to crimping mechanism 1000 except that components of the crimping mechanism 1100 are not connected to the actuator mechanisms 919 of the delivery apparatus 502, but rather the crimping mechanism 1100 is selectively extendable and retractable from the sheath 510 of the delivery apparatus 502. Because the crimping mechanism 1100 can be fully retracted into the outer sheath 510 unless and until it is needed, the crimping mechanism 1100 does not affect the crimp profile of the prosthetic valve.

The crimping mechanism 1100 can comprise a tension member actuator 1102 and a tension member 1104. The tension member actuator 1102 can be, for example, an elongated sheath or tube having a lumen extending therethrough. The tension member actuator 1102 can extend through a lumen of the outer shaft 510 and can have a proximal end portion operatively coupled to the handle 504.

In some embodiments, the crimping mechanism can extend through a respective lumen of a multi-lumen shaft 509 of the delivery apparatus 502, wherein the multi-lumen shaft extends coaxially through the outer shaft 510. Each of the actuator mechanisms 919 can extend through respective lumens of the multi-lumen shaft 509. Similarly, the inner shaft 506 can extend through a respective lumen of the multi-lumen shaft 509. The lumen that receives the inner shaft 506 can be center lumen (centrally located along the shaft 509), while the lumens that receive the crimping mechanism 1100 and the actuator mechanisms 919 can be radially offset from the center of the shaft 509 and can be spaced apart from each other in a circumferential direction.

The crimping mechanism 1100 can be moved between a retracted configuration for delivery into the patient's body, wherein the crimping mechanism 1100 is contained within the sheath 510 of the delivery apparatus (and at least partially retracted into the multi-lumen shaft 509 if the delivery apparatus includes the shaft 509), and a deployed configuration for use, wherein the distal end portion of the crimping mechanism 1100 extends from the distal end of the sheath 510 (and the multi-lumen shaft 509 if the delivery apparatus includes the shaft 509). The crimping mechanism 1100 can be moved between the retracted configuration and the deployed configuration by manually moving the crimping mechanism 1100 proximally or distally relative to the sheath 510 (and the shaft 509 if one is provided), by actuating an actuator (e.g., a knob or lever) on the handle 504 of the delivery apparatus that controls longitudinal movement of the crimping mechanism 1100, and/or moving the sheath 510 proximally or distally relative to the crimping mechanism.

Figure 24A:
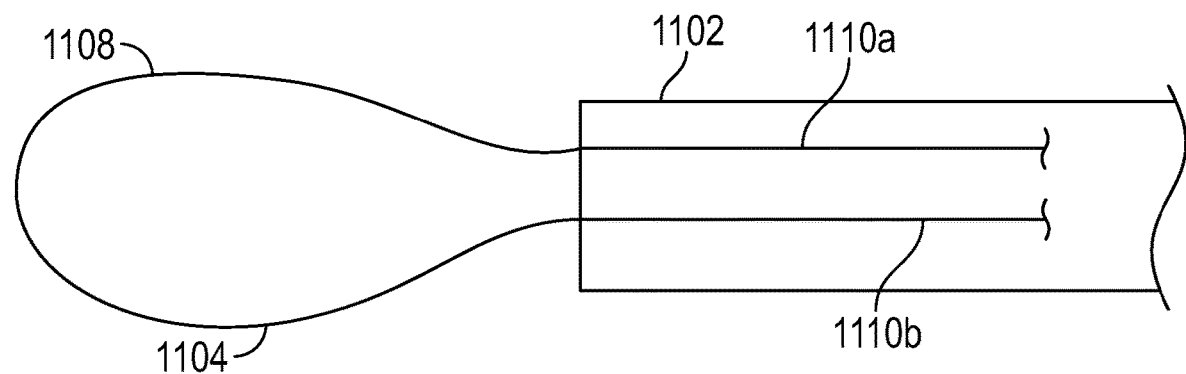
FIG. 24A is a cross-sectional view of an exemplary crimping mechanism.

The tension member 1104 can extend through the lumen of the tension member actuator 1102 and outwardly through a distal opening of the tension member actuator 1102 and then back into the distal opening and through the lumen of the actuator 1102 such that the tension member 1104 forms a loop portion 1108 that can extend from the distal end of the tension member actuator 1102 and around the actuator mechanisms 919. In some embodiments, as shown in FIG. 24A, the loop portion 1108 can essentially extend the entire length of the tension member 1104 and can have two segments 1110a, 1110b that extend through the tension member actuator 1102 and have proximal end portions that can be operatively coupled to the handle 504 or can be exposed at the proximal end of the delivery apparatus for manipulation by a user.

The tension member 1104 can be, for example, a suture (e.g., a single filament suture or a multi-filament suture), a flexible wire (e.g., a metal wire formed from stainless steel, Nitinol or other suitable metals), a cable (e.g., a braided cable formed from metal or polymeric strands), a strip of material (e.g., a polymer or metal strip), or any other similar materials that can be bent or formed into a loop and placed in tension to radially compress the prosthetic valve as described herein. In some embodiments, the tension member 1104 can comprise a shape memory material such that the loop portion 1108 can radially expand under its own resiliency when deployed from the tension member actuator 1102. For example, the tension member 1104 can comprises a metal wire, such as a Nitinol wire, a cable, or a metal or polymeric strip such that the loop portion 1108 can radially expand under its own resiliency when deployed from the tension member actuator 1102.

Figure 24B:
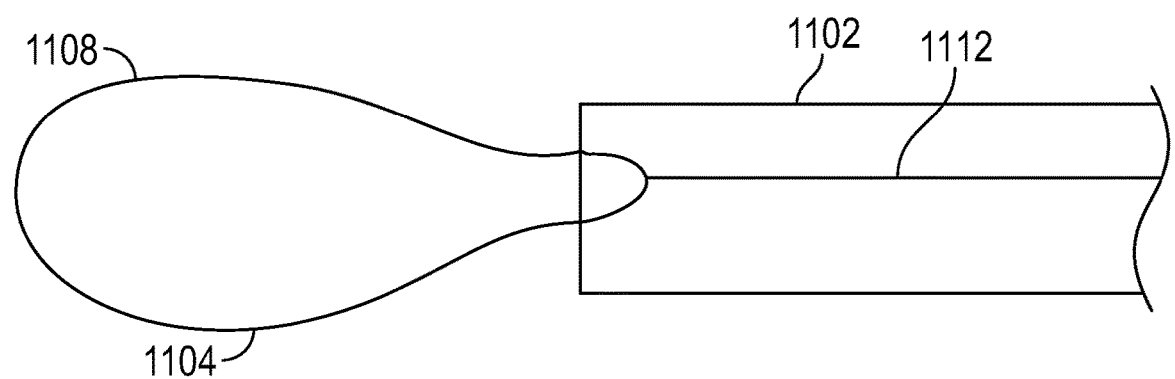
FIG. 24B is a cross-sectional view of another exemplary crimping mechanism.

In other embodiments, as shown in FIG. 24B, the loop portion 1108 comprises a distal segment of the tension member and the tension member further includes a proximal segment 1112 that does not form part of the loop. The proximal segment 1112 extends through the tension member actuator 1102 toward the handle 504. The proximal segment 1112 has a distal end portion connected to the loop portion 1108 and a proximal end portion, which can be operatively coupled to the handle or can be exposed at the proximal end of the delivery apparatus. The proximal segment 1112 can be formed from the same or different material(s) as the loop portion 1108. For example, the loop portion 1108 can be formed from any of the materials mentioned above, while the proximal segment 1112 can be relatively stiffer or more rigid than the loop portion 1108 to enhance the pushability of the tension member. In such cases, the proximal segment 1112 can be, for example, a shaft, or rod, or a wire (where the loop portion 1108 comprises a wire, the proximal segment 1112 can be a stiffer wire).

The size of the loop portion 1108 can be varied by adjusting the amount of the loop portion 1108 that extends from the distal end of the tension member actuator 1102. This can be accomplished by moving the tension member actuator 1102 proximally or distally relative to the tension member 1104 and/or moving the tension member 1104 proximally or distally relative to the tension member actuator 1104. The handle 504 can include a knob, lever, or other actuation mechanism configured to vary the size of the loop portion 1008 by moving the tension member actuator 1102 proximally or distally with respect to the tension member 1104 and/or a knob, lever, or other actuation mechanism configured to move the tension member 1104 proximally or distally with respect to the tension member actuator 1102. Alternatively, the size of the loop portion 1108 can be varied by manually moving the tension member actuator 1102 and/or the tension member 1104 proximally or distally relative to each other.

Figure 25:
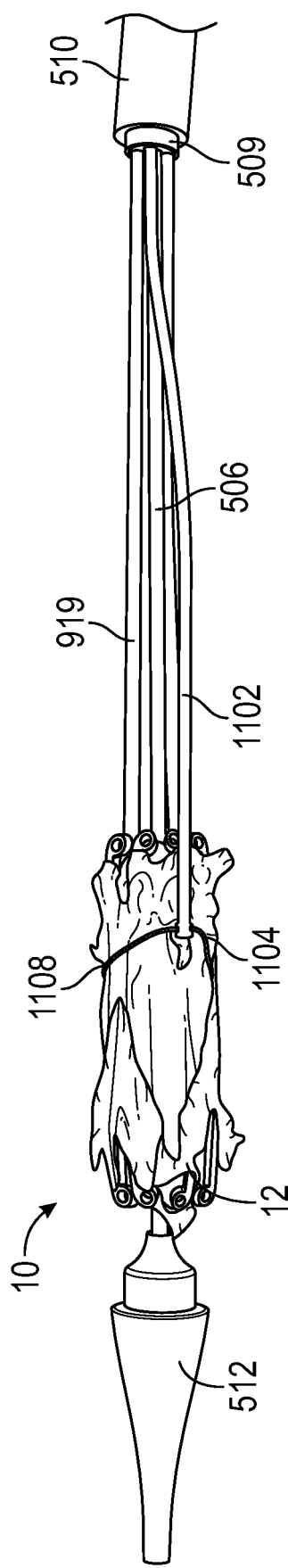
FIG. 25 is a side elevational view of the delivery apparatus and prosthetic valve of FIG. 22, showing the crimping mechanism in a contracted configuration.

Referring to FIG. 22, the loop portion 1108 can be radially enlarged by exposing a greater amount of the loop portion 1108 from the distal end of the tension member actuator 1102. When in the radially enlarged or expanded configuration, the loop portion 1108 can be sized to be placed over a selected crimping location on the prosthetic valve (as shown in FIG. 23) or the delivery apparatus. Referring to FIG. 25, the loop portion 1108 can be contracted by retracting a portion of the loop portion 1108 into the tension member actuator 1102. When in the contracted configuration, the loop portion 1108 can apply a radially compressive force to the selected crimping location on the prosthetic valve 10, or on the delivery apparatus 502 (e.g., on the actuators 919) so as to radially compress the prosthetic valve, as shown in FIG. 25.

The crimping mechanism 1100 can be used to radially compress a prosthetic heart valve, such as prosthetic heart valve 10 having actuators 900, in the following exemplary manner. The prosthetic valve 10 can be connected to the delivery apparatus 502 in the manner described above. The distal end portion of the delivery apparatus 502 (along with prosthetic valve 10) can be advanced through the vasculature of a patient to a selected implantation site. The prosthetic valve can then be deployed at the implantation site (e.g., the native aortic annulus). During delivery, the crimping mechanism 1100 can be stored within the sheath 510. Except for the portion of the loop 1108 extending around the actuator mechanisms 919, the crimping mechanism 1100 also can be stored in the shaft 509 (if a shaft 509 is provided)

In some cases, once the prosthetic valve has been at least partially expanded the physician can determine whether the prosthetic valve needs to be repositioned. In such cases, the physician can use the crimping mechanism 1100 to fully compress the prosthetic heart valve using the method described above in order to reposition the prosthetic valve 10 at the implantation site. The physician can deploy the distal end portion of the crimping mechanism 1100 from the sheath 510 and then increase the size of the loop portion 1108 that extends from the distal end of the tension member actuator 1102. The size of the loop portion 1108 that extends from the tension member actuator 1102 can be increased by either: (i) moving the tension member 1104 distally while holding the tension member actuator 1102 stationary; (ii) by moving the tension member 1104 distally while retracting the actuator 1102 proximally; or (iii) by holding the tension member 1104 stationary while moving the tension member actuator 1102 proximally. As noted above, the loop portion 1108 can be configured to self-expand to a larger diameter as more of the loop portion 1108 is exposed from the tension member actuator 1102. After increasing the size of the loop portion 1108, the physician can move the tension member actuator 1102 and the tension member 1104 in order to slide the loop portion 1108 to a selected crimping location, such as around the circumference of the prosthetic valve 10. For example, the tension member actuator 1102 and the tension member 1104 can be slid distally over prosthetic valve 10.

Once the tension member 1104 is in place around the prosthetic valve 10, the physician can contract the loop portion by: (i) moving the tension member actuator 1102 distally while holding the tension member 1104 stationary; (ii) retracting the tension member 1104 proximally while moving the actuator 1102 distally; or (iii) retracting the tension member 1104 proximally while holding the actuator 1102 stationary. This places the loop portion 1108 of the tension member 1104 in tension around the frame 12, which in turn applies a radially inwardly directed force to the frame 12, thereby radially compressing the frame 12.

In other embodiments, the selected crimping location can be on a portion of the delivery apparatus rather than on the prosthetic valve itself, such as on the actuators 919 of the delivery apparatus. In such embodiments, contracting the loop portion 1108 places the loop portion 1108 in tension around the actuators 919, which in turn applies a radially inwardly directed force to each actuator 919, pulling the actuators 919 radially inward toward one another. The movement of the actuators 919 in turn transmits the radial force applied by the tension member 1104 to the frame 12, thereby radially compressing the prosthetic valve.

Once the re-compressed prosthetic valve 10 has been repositioned at the desired implantation site, the applied force on the tension member actuator 1102 can be released (thereby releasing tension on the tension member 1104), and the size of the loop portion 1108 can be increased as described previously such that the loop portion can moved off the selected crimping location. The crimping mechanism 1100 can then be retracted proximally into the sheath 510 of the delivery apparatus 502. Once the crimping mechanism 1100 has been retracted (or at least moved to a location spaced from the prosthetic valve), the prosthetic valve 10 can be expanded using the expansion and locking mechanisms 900 as previously described herein.

In some cases, after deployment from the sheath 510, the prosthetic valve 10 can expand slightly due to the inherent resiliency of the frame 12. In such cases, the physician can use the crimping mechanism 1100 in the manner described above to further crimp the prosthetic valve 10 to facilitate positioning the valve and/or crossing the native annulus.

In some cases, the loop portion 1108 can be placed in tension around the prosthetic valve 10 while the prosthetic valve is contained within the sheath 510 during delivery. In this manner, after the prosthetic valve 10 is deployed from the sheath 510 inside the patient's body (e.g., at or near the implantation site), the crimping mechanism 1100 can maintain the prosthetic valve in a fully compressed state while the physician positions the prosthetic valve at the desired implantation site.

Additionally, in some cases, the prosthetic valve can be removed from the patient's body by recapturing the prosthetic valve back into the sheath using the crimping mechanism 1100. In such cases, the physician can use the crimping mechanism 1100 to fully crimp the prosthetic valve 10, as described above. The sheath 510 can be moved distally relative to the prosthetic valve 10 to recapture the valve (and/or the prosthetic valve can be retracted proximally back into the sheath) and the delivery apparatus (and thereby the prosthetic valve) can be removed from the body.

In some embodiments, the entire length of the tension member 1104 (including the loop portion 1108) can be contained within the actuator 1102, and the entire distal end portion of the crimping mechanism can be housed within the shaft 509 and/or the sheath 510 during delivery of the prosthetic valve. When the crimping mechanism 1100 is needed to radially compress the prosthetic valve, the crimping mechanism 1100 can be advanced from the shaft 509 and/or the sheath 510 and the loop portion 1108 can be advanced from the distal end portion of the actuator 1102. The loop portion 1108 can then be advanced to a location distal to the nose cone 512 (and distal to a guidewire extending through the nose cone if a guidewire is used in the procedure), and then retracted in the proximal direction to slide the loop portion 1108 over the nose cone to the selected crimping location (on the prosthetic valve or on the actuators 919). If needed or desired, the guidewire can be retracted to facilitate positioning of the loop portion 1108 at a location where it can be retracted back over the nose cone and the prosthetic valve.

In some embodiments, the crimping mechanism 1100 can be separate from the delivery apparatus and can be delivered after the prosthetic valve is advanced to the vicinity of the implantation site by the delivery apparatus. For example, after delivering the prosthetic valve into the patient's body it is determined that the crimping mechanism is needed to radially compress the prosthetic valve, the crimping mechanism 1100 can be inserted through the shaft 509 and/or the sheath 510 to position the distal end portion of the crimping mechanism adjacent the prosthetic valve. The crimping mechanism 1100 can then be used to radially compress the prosthetic valve as previously described.

The crimping mechanism 1100 can be used with any of the prosthetic valves described herein (e.g., prosthetic valves 10, 100, 200, 300, 400, 700, and 800). For example, crimping mechanism 1100 can be used to compress a prosthetic valve that normally assumes a tapered shape while in the compressed configuration, such as prosthetic valve 800, into a cylindrical or substantially cylindrical configuration for re-positioning inside the patient's body.

Explaining further, after the outer sheath 510 of the delivery apparatus 502 is retracted, the prosthetic valve 800 normally assumes a tapered configuration wherein a diameter of the outflow end 826 is greater than a diameter of the inflow end 824 (see e.g., FIG. 17C). The physician can expand the loop portion 1108 of the crimping mechanism 1100 and slide the mechanism 1100 distally until it is positioned around the outflow end 826 of the prosthetic valve 800. The physician can actuate the tension member actuator 1102 of the crimping mechanism, thereby applying radial forces to the distal end 826 of the prosthetic valve and compressing the outflow end to substantially the same diameter as the inflow end 824. Because the crimping mechanism is offset to one side of the prosthetic valve, it can compensate for the larger diameter of the outflow end 826 of the prosthetic valve 800, thus crimping the prosthetic valve 800 into a substantially cylindrical configuration.

In alternative embodiments, the crimping mechanism 1100 can be incorporated in delivery apparatuses having other types of actuator assemblies and can be used with prosthetic valves having other types of actuators than the type shown in FIGS. 22-24. Further, the tension member 1104 need not be looped around the frame 12 of the prosthetic valve or around components of the actuator assemblies of the delivery apparatus. For example, a delivery apparatus can have a plurality of circumferentially spaced connecting members, such as in the form of fingers or shafts, that form a releasable connection with a prosthetic valve but do not necessarily function as actuators for expanding the prosthetic valve, such as disclosed in U.S. Publication No. 2012/0239142, which is incorporated herein by reference. In such cases, the tension member 1104 can be looped around the connecting members in the same manner as shown in FIG. 20 and can function to radially compress the prosthetic valve in situ.

Figure 26:
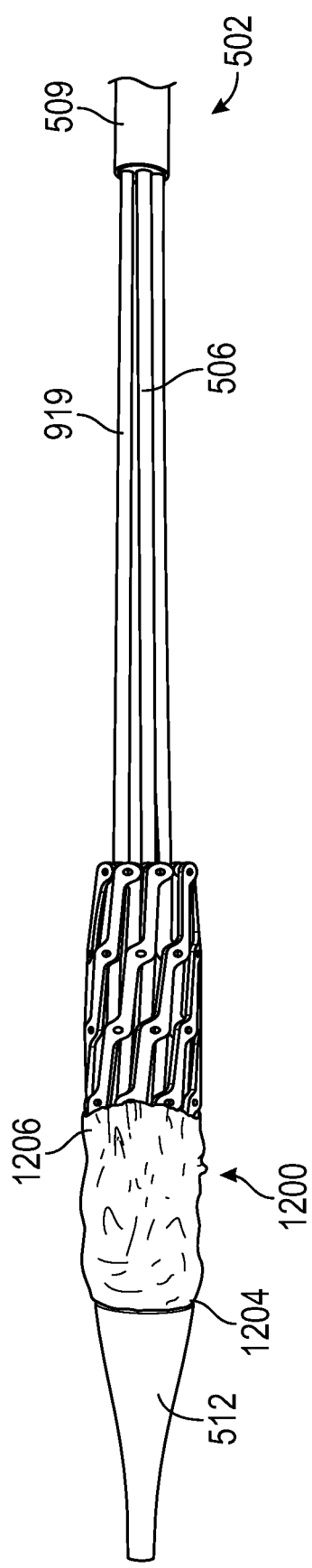
FIG. 26 is a side elevational view of the distal end portion of a delivery apparatus including a capsule and a prosthetic valve coupled to the delivery apparatus, according to one embodiment, showing the capsule extending over the prosthetic valve in a radially compressed state.
Figure 27:
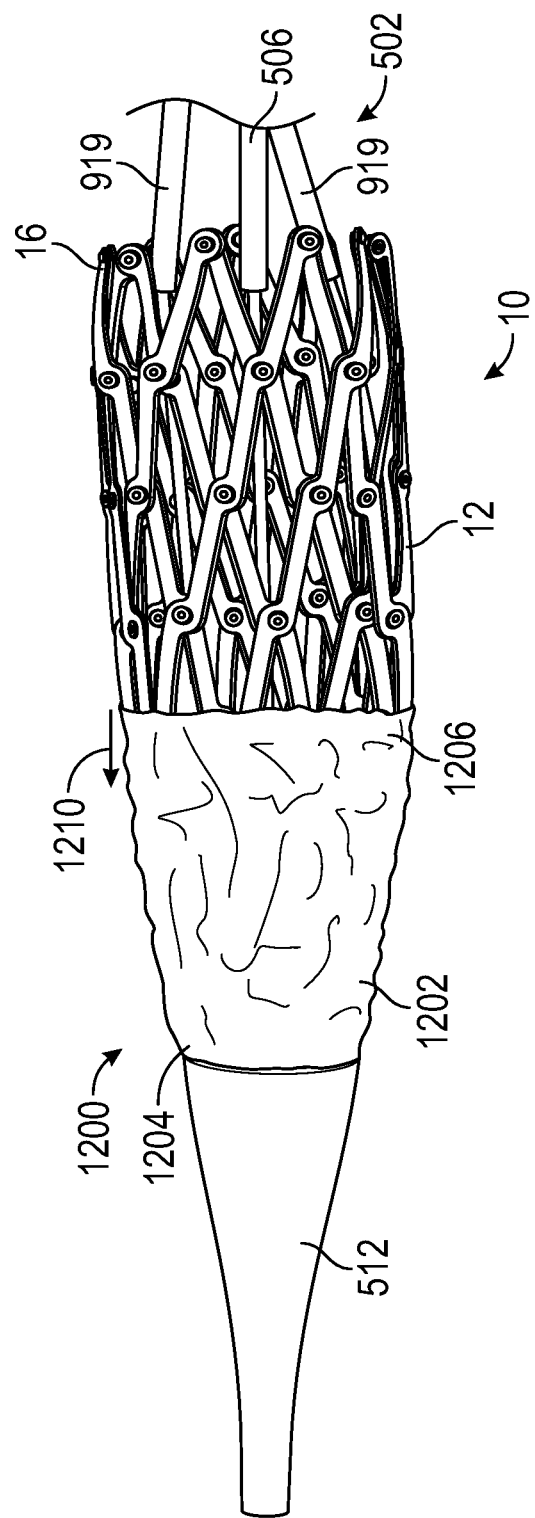
FIG. 27 is another side elevational view of the delivery apparatus and prosthetic valve of FIG. 26, showing the prosthetic valve in a radially expanded state.

Referring now to FIGS. 26-27, in some particular embodiments, a delivery apparatus 502 can further comprise a capsule 1200. The capsule 1200 can be coupled to a proximal end portion of the nose cone 512 of the delivery apparatus 502 and can be configured to extend over and engage a distal end portion of a prosthetic valve, such as prosthetic valve 10, when the prosthetic valve 10 is mounted on delivery apparatus 502 in a radially compressed state.

Due to the presence of the inner valvular structure (e.g., the prosthetic leaflets 22) substantially within the middle portion of the frame, the diameter at the inflow and outflow end portions of the prosthetic valve 10 can be radially compressed to a slightly smaller diameter than the diameter at a central portion of the prosthetic valve. As such, the addition of the capsule 1200 over the inflow or distal end portion of the prosthetic valve has a minimal effect on the crimp profile of the prosthetic valve. In some embodiments, the capsule device 1200 functions in lieu of the outer sheath of the delivery apparatus in maintaining the prosthetic valve in a fully compressed configuration during the implantation procedure. In such embodiments, as shown in FIG. 25, the delivery apparatus 502 need not include an outer sheath 510, and the actuators 919 can extend through the lumens of multi-lumen shaft 509. In other embodiments, the delivery apparatus 502 can comprise a sheath 510 in addition to the capsule device 1200. The delivery apparatus 502 of FIGS. 26-27 can include any of the other components described above in connection with FIG. 13 and not described here for the sake of brevity.

By virtue of the frame 12 being tapered along its distal end portion, the frame acts as an expanding wedge mechanism to push the capsule 1200 off the distal end portion of the prosthetic valve when the prosthetic valve is radially expanded. When the prosthetic valve is radially expanded, the capsule slides distally off of and automatically disengages from the distal end portion of the prosthetic valve, therefore no additional delivery apparatus components and/or steps are needed to remove the capsule 1200 from the prosthetic valve 10.

The capsule 1200 can be in the form of a tube or sleeve 1202 having a first, or distal end portion 1204 and a second, or proximal end portion 1206. The distal end portion 1204 of the sleeve 1202 can be coupled to the nose cone 512 and the proximal end portion 1206 of the sleeve can be configured to at least partially encapsulate the distal end portion of the prosthetic valve 10. The proximal end portion 1206 of the sleeve 1202 can be connected to the nose cone 512 with an adhesive, by welding, fasteners, and/or other suitable connection means. In alternative embodiments, the sleeve 1202 can be integrally formed with the nose cone 512, such as by molding the nose cone 512 and the sleeve 1202 together to form a nose cone and sleeve having a one-piece, unitary construction.

The sleeve 1202 desirably is sized to extend over the tapered portion of the prosthetic valve when it is in the radially compressed state. For example, as noted above, the prosthetic valve 10 (which has a cylindrical frame when radially expanded) is slightly tapered from about the midsection of the prosthetic valve (halfway between the proximal and distal ends) to the distal end when the prosthetic valve it is held in a radially compressed state due to the bulk of the soft components of the prosthetic valve being generally located within the middle of the frame. When intended for use with such a prosthetic valve, the sleeve can be sized to extend half the length of the prosthetic valve or less than half of the length of the prosthetic valve. In other embodiments (for example, embodiments wherein the prosthetic valve is tapered over more than half of the length of the prosthetic valve when in the compressed state, such as shown in FIG. 17C) the sleeve 1202 can be sized to extend over more than half of the length of the prosthetic valve.

In some embodiments, the capsule device can comprise a textile (a fabric or a braided material) or a non-textile piece of material, such as in the form of a polymer membrane. Suitable materials for forming a textile or non-textile sleeve include, for example, polyethylene terephthalate (PET), polytetrafluoroethylene (PTFE) (e.g., Teflon™), polyurethane, polypropylene, or polyamine. In other embodiments, the sleeve 1202 can comprise multiple textile and/or non-textile layers. For example, the sleeve can have a textile (e.g., fabric) inner layer and a non-textile outer layer, or a non-textile inner layer and a textile outer layer.

A delivery apparatus 502 comprising a capsule 1200 can be used to implant a prosthetic heart valve, such as prosthetic heart valve 10, in the following exemplary manner. The prosthetic valve 10 can be connected to the delivery apparatus 502 and radially compressed in the manner described previously. The capsule 1200 can be placed over the distal end portion of the prosthetic valve 10. The distal end of the delivery apparatus (along with prosthetic valve 10) can be advanced through the vasculature of a patient to a selected implantation site (e.g., the native aortic annulus).

At or near the selected implantation position, the prosthetic valve 10 can be deployed to its implantation diameter. Prior to deployment, the capsule 1200 prevents the prosthetic valve 10 from expanding due to the natural resiliency of the frame 12, thus keeping the prosthetic valve 10 in a fully crimped configuration during the process of advancing the prosthetic valve 10 through the patient's vasculature toward the implantation site.

Once the prosthetic valve 10 is at a desired implantation position, it can be expanded using the actuators 919 as previously described (or other by actuating any of various other types of expansion devices disclosed herein). As the distal end portion of the prosthetic valve expands, the capsule 1200 slides distally off the distal end portion of the prosthetic valve due to the taper of the frame and the radial expansion force of the prosthetic valve pushing radially outwardly and distally against the sleeve, as indicated by arrow 1210 in FIG. 27. Once the capsule 1200 has been removed from the prosthetic valve, the actuators 919 can continue to expand prosthetic valve 10 until the prosthetic valve reaches a desired working diameter.

In some embodiments, the capsule 1200 can be sufficiently flexible such that it can form circumferentially extending folds or creases that effectively shorten the overall length of the capsule 1200 as it slides off of the prosthetic valve under the radial expansion force of the prosthetic valve.

It should be noted that the distal end portion of the prosthetic valve, when attached to the delivery apparatus, can be the inflow end portion or the outflow end portion of the prosthetic valve, depending on the delivery approach and implantation site. For example, when delivering a prosthetic valve to the native aortic valve in a retrograde approach (e.g., through the aorta), the inflow end portion of the prosthetic valve is in the distal position and is covered by the capsule 1200. As another example, when delivering a prosthetic valve to the native mitral valve in an antegrade approach (e.g., through the inferior or superior vena cava), the outflow end portion of the prosthetic valve is in the distal position and is covered by the capsule 1200.

In alternative embodiments, the capsule 1200 can be coupled to a component of the delivery apparatus at a location proximal to the prosthetic valve 10, for example, to the distal end of the shaft 509, and can extend over at least the proximal end portion of the prosthetic valve when it is in the radially compressed state. Since the prosthetic valve is also slightly tapered from the midsection of the prosthetic valve to the proximal end of the prosthetic valve when radially compressed (due to the bulk of the soft component being located generally in the middle of the frame 12), radial expansion of the prosthetic valve causes the capsule to slide off of the prosthetic valve in the proximal direction under the radial expansion force of the prosthetic valve.

As shown in FIGS. 28-32, in some particular embodiments, a delivery assembly 500 can further comprise a crimping mechanism 1300. A delivery assembly 500 can include a prosthetic valve (e.g., a prosthetic valve 10 or any of the other prosthetic valves disclosed herein), a delivery apparatus 502, and a crimping mechanism 1300. The crimping mechanism 1300 can facilitate crimping of a prosthetic valve, such as prosthetic valve 10, after the prosthetic valve 10 has been exposed from outer sheath 510 inside the patient, as discussed in more detail below.

In some cases, the crimping mechanism 1300 can also be used to maintain the prosthetic valve 10 in a fully crimped configuration as prosthetic valve 10 is advanced through the patient's body to the implantation site and after the prosthetic valve is exposed from outer sheath 510, thus preventing or at least mitigating any expansion caused by the inherent resiliency of the frame 12. Maintaining the crimped configuration of the prosthetic valve 10 during retraction of the sheath 510 can help mitigate radial or axial 'jumps' (i.e., unplanned movements of the prosthetic valve) caused by inherent frame expansion, and thereby maximize the physician's control over positioning the prosthetic valve. In this manner, the mechanism 1300 is used to maintain the prosthetic valve in the radially compressed state, rather than for crimping the prosthetic valve after partial or full expansion. In some embodiments, the delivery apparatus can be without a sheath 510 and the crimping mechanism 1300 serves as a retaining mechanism that retains the prosthetic valve in its radially compressed state while being delivered through the patient's body to the desired implantation site.

In the embodiment of FIGS. 28-32, the prosthetic valve 10 includes expansion and locking mechanisms 900 and the crimping mechanism 1300 is therefore described in connection with expansion and locking mechanisms 900. In alternative embodiments, the crimping mechanism 1300 can be used with various other types of expansion mechanisms, such as actuators 20 (described above). Because the crimping mechanism 1300 is coupled to the prosthetic valve 10 directly, the risk of capturing the native leaflets during crimping is mitigated.

As previously described, the prosthetic valve 10 can include one or more expansion and locking mechanisms 900 releasably coupled to actuator mechanisms 919 of the delivery apparatus 502 as previously described. Each actuator mechanism 919 transmits force from the handle 504 of the delivery apparatus to a respective expansion and locking mechanism 900.

Figure 30:
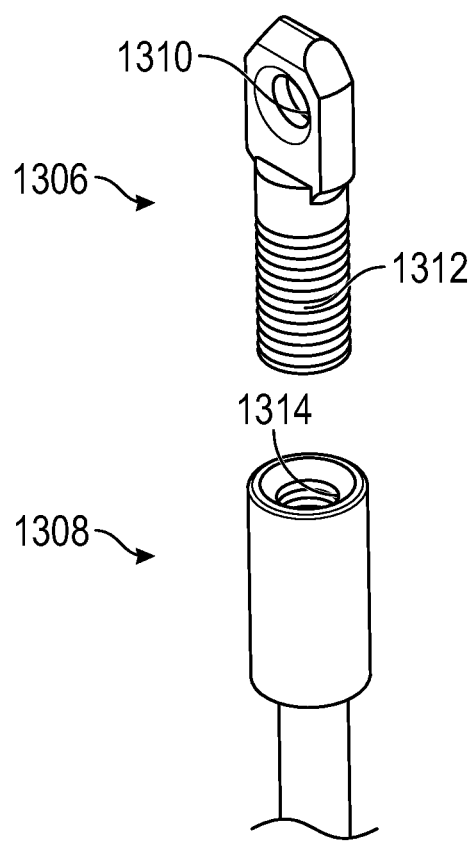
FIG. 30 is an enlarged, exploded view of a portion of a crimping mechanism.
Figure 31:
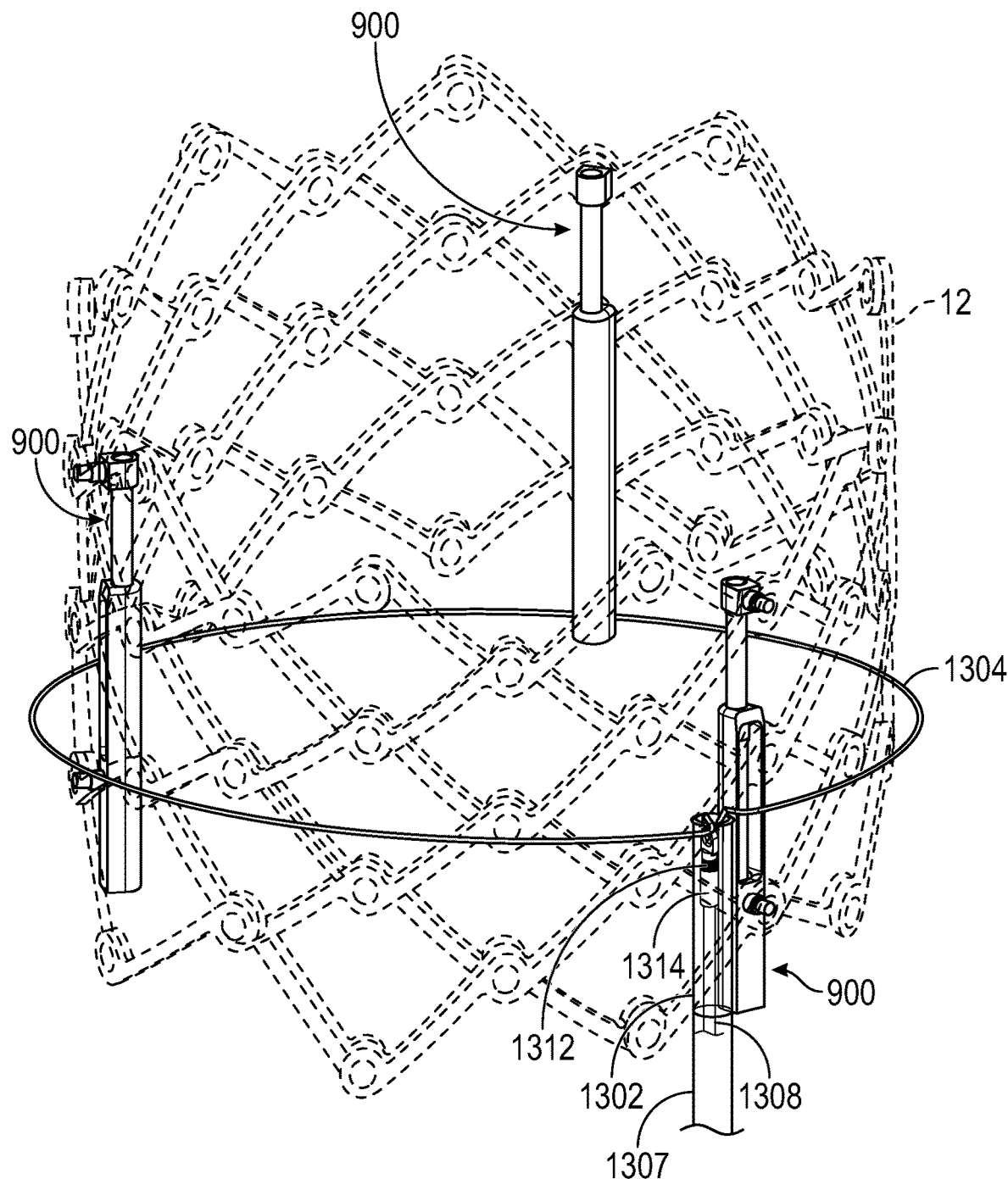
FIG. 31 is a perspective view of the prosthetic valve and crimping mechanism of FIG. 28 further comprising a tension member actuator and a sheath.

The crimping mechanism 1300 can comprise a support tube 1302, a tension member 1304, a connector 1306, and a tension member actuator 1308 (see FIG. 30). As shown in FIG. 30, the connector 1306 can comprise an opening 1310 and a threaded portion 1312. In some embodiments, as shown in FIG. 31, a sheath or tube 1307 can extend over the tension member actuator 1308 the length of the delivery apparatus from handle to the support tube 1302. The sheath 1307 can have a proximal end portion connected to the handle 504 of the delivery apparatus and a distal end portion that abuts a proximal end of the support tube 1302.

Figure 28:
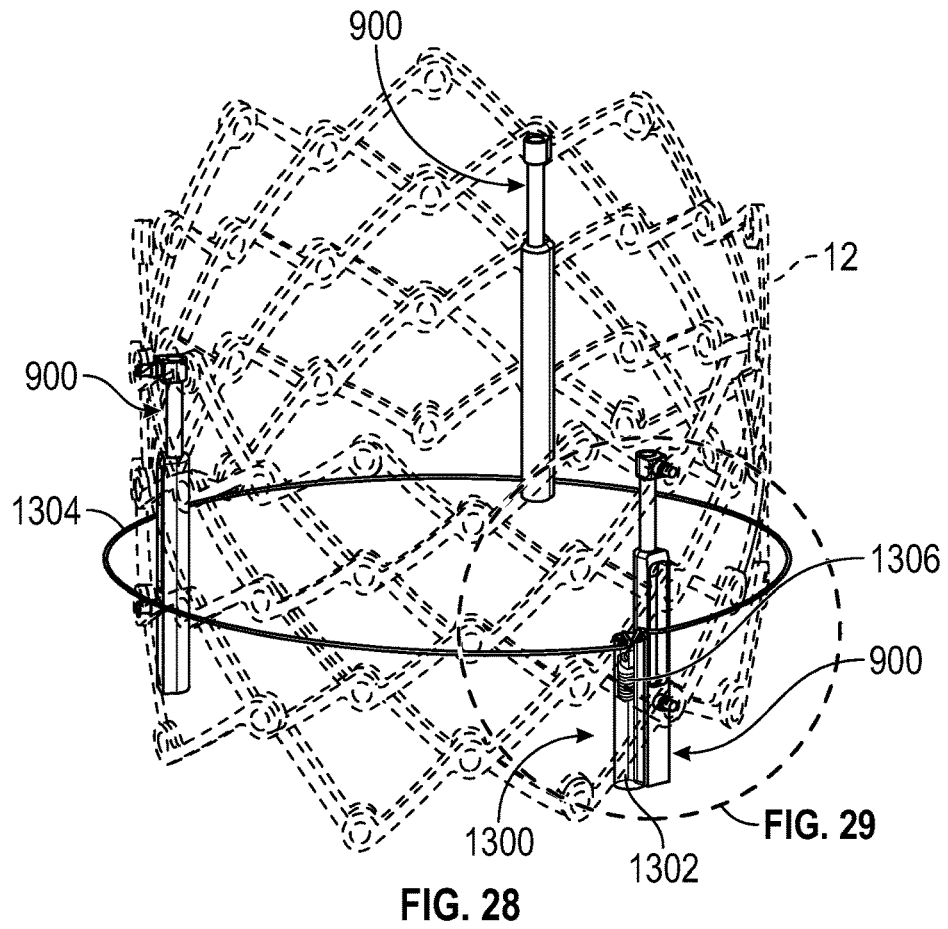
FIG. 28 is a perspective view of a prosthetic heart valve including a crimping mechanism coupled to the prosthetic valve, in one embodiment.
Figure 32:
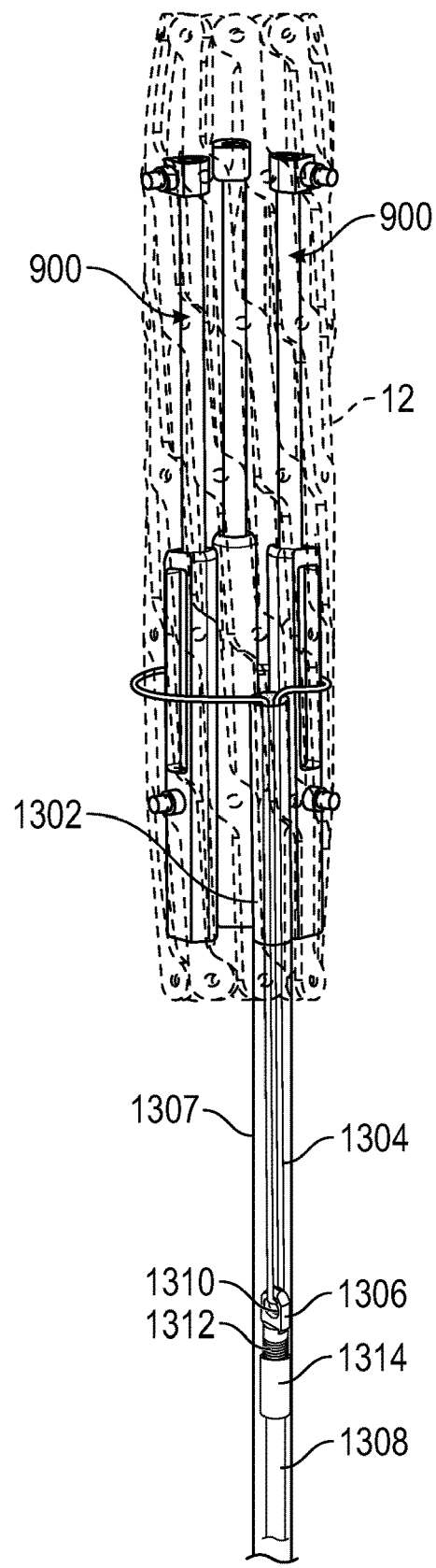
FIG. 32 is a side elevational view of the prosthetic valve and crimping mechanism of FIG. 28, shown with the prosthetic valve in the fully compressed configuration.

The support tube 1302 can be coupled (e.g., by welding, an adhesive, a mechanical fastener, or other means) to the prosthetic valve 10. For example, as shown in FIG. 28, the support tube 1302 can be coupled to one of the expansion and locking mechanisms 900 inside of the frame 12. In other embodiments, the support tube 1302 can be coupled directly to the frame 12 of the prosthetic valve 10. The tension member 1304 can extend around an external circumference of the prosthetic valve 10, thus forming a loop around the frame 12. The tension member 1304 can have a first end and a second end which can be coupled together (e.g., by knotting, bonding, or other type of connection) to form a closed loop, which is coupled to the connector 1306. For example, the loop can extend through the opening 310 in the connector 1306, as best shown in FIG. 32. Alternatively, the first and second ends of the tension member can be coupled to the connector 1306 directly.

The tension member can be, for example, a suture (e.g., a single filament suture or a multi-filament suture), a flexible wire (e.g., a metal wire formed from stainless steel, Nitinol or other suitable metals), a cable (e.g., a braided cable formed from metal or polymeric strands) or any other similar materials that can be placed in tension to radially compress the prosthetic valve as described herein.

In some embodiments (see e.g., FIG. 33), the tension member 1304 can extend through a sleeve 1324 coupled to and extending around a circumference of the frame 12 of the prosthetic valve. The sleeve 1324 can prevent the tension member 1304 from sliding axially along the length of the prosthetic valve. The sleeve can be formed from any of various suitable biocompatible materials, including any of various synthetic materials (e.g., PET) or natural tissue (e.g., pericardial tissue).

Figure 33:
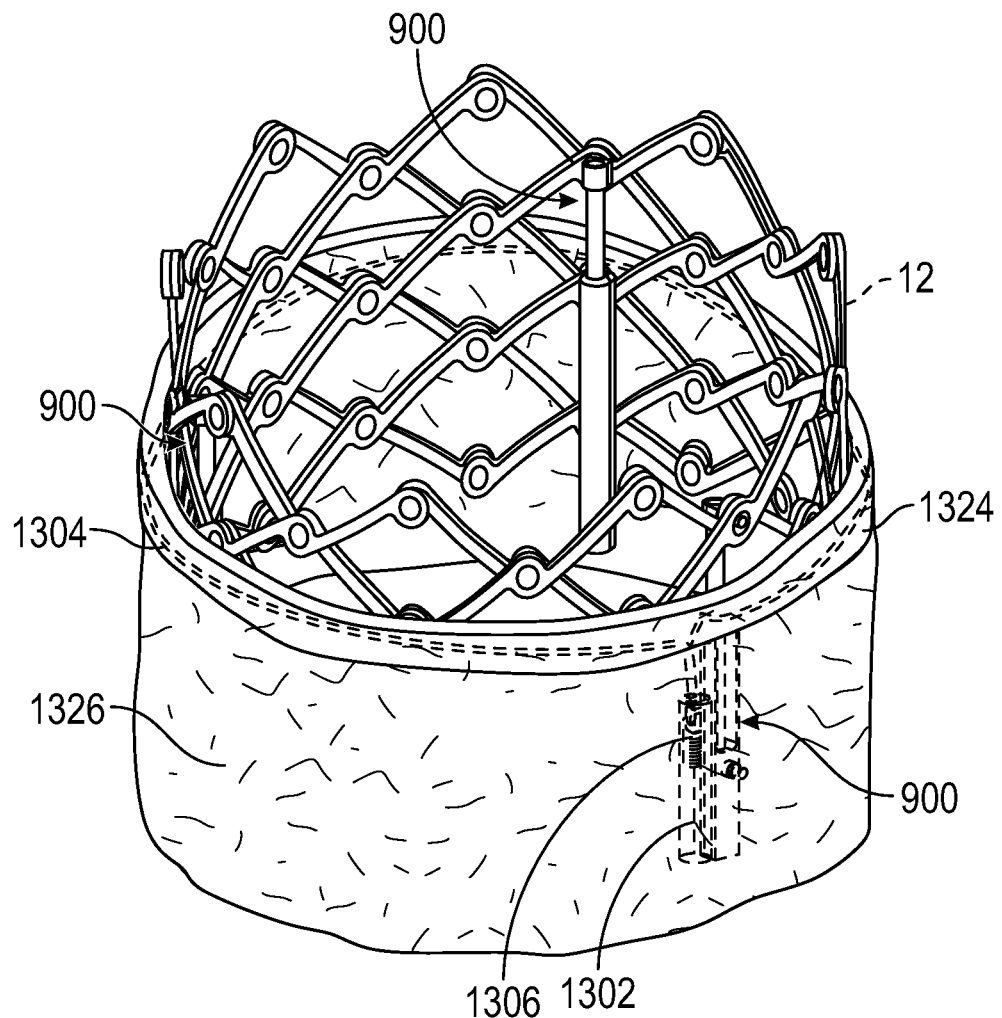
FIG. 33 is a perspective view of a prosthetic heart valve including a crimping mechanism coupled to the frame, in one embodiment.

In embodiments wherein the prosthetic valve 10 includes an outer skirt or sealing member, such as the embodiment shown in FIG. 33 having an outer skirt 1326, the sleeve 1324 can be formed by folding a proximal edge portion of a skirt or sealing member distally and securing the folded edge (e.g., by sutures and/or an adhesive) to an adjacent portion of the skirt such that a sleeve is formed. In other embodiments, the sleeve 1324 can be separate from the outer skirt 1326 and can be mounted to the frame using sutures, an adhesive, welding, and/or other means for attaching the sleeve to the frame. In still other embodiments, the sleeve 1324 can be separately formed and subsequently connected to a proximal end of the skirt 1326 using sutures, an adhesive, welding, and/or other means.

Figure 29:
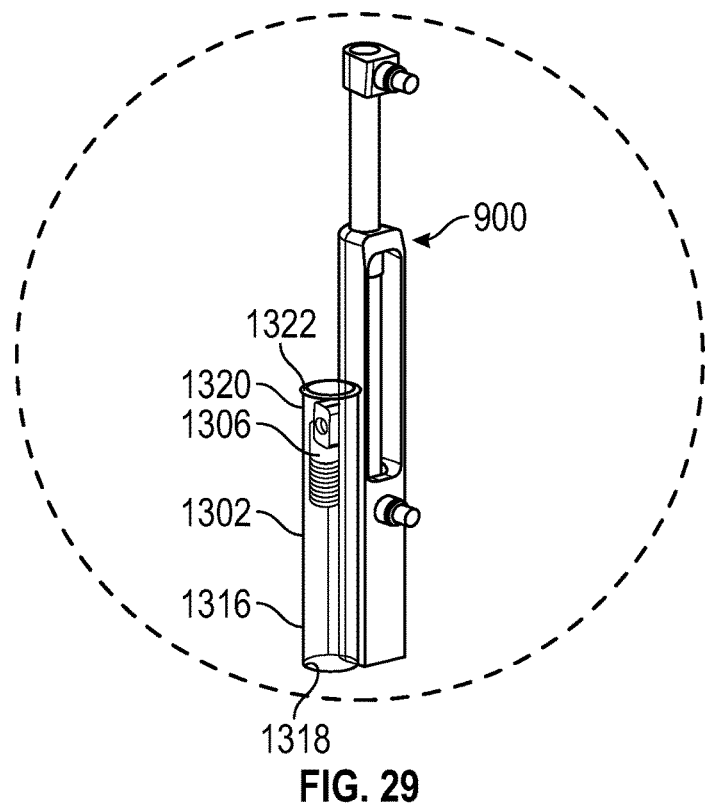
FIG. 29 is an enlarged view of a portion of the crimping mechanism of FIG. 28.

Referring to FIG. 29, the support tube 1302 can have a proximal end portion 1316 comprising a proximal aperture 1318, a distal end portion 1320 comprising a distal aperture 1322, and an inner lumen. As shown, the connector 1306 can be disposed within the inner lumen of the support tube 1302. The inner lumen can have a diameter sized to allow the connector 1306 and/or the tension member actuator 1308, including a threaded receiving portion 1314 of the actuator 1308, to move axially within the lumen. In some embodiments, the distal end portion 1320 of the support tube can comprise a protrusion or cap sized to prevent the connector 1306 from exiting the support tube 1302 through the distal aperture 1322. In the illustrated embodiment, the first and second ends of the tension member 1304 extend into the support tube 1302 through the distal aperture 1322. However, in other embodiments, in lieu of or in addition to the distal aperture 1322, the distal end portion of the support tube can comprise openings spaced apart around the circumference of the support tube, through which the first and second ends of the tension member can extend in order to couple to the connector.

The threaded portion 1312 of the connector 1306 can be releasably coupled to the correspondingly threaded receiving portion 1314 at the distal end portion of the tension member actuator 1308. In the illustrated embodiment, the threaded portion 1312 has external threads that mate with internal threads of the receiving portion 1314. In other embodiments, the threaded portion 1312 has internal threads that mate with external threads of the receiving portion 1314.

In some embodiments, in lieu of or in addition to the threaded portion and the threaded receiving portion, the connector 1306 and the tension member actuator 1308 can comprise alternative means for releasably coupling the connector and the tension member actuator. For example, the connector 1306 can comprise a magnet and the tension member actuator 1308 can comprise a corresponding magnet, such that the connector can be magnetically coupled to the tension member actuator 1308. In another example, the connector 1306 can comprise a hook and the tension member actuator 1308 can comprise a correspondingly sized loop, or vice versa.

In the depicted embodiment, the tension member actuator 1308 can be releasably coupled to the tension member 1304 by advancing the threaded receiving portion 1314 distally through the lumen of the support tube 1302 until the threaded receiving portion 1314 engages the threaded portion 1312 of the connector 1316, as shown in FIG. 31. The tension member actuator 1308 can be rotated in a first direction (e.g., clockwise) such that the threads of the threaded receiving portion 1314 engage the threads of the threaded portion 1312 of the connector 1306. Thus coupled, the crimping mechanism can be actuated to radially compress the prosthetic valve, as described in more detail below.

The tension member actuator 1308 can be, for example, a pull cable, a wire, or shaft, and can have a proximal end portion coupled to the handle 504 and a distal end portion coupled to the threaded receiving portion 1314. The handle 504 can include a knob or other actuation mechanism operatively coupled to the actuator 1308 to apply a force to the actuator 1308 and thereby to the tension member 1304, as described in further detail below.

The actuator 1308 and the sheath 1307 can extend along the longitudinal axis parallel to the support tubes 920 of the delivery apparatus 502. The actuator 1308 can be releasably coupled to the tension member 1304 (such as via the connector 1306) at a location circumferentially offset from the actuator mechanisms 919. The distal end portion of the sheath 1307 can abut the proximal end portion 1316 of the support tube 1302.

The crimping mechanism 1300 can be used to radially compress a prosthetic heart valve, such as prosthetic heart valve 10, in the following exemplary manner. The prosthetic valve 10 can be connected to the delivery apparatus 502 in the manner described above, and the tension member actuator 1308 of the crimping mechanism 1300 can be coupled to the tension member 1304 in the manner described above. The distal end portion of the delivery apparatus (along with prosthetic valve 10) can be advanced through the vasculature of a patient to a selected implantation site. The prosthetic valve 10 can then be deployed at the implantation site (e.g., the native aortic annulus).

In some cases, after deployment from the sheath 510, the prosthetic valve 10 can expand slightly due to the inherent resiliency of the frame 12. In such cases, the physician can use the crimping mechanism 1300 to compress the prosthetic valve 10 to a fully compressed configuration such that it can be more easily positioned at the implantation site. The physician can apply an axial force in the proximal direction (e.g., a pulling force) to the actuator 1308 (and thus to tension member 1304) using the handle 504. As shown in FIG. 32, applying an axial force to the tension member 1304 places the tension member 1304 in tension around the circumference of the frame 12, thereby radially compressing the frame. In some cases, in lieu of or in addition to applying an axial force in the proximal direction to the actuator 1308, the physician can apply an axial force in the distal direction (e.g., a pushing force) to the sheath 1307.

Alternatively, in some cases, the physician can use the crimping mechanism 1300 to maintain the valve in a fully crimped position prior to the retraction of outer sheath 510, thus preventing or at least mitigating any expansion caused by the inherent resiliency of the frame 12. Maintaining the crimped configuration of the prosthetic valve 10 during retraction of the sheath 510 can help mitigate radial or axial 'jumps' (i.e., unplanned movements of the prosthetic valve) caused by inherent frame expansion, and thereby maximize the physician's control over positioning the prosthetic valve. In this manner, the mechanism 1300 is used to maintain the prosthetic valve in the radially compressed state, rather than for re-crimping the prosthetic valve after partial or full expansion.

Once the prosthetic valve 10 is positioned at the desired implantation site, the applied force on the actuator 1308 can be released (thereby releasing tension on the tension member 1304) and the prosthetic valve can be expanded using the expansion and locking mechanisms 900 as previously described herein. As the prosthetic valve 10 expands, the connector 1306 can slide distally within the lumen of the support tube 1302 thereby exposing a greater portion of the tension member 1304 from the distal end 1320 of support tube 1302, thereby allowing the diameter of the loop formed by the tension member 1304 to increase as the prosthetic valve radially expands. The tension member actuator 1308 can be uncoupled from the tension member 1304 by rotating the tension member actuator 1308 in a second direction (e.g., counterclockwise) such that the threads of the threaded receiving portion 1314 disengage from the threaded portion 1312 of the connector 1306. During the de-coupling step, rotation of the connector 1306 within the support tube is resisted by virtue of the loop extending through the opening 1310 being fully expanded and held in tension around the expanded prosthetic valve. In alternative embodiments, the lumen of the support tube 1302 can have a feature, such as a longitudinally extending slot or rail that permits axial movement of the connector 1306 within the support tube 1302 but prevents rotation of the connector 1306 within the support tube. The delivery apparatus (including tension member 1308) can then be released from the prosthetic valve and removed from the body. In some cases, the tension member actuator 1308 can be uncoupled from the tension member 1304 prior to the expansion of the prosthetic valve 10.

Additionally, in some cases, once the prosthetic valve has been at least partially expanded or fully expanded, the physician can determine whether the prosthetic valve needs to be repositioned. In such cases, the physician can use the crimping mechanism 1300 to fully compress the prosthetic heart valve using the method described above in order to reposition the prosthetic valve 10 at the implantation site. Once prosthetic valve 10 has been repositioned, it can be expanded using the expansion and locking mechanisms 900, as previously described herein. The prosthetic valve 10 can be re-crimped, re-positioned, and re-expanded multiple times, as needed. In some cases, the prosthetic valve 10 can be fully compressed and "recaptured" (retracted back into the sheath 510) and then removed from the patient's body.

Crimping mechanism 1300 advantageously does not require distal advancement of the sheath 510 in order to re-crimp the prosthetic valve 10. This mitigates the likelihood of causing trauma to the patient's anatomy by advancing sheath 510 distally. Distal advancement of a sheath without an attached nosecone can result in rubbing or scraping of the patient's anatomy, which can, for example, result in stroke in cases where the patient's anatomy has calcified. Furthermore, because the tension member remains coupled to the valve after implantation, crimping mechanism 1300 advantageously mitigates the risk of capturing and/or damaging the native leaflets during the crimping and release procedures.

Additionally, the crimping mechanism 1300 allows the prosthetic valve 10 to be re-crimped in place without significant distal or proximal movement of the prosthetic valve. This allows the physician to re-crimp the prosthetic valve 10 and fine-tune its positioning without having to restart the positioning process from the beginning (e.g., by recapturing the prosthetic valve into the sheath 510). In some cases, recapturing the prosthetic valve into the sheath for repositioning can result in damage to the prosthetic valve. The crimping mechanism 1300 allows the valve to be re-crimped and repositioned while mitigating the risk of damage to the prosthetic valve because the prosthetic valve does not need to be re-inserted into sheath 510.

The crimping mechanism 1300 can be used with any of the prosthetic valves described herein (e.g., prosthetic valves 10, 100, 200, 300, 400, 700, and 800). For example, crimping mechanism 1300 can be used to compress a prosthetic valve that normally assumes a tapered shape while in the compressed configuration, such as prosthetic valve 800 having expansion actuators (e.g., the expansion and locking mechanisms 900), into a cylindrical or substantially cylindrical configuration to facilitate positioning/re-positioning of the prosthetic valve inside the patient's body and/or recapture of the prosthetic valve back into the sheath 510.

Explaining further, after the outer sheath 510 of the delivery apparatus 502 is retracted, the prosthetic valve 800 normally assumes a tapered configuration wherein a diameter of the proximal end of the prosthetic valve (e.g., the outflow end 826 when the prosthetic valve is mounted for retrograde delivery) is greater than a diameter of the distal end of the prosthetic valve (e.g., the inflow end 824 when the prosthetic valve is mounted for retrograde delivery) (see e.g., FIG. 17C). The support tube 1302 can be coupled to the prosthetic valve 10 such that the tension member 1304 is positioned around the outflow end 826 of the prosthetic valve 800. The physician can actuate the tension member actuator 1308 of the crimping mechanism, thereby applying radial forces to the distal end 826 of the prosthetic valve and compressing the outflow end to substantially the same diameter as the inflow end. Because the crimping mechanism is offset to one side of the prosthetic valve, it can compensate for the larger diameter of the outflow end 826 of the prosthetic valve 800, thus crimping the prosthetic valve 800 into a substantially cylindrical configuration.

In alternative embodiments, the crimping mechanism 1300 can be incorporated in delivery apparatuses having other types of actuator assemblies and can be used with prosthetic valves having other types of actuators than the type shown in FIGS. 28-33. Further, the tension member 1304 need not be looped around the frame 12 of the prosthetic valve or around components of the actuator assemblies of the delivery apparatus. For example, a delivery apparatus can have a plurality of circumferentially spaced connecting members, such as in the form of fingers or shafts, that form a releasable connection with a prosthetic valve but do not necessarily function as actuators for expanding the prosthetic valve, such as disclosed in U.S. Publication No. 2012/0239142. In such cases, the tension member 1304 can be looped around the connecting members in the same manner as shown in FIG. 28 and can function to radially compress the prosthetic valve in situ.

General Considerations

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

All features described herein are independent of one another and, except where structurally impossible, can be used in combination with any other feature described herein. For example, the frames of prosthetic valves 10, 100, 200, or 300 (shown in FIGS. 1-9) can incorporate the tapered portion 408 as shown in FIG. 11.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An implantable prosthetic device, comprising:
a frame that is radially expandable and compressible between a radially compressed configuration and a radially expanded configuration, the frame comprising
a first set of a plurality of struts extending in a first direction, and
a second set of a plurality of struts extending in a second direction;
wherein each strut of the first set of struts is pivotably connected to at least one strut of the second set of struts to define a plurality of circumferentially extending rows of cells;
wherein each strut is curved helically with respect to a first, longitudinal axis of the frame;
wherein each strut is curved with respect to a second axis that is perpendicular to the first, longitudinal axis of the frame;
wherein each strut is a unitary member that extends from a first end of the frame to a second end, and each strut comprises a plurality of segments between locations where struts are pivotally connected to each other and each segment of a respective strut is laterally offset from each adjacent segment of the respective strut in a direction perpendicular to the overall length of the strut such that the strut is curved along a length of the strut;
wherein the frame has a first diameter at the first end and a second diameter at the second end, and when the frame is in the radially expanded configuration the second diameter is larger than the first diameter; and
wherein when the frame is in the radially compressed configuration the second diameter is smaller than the first diameter.

2. The implantable prosthetic device of claim 1, wherein each strut is concave with respect to an outflow end of the frame.

3. The implantable prosthetic device of claim 1, wherein each strut is convex with respect to an outflow end of the frame.

4. The implantable prosthetic device of claim 1, wherein when the frame is in a radially expanded configuration the frame tapers from a first diameter at a first location on the frame to a second diameter at a second location on the frame axially spaced from the first location, the first diameter being greater than the second diameter.

5. The implantable prosthetic device of claim 1, wherein each strut comprises a plurality of segments between locations where struts are pivotally connected to each other and wherein each segment is curved with respect to the second axis such that the strut is curved along a length of the strut.

6. The implantable prosthetic device of claim 1, wherein a length of each segment increases relative to an immediately preceding segment from a first end of the frame to a second end of the frame.

7. The implantable prosthetic device of claim 1, wherein each strut extends from a first end of the frame to an axially opposed second end of the frame.

8. The implantable prosthetic device of claim 1, further comprising a valve assembly comprising a plurality of leaflets mounted inside the frame.

9. An implantable prosthetic device, comprising:
a frame having first and second opposing axial ends, the frame comprising:
a first set of a plurality of struts extending in a first direction, and
a second set of a plurality of struts extending in a second direction, the second set of struts overlapping the first set of struts and connected to the first set of struts by pivot elements to define a plurality of circumferentially extending rows of cells,
wherein each strut is curved along a length of the strut and has first and second longitudinal edges extending along the length, the first longitudinal edge forming a convex curve facing the first end of the frame and the second longitudinal edge forming a concave curve facing the second end of the frame;
wherein each strut is a unitary member that extends from an inflow end of the frame to an outflow end of the frame;
wherein the frame has a first diameter at a first end and a second diameter at a second end, and when the frame is in a radially expanded configuration the second diameter is larger than the first diameter; and
wherein when the frame is in a radially compressed configuration the second diameter is smaller than the first diameter.

10. The implantable prosthetic device of claim 9, wherein each strut comprises a plurality of segments and a length of each segment increases relative to an immediately preceding segment from a first end of the frame to a second end of the frame.

11. The implantable prosthetic device of claim 9, wherein a projection of each strut in a plane parallel to a longitudinal axis of the frame is curved.

12. An implantable prosthetic device, comprising:
a frame movable between a radially compressed configuration and a radially expanded configuration, the frame comprising a first set of a plurality of struts and a second set of a plurality of struts overlapping the first set and connected to the first set by pivot elements to define a plurality of circumferentially extending rows of cells, each strut being a unitary member that extends from a first end of the frame to a second end;
wherein in the radially expanded configuration an overall shape of the frame is a tapered frustoconical shape;
wherein the frame has a first draft angle when in the radially compressed configuration and a second draft angle when in the radially expanded configuration;
wherein the frame has a first diameter at the first end and a second diameter at the second end, and when the frame is in the radially expanded configuration the second diameter is larger than the first diameter; and
wherein when the frame is in the radially compressed configuration the second diameter is smaller than the first diameter.

13. The implantable prosthetic device of claim 12, wherein the first draft angle is less than the second draft angle.

14. The implantable prosthetic device of claim 12, wherein the first draft angle is greater than the second draft angle.

15. An implantable prosthetic device, comprising:
a radially expandable and compressible frame having first and second opposing axial ends, the frame comprising:
a first set of a plurality of struts extending in a first direction, and
a second set of a plurality of struts extending in a second direction, each strut of the second set of struts being coupled to a plurality of struts of the first set of struts to define a plurality of circumferentially extending rows of cells;
wherein each strut is a unitary member that extends from the first axial end of the frame to the second axial end;
wherein each strut comprises a non-Euclidian geometry;
wherein when the frame is in a radially expanded configuration angles formed between pivotably connected struts of each row of cells progressively increase from one end of the frame to the other;
wherein the frame has a first diameter at the first axial end and a second diameter at the second axial end, and when the frame is in a radially expanded configuration the second diameter is larger than the first diameter; and
wherein when the frame is in a radially compressed configuration the second diameter is smaller than the first diameter.

16. The implantable prosthetic device of claim 15, wherein each strut comprises an elliptic geometry, and wherein the angles between the pivotably connected struts progressively increase from an inflow end of the frame to an outflow end.

17. The implantable prosthetic device of claim 15, wherein each strut comprises a hyperbolic geometry and wherein the angles between the pivotably connected struts progressively decrease from an inflow end of the frame to an outflow end.

* * * * *